United States Patent
Macdonald et al.

(10) Patent No.: US 12,295,354 B2
(45) Date of Patent: May 13, 2025

(54) NON-HUMAN ANIMALS EXPRESSING EXOGENOUS TERMINAL DEOXYNUCLEOTIDYLTRANSFERASE

(71) Applicant: Regeneron Pharmaceuticals, Inc., Tarrytown, NY (US)

(72) Inventors: Lynn Macdonald, Harrison, NY (US); Andrew J. Murphy, Croton-on-Hudson, NY (US); Chunguang Guo, Thornwood, NY (US); Natasha Levenkova, New York, NY (US); Naxin Tu, Pleasantville, NY (US); John McWhirter, Hastings-on-Hudson, NY (US); Vera Voronina, Sleepy Hollow, NY (US); Faith Harris, Mamaroneck, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1067 days.

(21) Appl. No.: 17/203,398

(22) Filed: Mar. 16, 2021

(65) Prior Publication Data
US 2021/0195877 A1     Jul. 1, 2021

Related U.S. Application Data

(62) Division of application No. 15/612,625, filed on Jun. 2, 2017, now Pat. No. 10,980,221.

(60) Provisional application No. 62/345,524, filed on Jun. 3, 2016.

(51) Int. Cl.
| | |
|---|---|
| A01K 67/0275 | (2024.01) |
| A01K 67/0278 | (2024.01) |
| C07K 14/725 | (2006.01) |
| C07K 16/00 | (2006.01) |
| C07K 16/46 | (2006.01) |
| C12N 5/0735 | (2010.01) |
| C12N 5/0783 | (2010.01) |
| C12N 9/12 | (2006.01) |
| C12N 15/85 | (2006.01) |
| C12N 15/90 | (2006.01) |

(52) U.S. Cl.
CPC ...... *A01K 67/0275* (2013.01); *A01K 67/0278* (2013.01); *C07K 14/7051* (2013.01); *C07K 16/00* (2013.01); *C07K 16/462* (2013.01); *C12N 5/0606* (2013.01); *C12N 5/0636* (2013.01); *C12N 9/1264* (2013.01); *C12Y 207/07031* (2013.01); *A01K 2207/15* (2013.01); *A01K 2217/052* (2013.01); *A01K 2217/072* (2013.01); *A01K 2217/15* (2013.01); *A01K 2227/105* (2013.01); *A01K 2267/01* (2013.01); *C07K 2317/10* (2013.01); *C07K 2317/21* (2013.01); *C07K 2317/24* (2013.01); *C07K 2317/52* (2013.01); *C07K 2317/56* (2013.01); *C07K 2317/565* (2013.01); *C07K 2319/03* (2013.01); *C12N 2015/8518* (2013.01); *C12N 15/907* (2013.01); *C12N 2510/02* (2013.01); *C12N 2830/008* (2013.01)

(58) Field of Classification Search
None
See application file for complete search history.

(56) References Cited

U.S. PATENT DOCUMENTS

| | | |
|---|---|---|
| 5,624,821 A | 4/1997 | Winter et al. |
| 5,633,425 A | 5/1997 | Lonberg et al. |
| 5,648,260 A | 7/1997 | Winter et al. |
| 5,731,168 A | 3/1998 | Carter et al. |
| 5,770,429 A | 6/1998 | Lonberg et al. |
| 5,776,773 A | 7/1998 | Bruggemann |
| 5,807,706 A | 9/1998 | Carter et al. |
| 5,814,318 A | 9/1998 | Lonberg et al. |
| 5,821,333 A | 10/1998 | Carter et al. |
| 5,942,435 A | 8/1999 | Wheeler |
| 6,001,349 A | 12/1999 | Panicali et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,235,883 B1 | 5/2001 | Jakobovits et al. |
| 6,528,624 B1 | 3/2003 | Idusogie et al. |
| 6,586,251 B2 | 7/2003 | Economides et al. |
| 6,596,541 B2 | 7/2003 | Murphy et al. |
| 6,737,056 B1 | 5/2004 | Presta |
| 6,998,514 B2 | 2/2006 | Bruggemann |

(Continued)

FOREIGN PATENT DOCUMENTS

| | | |
|---|---|---|
| WO | WO-2005/116072 A2 | 12/2005 |
| WO | WO-2007/117410 A2 | 10/2007 |

(Continued)

OTHER PUBLICATIONS

L A Bentolila, G E Wu, F Nourrit, M Fanton d'Andon, F Rougeon, N Doyen; Constitutive expression of terminal deoxynucleotidyl transferase in transgenic mice is sufficient for N region diversity to occur at any Ig locus throughout B cell differentiation . . . J Immunol Jan. 15, 1997; 158 (2): 715-723. (Year: 1997).*

(Continued)

*Primary Examiner* — Anna Skibinsky
*Assistant Examiner* — Catherine L McCormick
(74) *Attorney, Agent, or Firm* — Choate, Hall & Stewart LLP; Stephanie L. Schonewald

(57) ABSTRACT

Provided herein are methods and compositions related to non-human animals that express exogenous Terminal Deoxynucleotidyltransferase (TdT).

19 Claims, 18 Drawing Sheets
Specification includes a Sequence Listing.

(56) References Cited

U.S. PATENT DOCUMENTS

| | | |
|---|---|---|
| 7,105,348 B2 | 9/2006 | Murphy et al. |
| 7,122,637 B2 | 10/2006 | Presta |
| 7,183,387 B1 | 2/2007 | Presta |
| 7,294,754 B2 | 11/2007 | Poueymirou et al. |
| 7,297,775 B2 | 11/2007 | Idusogie et al. |
| 7,317,091 B2 | 1/2008 | Lazar et al. |
| 7,332,581 B2 | 2/2008 | Presta |
| 7,501,552 B2 | 3/2009 | Lonberg et al. |
| 7,632,497 B2 | 12/2009 | Stavenhagen |
| 7,642,228 B2 | 1/2010 | Carter et al. |
| 7,662,925 B2 | 2/2010 | Lazar et al. |
| 7,695,936 B2 | 4/2010 | Carter et al. |
| 7,795,494 B2 | 9/2010 | Ghayur |
| 7,910,798 B2 | 3/2011 | Tanamachi et al. |
| 8,093,359 B2 | 1/2012 | Lazar et al. |
| 8,216,805 B2 | 7/2012 | Carter et al. |
| 8,218,805 B2 | 7/2012 | Hornback |
| 8,232,449 B2 | 7/2012 | Tanamachi et al. |
| 8,377,688 B2 | 2/2013 | Delcayre et al. |
| 8,388,955 B2 | 3/2013 | Lazar et al. |
| 8,502,018 B2 | 8/2013 | Murphy et al. |
| 8,530,214 B2 | 9/2013 | Arnould et al. |
| 8,624,000 B2 | 1/2014 | Arnould et al. |
| 8,642,835 B2 | 2/2014 | MacDonald et al. |
| 8,663,622 B2 | 3/2014 | Perera et al. |
| 8,679,785 B2 | 3/2014 | Carter et al. |
| 8,691,502 B2 | 4/2014 | Kupper et al. |
| 8,697,940 B2 | 4/2014 | Macdonald et al. |
| 8,703,485 B2 | 4/2014 | Buelow |
| 8,754,287 B2 | 6/2014 | MacDonald et al. |
| 8,791,323 B2 | 7/2014 | Murphy et al. |
| 8,847,005 B2 | 9/2014 | MacDonald et al. |
| 8,878,001 B2 | 11/2014 | Wang et al. |
| 8,907,157 B2 | 12/2014 | Buelow |
| 9,006,511 B2 | 4/2015 | Macdonald et al. |
| 9,012,717 B2 | 4/2015 | Macdonald et al. |
| 9,029,628 B2 | 5/2015 | Macdonald et al. |
| 9,035,128 B2 | 5/2015 | MacDonald et al. |
| 9,043,996 B2 | 6/2015 | MacDonald et al. |
| 9,066,502 B2 | 6/2015 | Macdonald et al. |
| 9,078,418 B2 | 7/2015 | Wang et al. |
| 9,113,616 B2 | 8/2015 | MacDonald et al. |
| 9,120,662 B2 | 9/2015 | Thomson |
| 9,125,386 B2 | 9/2015 | Wang et al. |
| 9,145,588 B2 | 9/2015 | Throsby et al. |
| 9,163,092 B2 | 10/2015 | Macdonald et al. |
| 9,204,624 B2 | 12/2015 | McWhirter et al. |
| 9,206,263 B2 | 12/2015 | Macdonald et al. |
| 9,228,208 B2 | 1/2016 | Frendewey et al. |
| 9,301,510 B2 | 4/2016 | McWhirter et al. |
| 9,334,334 B2 | 5/2016 | McWhirter et al. |
| 9,796,788 B2 | 10/2017 | McWhirter et al. |
| 2002/0088016 A1 | 7/2002 | Bruggemann |
| 2005/0054832 A1 | 3/2005 | Lazar et al. |
| 2006/0222653 A1 | 10/2006 | Abel et al. |
| 2006/0275282 A1 | 12/2006 | Moore et al. |
| 2006/0275283 A1 | 12/2006 | van Vlijmen et al. |
| 2007/0190063 A1 | 8/2007 | Bahjat et al. |
| 2008/0098490 A1 | 4/2008 | Jakobovits et al. |
| 2008/0154025 A1 | 6/2008 | Lazar et al. |
| 2009/0042291 A1 | 2/2009 | Chu et al. |
| 2010/0146647 A1 | 6/2010 | Logtenberg et al. |
| 2011/0195454 A1 | 8/2011 | McWhirter et al. |
| 2012/0021409 A1 | 1/2012 | McWhirter et al. |
| 2012/0073004 A1 | 3/2012 | MacDonald et al. |
| 2012/0096572 A1 | 4/2012 | Macdonald et al. |
| 2012/0167237 A1 | 6/2012 | Bradley et al. |
| 2012/0192300 A1 | 7/2012 | Babb et al. |
| 2012/0204278 A1 | 8/2012 | Bradley et al. |
| 2013/0018582 A1 | 1/2013 | Miller et al. |
| 2013/0045492 A1 | 2/2013 | Babb et al. |
| 2013/0089541 A1 | 4/2013 | D'Angelo et al. |
| 2013/0096287 A1 | 4/2013 | Macdonald et al. |
| 2013/0108623 A1 | 5/2013 | D'Angelo et al. |
| 2013/0111617 A1 | 5/2013 | MacDonald et al. |
| 2013/0145484 A1 | 6/2013 | Logtenberg et al. |
| 2013/0167256 A1 | 6/2013 | Green et al. |
| 2013/0185819 A1 | 7/2013 | MacDonald et al. |
| 2013/0185821 A1 | 7/2013 | Babb et al. |
| 2013/0195849 A1 | 8/2013 | Spreter Von Kreudenstein et al. |
| 2013/0198879 A1 | 8/2013 | McWhirter et al. |
| 2013/0198880 A1 | 8/2013 | Babb et al. |
| 2013/0219535 A1 | 8/2013 | Wabl et al. |
| 2013/0247236 A1 | 9/2013 | McWhirter et al. |
| 2013/0302836 A1 | 11/2013 | McWhirter et al. |
| 2013/0326647 A1 | 12/2013 | Macdonald et al. |
| 2014/0013275 A1 | 1/2014 | Ochi et al. |
| 2014/0013456 A1 | 1/2014 | McWhirter et al. |
| 2014/0093908 A1 | 4/2014 | Ebi et al. |
| 2014/0212416 A1 | 7/2014 | Friedrich et al. |
| 2014/0245466 A1 | 8/2014 | MacDonald et al. |
| 2014/0245467 A1 | 8/2014 | MacDonald et al. |
| 2014/0245468 A1 | 8/2014 | McWhirter et al. |
| 2014/0310828 A1 | 10/2014 | Lee et al. |
| 2015/0037337 A1* | 2/2015 | Friedrich ............ G01N 33/569 435/7.92 |
| 2015/0059009 A1 | 2/2015 | McWhirter et al. |
| 2015/0113668 A1 | 4/2015 | Bruggemann et al. |
| 2015/0159174 A1 | 6/2015 | Frendewey et al. |
| 2015/0266976 A1 | 9/2015 | Babb et al. |
| 2015/0289489 A1 | 10/2015 | MacDonald et al. |
| 2015/0313193 A1 | 11/2015 | McWhirter et al. |
| 2015/0376628 A1 | 12/2015 | Schoenherr et al. |
| 2015/0376650 A1 | 12/2015 | Auerbach et al. |
| 2015/0376651 A1 | 12/2015 | Frendewey et al. |
| 2016/0046960 A1 | 2/2016 | Frendewey et al. |
| 2016/0060657 A1 | 3/2016 | Frendewey et al. |
| 2016/0081314 A1 | 3/2016 | Thurston et al. |
| 2016/0115486 A1 | 4/2016 | Schoenherr et al. |

FOREIGN PATENT DOCUMENTS

| | | |
|---|---|---|
| WO | WO-2008/151081 A1 | 12/2008 |
| WO | WO-2009/157771 A2 | 12/2009 |
| WO | WO-2010/039900 A2 | 4/2010 |
| WO | WO-2011/004192 A1 | 1/2011 |
| WO | WO-2011/123708 A2 | 10/2011 |
| WO | WO-2013/041844 A2 | 3/2013 |
| WO | WO-2013/041846 A2 | 3/2013 |
| WO | WO-2013/063361 A1 | 5/2013 |
| WO | WO-2014/093908 A2 | 6/2014 |
| WO | WO-2016/044745 A1 | 3/2016 |
| WO | WO-2016/164492 A2 | 10/2016 |
| WO | WO-2017/210586 A1 | 12/2017 |

OTHER PUBLICATIONS

Barthold S., Genetically altered mice: phenotypes, no phenotypes, and Faux phenotypes, Genetica, vol. 122, pp. 75-88 (2004).

Benedict et al., Increased junctional diversity in fetal B cells results in a loss of protective antiphosphorylcholine antibodies in adult mice, Immunity, 10:607-617 (1999).

Benedict et al., Terminal deoxynucleotidyl transferase and repertoire development, Immunol Rev, 175(1):150-157 (2000).

Benedict et al., The long isoform of terminal deoxynucleotidyl transferase enters the nucleus and, rather than catalyzing nontemplated nucleotide addition, modulates the catalytic activity of the short isoform, J Exp Med, 193(1):89-99 (2001).

Bentolila et al., Constitutive expression of terminal deoxynucleotidyl transferase in transgenic mice is sufficient for N region diversity to occur at any Ig locus throughout B cell differentiation., J Immunol, 158(2):715-723 (1997).

Bentolila et al., The two isoforms of mouse terminal deoxynucleotidyl transferase differ in both the ability to add N reaions and subcellular localization, EMBO J, 14(17):4221-4229 (1995).

Bichi et al., Human chronic lymphocytic leukemia modeled in mouse by targeted TCL 1 expression, Proc Natl Acad Sci U S A, 99(10): 6955-6960 (2002).

Bitton, N. et al., Gene therapy approaches to HIV-infection: immunological strategies: use of T bodies and universal receptors to redirect cytolytic T-cells, Front Biosci., 4:D386-93 (1999).

(56) References Cited

OTHER PUBLICATIONS

Bogue et al., Regulation of N-region diversity in antigen receptors through thymocyte differentiation and thymus ontogeny, Proc Natl Acad Sci U S A, 89(22):11011-11015 (1992).
Boule et al., Additions and Corrections, J Biol Chem, 275(42): p. 33184 (2000).
Brevini et al. No shortcuts to pig embryonic stem cells Theriogenology 74 (2010) 544-550.
Brüggemann et al., Immunoglobulin heavy chain locus of the rat: Striking homology to mouse antibody genes, Proc Natl Acad Sci USA, 83:6075-6079 (1986).
Cabaniols et al., Most α/βT cell receptor diversity is due to terminal deoxynucleotidyl transferase, J Exp Med, 194(9):1385-1390 (2001).
Collins et al., The mouse antibody heavy chain repertoire is germline-focused and highly variable between inbred strains, Philos Trans R Soc Land B Biol Sci, 370(1676): 20140236 (2015).
Crusio, W.E., Flanking Gene and Genetic Background Problems in Genetically Manipulated Mice, Biol. Psychiatry, vol. 56, pp. 381-385 (2004).
Das et al., Analysis of the Immunoglobulin Light Chain Genes in Zebra Finch: Evolutionary Implications, Mol. Biol. Evol., 27(1):113-120 (2010).
Di Noia et al., Annu. Rev. Biochem, 76:1-22 (2007).
Di Santo et al., Human terminal deoxynucleotidyl transferases as novel targets for anticancer chemotherapy, Curr Med Chem, 13:2353-2368 (2006).
Doetschman T., Influence of Genetic Background of Genetically Engineered Mouse Phenotypes, Methods Mol. Biol., vol. 530, pp. 423-433 (2009).
Doyen et al., Differential splicing in mouse thymus generates two forms of terminal deoxynucleotidyl transferase, Nucleic Acids Res, 21 (5):1187-1191 (1993).
Doyen et al., Evidence that the long murine terminal deoxynucleotidyltransferase isoform plavs no role in the control of V (D) J iunctional diversitv, J Immunol, 172:6764-6767 (2004).
Gama Sosa, MA., et al., Animal transgenesis: an overview, Brain Struct Funct., 214(2-3):91-109 (2010).
Gilfillan et al., Mice lacking TdT: mature animals with an immature lymphocyte repertoire, Science, 261(5125):1175-1178 (1993).
Giraldo, P. and Montoliu, L., Size matters: use of YACs, BACs and PACs in transgenic animals, Transgenic Research, 10:83-103 (2001).
Glusman et al., Comparative genomics of the human and mouse T cell receptor loci, Immunity, 15(3):337-349 (2001).
Haeryfar et al., Terminal deoxynucleotidyl transferase establishes and broadens antiviral CD8+ T cell immunodominance hierarchies, J Immunol, 181 :649-659 (2008).
Hoffmann, R., Gene expression patterns in human and mouse B cell development, Curr Top Microbial Immunol, 294:19-29 (2005).
Hong et al., Derivaction and Characterization of Embryonic Stem Cells Lines Derived from Transgenic Fischer 344 and Dark Agouti Rats, Stem Cells and Development, vol. 21(9), pp. 1571-1586 (2012).
International Search Report and Written Opinion for International Application No. PCT/US2017/035731 dated Sep. 1, 2017.
Ivics et al., Germline transgenesis in pigs by cytoplasmic microinjection of Sleeping Beauty transposons, Nature Protocols. 9(4):810-827 (2014).
Jensen-Seaman et al., Comparative recombination rates in the rat, mouse, and human aenomes, Genome Research, 14:528-538 (2004).
Kaushik, A. et al., Veterinary Immunology and Immunopathology, Novel insight into antibody diversification from cattle, Veterinary Immunology and Immunopathology, 87:347-350 (2002).
Kim et al., Single chain MHC I trimer-based DNA vaccines for protection against Listeria monocytogenes infection, Vaccine, 30(12):2178-2186 (2012).
Kim et al., Single-chain HLA-A2 MHC trimers that incorporate an immundominant peptide elicit protective T cell immunity against lethal West Nile virus infection, J Immunol, 184(8):4423-4430 (2010).

Komori et al., Lack of N regions in antigen receptor variable region genes of TdT-deficient lymphocytes, Science, 261(5125):1171-1175 (1993).
Lavial et al., Chicken embryonic stem cells as a non-mammalian embryonic stem cell model, Dev Growth Differ., 52(1):101-14 (2010).
Lee et al., The application of transgenic mice for therapeutic antibody discovery, Methods in Molecular Biology, 901 :137-148 (2012).
Li et al., The regulated expression of B lineage associated genes during B cell differentiation in bone marrow and fetal liver, J Exp Med, 178:951-960 (1993).
Li et al., Transgenic mice with a diverse human T cell antigen receptor repertoire, Nat Med, 16: 1029-1 035 (2010).
Longo, N. et al., Mechanisms That Shape Human Antibody Repertoire Development in Mice Transgenic for Human Ig H and L Chain Loci, The Journal of Immunology, 198, 15 pages (2017).
Ma, Y. et al., Building Cre Knockin Rat Lines Using CRISPR/Cas9, Methods and Protocols, Methods in Molecular Biology, 1642:37-52 (2017).
Ma, Y. et al., CRISPR/Cas9-mediated targeting of the Rosa26 locus produces Cre reporter rat strains for monitoring Cre-loxP-mediated lineage tracing, The FEBS Journal, 284:3262-3277 (2017).
Macdonald, LE et al., Precise and in situ genetic humanization of 6 Mb of mouse immunoglobulin genes, Proc Natl Acad Sci USA, 111(14):5147-52 (2014).
Martin et al., Positive selection from newly formed to marginal zone B cells depends on the rate of clonal production, CD19, and btk, Immunity, 12:39-49 (2000).
Meng et al,, Optimized production of transgenic buffalo embryos and offspring by cytoplasmic zygote injection, Journal of Animal Science and Biotechnology, pp. 1-7 (2015).
Mombaerts et al., Creation of a large genomic deletion at the T-cell antigen receptor betasubunit locus in mouse embryonic stem cells by gene targeting., Proc Natl Acad Sci USA, 88:3084-3087 (1991).
Mombaerts et al., Mutations in T-cell antigen receptor genes alpha and beta block thymocyte development at different stages, Nature, 360:225-231 (1992).
Motea et al., Terminal deoxynucleotidyl transferase: the story of a misguided DNA polymerase, Biochim Bio phys Acta, 1804(5): 1151-1166 (2010).
Munoz et al., Conventional pluripotency markers are unspecific for bovine embryonic-derived cell-lines, Theriogenology, 69(9):1159-1164 (2008).
Paris et al,, Equine embryos and embryonic stem cells: Defining reliable markers of pluripotency Theriogenology, 74(4): 516-524 (2010).
Parng et al., Gene conversion contributes to lg light chain diversity in cattle,The Journal of Immunology, 157:5478-5486 (1996).
Perlmann et al., The Rat Immunoglobulin Kapa Light Chain Locus Is on Chromosome 4, Immunoaenetics, 22:97-100 (1985).
Petitte et al., Avian pluripotent stem cells, Mech Dev., 121(9):1159-68 (2004).
Poueymirou, WT et al., F0 generation mice fully derived from gene-targeted embryonic stem cells allowing immediate phenotypic analyses, Nat Biotechnol., 25(1):91-9 (2007).
Precopio et al., Immunization with vaccinia virus induces polyfunctional and phenotypically distinctive CD8(+) T cell responses, J Exp Med, 204(6):1405-1416 (2007).
Qin et al., Systematic Comparison of Constitutive Promoters and the Doxycycline-Inducible Promoter, 5(5): e10611 pp. 1-4. 2010.
Ristevski, S., Making better transgenic models: conditional, temporal, and spatial approaches, Mol Biotechnol., 29(2):153-63 (2005).
Roes, Dr. Jürgen, Declaration Under 37 C.F.R. §1.132, pp. 1-7 (Aug. 2, 2011).
Schelonka et al., Absence of N addition facilitates B cell development, but impairs immune responses, Immunogenetics, 63:599-609 (2011).
Schroeder et al., Developmental regulation of the human antibody repertoire, Ann N Y Acad Sci, 764:242-260 (1995).
Schumacher, TN., T-cell-receptor gene therap,. Nat Rev Immunol., 2(7):512-9 (2002).

(56) References Cited

OTHER PUBLICATIONS

Shankar, B. and Majumdar, S., An Efficient Method for Generation of Transgenic Rats Avoiding Embryo Manipulation, Nucleic Acids; pp. 1-11 (2016).
Skok et al., Reversible contraction by looping of the Tera and Torb loci in rearranging thymocytes, Nat Immunol, 8(4):378-387 (2007).
Sun et al., Immunoglobulin genes and diversity: what we have learned from domestic animals, Journal of Animal Science and Biotechnology, 3(18) pp. 1-5 (2012).
Thai et al., Distinct and opposite activities of human terminal deoxynucleotidyltransferase splice variants, J Immunol, 173(6):4009-4019 (2004).
Thai et al., Distinct and opposite diversifying activities of terminal transferase splice variants, Nat Immunol, 3(5):457-462 (2002).
Thai et al., Isoforms of Terminal Deoxynucleotidyltransferase: Developmental Aspects and Function Advances in Immunology, 86:113-136 (2005).
Tong et al., Production of p53 gene knockout rats by homologous recombination in embryonic stem cells, Nature, 467(9):211-215 (2010).
Troshchynsky, A. et al., Functional analyses of polymorphic variants of human terminal deoxynucleotidyl transferase, Genes and Immunty, 16:388-398 (2015).
Truscott et al., Disulfide bond engineering to trap peptides in the MHC class I binding groove, J Immunol, 178(10):6280-6289 (2007).
U.S. Appl. No. 13/195,951: Declaration of Andrew Murphy, dated Jul. 16, 2014.
Valenzuela, DM, et al., High-throughput engineering of the mouse genome coupled with high-resolution expression analysis, Nat Biotechnol., 21(6):652-9 (2003).
Vettermann, C. et al., Allelic exclusion of immunoglobulin genes: models and mechanisms, Immunological Reviews, 237:22-42 (2010).
Wahlstrom et al., Localization of the rat immunoglobulin lambda light chain locus to chromosome 11, Immunogenetics, 28:182-183 (1988).
Wasserman et al., Down-regulation of terminal deoxynucleotidyl transferase by lg heavy chain in B lineage cells., J Immunol, 158(3):1133-1138 (1997).
West, J. and Gill, W., Genome Editing in Large Animals, Journal of Equine Veterinary Science Journal of Equine Veterinary Science, 41; pp. 1-6 (2016).

\* cited by examiner

NON-HUMAN ANIMALS EXPRESSING EXOGENOUS TERMINAL DEOXYNUCLEOTIDYLTRANSFERASE

RELATED APPLICATIONS

This application is a divisional of U.S. patent application Ser. No. 15/612,625, filed Jun. 2, 2017, which claims the benefit of priority to U.S. Provisional Patent Application Ser. No. 62/345,524, filed Jun. 3, 2016, which applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jul. 12, 2017, is named RPB-013.01_SL.txt and is 7,930 bytes in size.

BACKGROUND

Non-human animals, particularly mice and rats, have proven to be a valuable source of therapeutic antibodies and potentially could serve as a source of other antigen binding molecules. A high level of antigen receptor diversity in such non-human animals increases the likelihood that an antigen binding molecule having desirable therapeutic properties will be generated following immunization. Accordingly, there is a need for genetically engineered non-human animals that have increased antigen receptor diversity to improve production of therapeutic antigen binding molecules.

SUMMARY

In certain aspects, provided herein are genetically modified non-human animals comprising in their genome an exogenous nucleic acid encoding terminal deoxynucleotidyltransferase (TdT), as well as methods of making and using such non-human animals. In some embodiments, the exogenous TdT is human TdT. In some embodiments, the exogenous TdT is of endogenous species origin (e.g., in mice the exogenous TdT has a mouse sequence). In some embodiments, the non-human animals provided herein express the TdT encoded by the exogenous nucleic acid during B cell development, for example, in pro-B cells and/or in pre-B cells. In some embodiments, the non-human animals provided herein express the TdT encoded by the exogenous nucleic acid during T cell development, for example, in double-negative (DN) thymocytes and/or in double-positive (DP) thymocytes. In some embodiments, the genetically modified non-human animal comprises multiple copies of exogenous nucleic acids encoding TdT (e.g., at least 2, 3, 4, 5, 6, 7 or 8 copies). In some embodiments, the genetically modified non-human animal is a mammal, such as a rodent (e.g., a mouse or a rat).

In some embodiments, the genetically modified non-human animal comprises in its genome an immunoglobulin variable region comprising unrearranged human immunoglobulin variable region gene segments (e.g., heavy chain gene segments, κ chain gene segments, λ chain gene segments) operably linked to an immunoglobulin constant region gene (e.g., a heavy chain constant region gene, a κ chain constant region gene, a λ chain constant region gene). In some embodiments, the constant region gene is a human constant region gene, a mouse constant region gene or a rat constant region gene. In some embodiments, the constant region gene is of endogenous species origin. In some embodiments, the variable region and the constant region gene are located in an endogenous immunoglobulin locus (e.g., a heavy chain locus, a κ locus, a λ locus). In some embodiments, the genetically modified non-human organism expresses antibodies comprising a human immunoglobulin variable domain derived from the immunoglobulin variable region and an immunoglobulin constant domain encoded by the immunoglobulin constant region gene. In some embodiments, provided herein are methods of using such a genetically modified non-human animal to generate an antibody, a B cell, a hybridoma or a nucleic acid encoding a human immunoglobulin variable domain.

In certain embodiments, the genetically modified non-human animal comprises in its genome a T cell receptor (TCR) variable region comprising unrearranged human TCR variable region gene segments (e.g., TCRα gene segments, TCR β gene segments, TCRγ gene segments, TCRδ gene segments) operably linked to a TCR constant region gene (e.g., TCRα constant region gene, TCR β constant region gene, TCRγ constant region gene, TCRδ constant region gene). In some embodiments, the constant region gene is a human constant region gene, a mouse constant region gene or a rat constant region gene. In some embodiments, the constant region gene is of endogenous species origin. In some embodiments, the variable region and the constant region gene are located in an endogenous TCR locus (e.g., TCRα locus, TCR β locus, TCRγ locus, TCRδ locus). In some embodiments, the genetically modified non-human organism expresses TCR comprising a human TCR variable domain derived from the TCR variable region and a TCR constant domain encoded by the TCR constant region gene. In some embodiments, provided herein are methods of using such a genetically modified non-human animal to generate a TCR, a T cell, a T cell hybridoma or a nucleic acid encoding a human TCR variable domain.

In some embodiments, the genetically modified non-human animal comprises in its genome an immunoglobulin variable region comprising unrearranged human immunoglobulin variable region gene segments (e.g., heavy chain gene segments, κ chain gene segments, λ chain gene segments) operably linked to a TCR constant region gene (e.g., TCRα constant region gene, TCR β constant region gene, TCRγ constant region gene, TCRδ constant region gene). In some embodiments, the constant region gene is a human constant region gene, a mouse constant region gene or a rat constant region gene. In some embodiments, the constant region gene is of endogenous species origin. In some embodiments, the variable region and the constant region gene are located in an endogenous TCR locus (e.g., TCRα locus, TCR β locus, TCRγ locus, TCRδ locus). In some embodiments, the genetically modified non-human organism expresses chimeric antigen receptor (CAR) comprising a human immunoglobulin variable domain derived from the immunoglobulin variable region and a TCR constant domain encoded by the TCR constant region gene. In some embodiments, provided herein are methods of using such a genetically modified non-human animal to generate an CAR, a T cell, a T cell hybridoma or a nucleic acid encoding a human immunoglobulin variable domain.

In some embodiments, provided herein are methods of making a non-human animal disclosed herein comprising engineering the non-human animal to comprise in its germline the genetic modifications described herein. In some embodiments, provided herein are non-human ES cells comprising the genetic modifications described herein.

DETAILED DESCRIPTION

General

Figure 1:
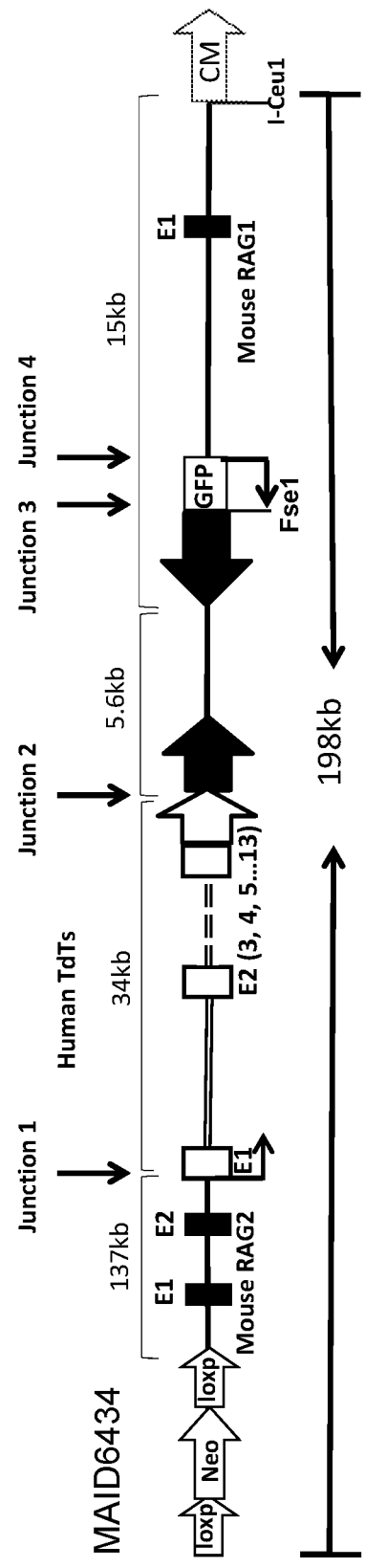
FIG. 1 depicts a diagram of an exemplary targeting vector (not to scale) whereas part of the mouse Rag2 gene is replaced with a DNA sequence encoding short isoform human TdT (hTdTs). In exemplary embodiments, the vector is randomly integrated into the genome. Unless labeling in the diagram suggests otherwise (e.g., as for selection cassettes, loxP sites, etc.), filled shapes and single lines represent mouse sequences, and empty shapes and double lines represent human sequences. E1, E2, etc. represent exons of particular illustrated genes, GFP is green fluorescent protein, CM is chloramphenicol resistant gene, neo is neomycin resistant gene. Junctions 1-4 correspond to junctions indicated in Table 1.

Provided herein are methods and compositions related to non-human animals comprising in their genome an exogenous nucleic acid encoding TdT (e.g., human, mouse or rat TdT). In some embodiments, the genetically modified non-human animal is a mammal, such as a rodent (e.g., a mouse or a rat). In certain embodiments, the genome of the non-human animal comprises further modifications such that it expresses antigen binding molecules having human variable domains (e.g., antibodies, TCRs and/or CARs).

TdT is a DNA polymerase that catalyzes template-independent addition of nucleotides (N-additions) during junction formation in V(D)J recombination, which leads to an increase in antigen-receptor diversity in B and T lymphocytes. In some embodiments, the non-human animals provided herein express increased levels of TdT during B cell development and/or T cell development compared to corresponding non-human animals (i.e., non-human animals of the same species and strain) that do not include in their genome an exogenous nucleic acid encoding TdT. In some embodiments, the non-human animals provided herein express TdT during stages of B cell development and/or T cell development during which corresponding non-human animals that do not include in their genome an exogenous nucleic acid encoding TdT do not express TdT (e.g., during the pre-B cell stage). In some embodiments, the genetically modified non-human animals described herein have increased antigen-receptor diversity (e.g., antibody diversity, TCR diversity and/or CAR diversity) compared to corresponding non-human animals that do not include in their genome an exogenous nucleic acid encoding TdT.

Definitions

The articles "a" and "an" are used herein to refer to one or to more than one (i.e., to at least one) of the grammatical object of the article. By way of example, "an element" means one element or more than one element.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof amino acid analogs having variant side chains; and all stereoisomers of any of the foregoing.

As used herein, the term "antibody" may refer to both an intact antibody and an antigen binding fragment thereof. Intact antibodies are glycoproteins that include at least two heavy (H) chains and two light (L) chains inter-connected by disulfide bonds. Each heavy chain includes a heavy chain variable region (abbreviated herein as $V_H$) and a heavy chain constant region. Each light chain includes a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The term "antibody" also includes single domain antibodies, heavy chain only antibodies, antibodies with light chain variable gene segments on heavy chain, etc.

The terms "antigen binding fragment" and "antigen-binding portion" of an antigen binding molecule (e.g., an antibody, a T cell receptor (TCR), a chimeric antigen receptor (CAR)), as used herein, refers to one or more fragments of the antigen binding molecule that retain the ability to bind to an antigen. An antigen binding fragment can include any antibody, TCR or CAR fragment that retains at least a portion of the variable region of an intact antigen binding molecule and is capable of binding to an antigen. Examples of binding fragments encompassed within the term "antigen binding fragment" include, but are not limited to Fab, Fab', F(ab)$_2$, Fv, scFv, disulfide linked Fv, Fd, single-chain antibodies, soluble TCR, single-chain TCR, soluble CAR, single-chain CAR, isolated CDRH3 (antibody or TCR), and other antigen binding fragments that retain at least a portion of the variable region of an intact antigen binding molecule. These antigen binding fragments can be obtained using conventional recombinant and/or enzymatic techniques and can be screened for antigen binding in the same manner as intact antibodies.

The term "corresponding" in reference to a non-human animal, is used to describe the features of a control non-human animal of the same species and comprising the same genetic modifications as a subject non-human except that the subject non-human animal expresses exogenous TdT whereas the corresponding non-human animal does not.

As used herein, a "chimeric antigen receptor" or "CAR" refers to an antigen binding protein in that includes an immunoglobulin antigen binding domain (e.g., an immunoglobulin variable domain) and a T cell receptor (TCR) constant domain or a portion thereof. As used herein, a "constant domain" of a TCR polypeptide includes a membrane-proximal TCR constant domain, and may also include a TCR transmembrane domain and/or a TCR cytoplasmic tail. For example, in some embodiments, the CAR is a dimer that includes a first polypeptide comprising an immunoglobulin heavy chain variable domain linked to a TCRβ constant domain and a second polypeptide comprising an immunoglobulin light chain variable domain (e.g., a κ or λ variable domain) linked to a TCRα constant domain. In some embodiments, the CAR is a dimer that includes a first polypeptide comprising an immunoglobulin heavy chain variable domain linked to a TCRα constant domain and a second polypeptide comprising an immunoglobulin light chain variable domain (e.g., a κ or λ variable domain) linked to a TCRβ constant domain.

The phrase "derived from" when used concerning a rearranged variable region gene or a variable domain "derived from" an unrearranged variable region and/or unrearranged variable region gene segments refers to the ability to trace the sequence of the rearranged variable region gene or variable domain back to a set of unrearranged variable region gene segments that were rearranged to form the rearranged variable region gene that expresses the variable domain (accounting for, where applicable, splice differences and somatic mutations). For example, a rearranged variable region gene that has undergone somatic mutation does not change the fact that it is derived from the unrearranged variable region gene segments.

As used herein, the term "locus" refers to a region on a chromosome that contains a set of related genetic elements (e.g., genes, gene segments, regulatory elements). For example, an unrearranged immunoglobulin locus may include immunoglobulin variable region gene segments, one or more immunoglobulin constant region genes and associated regulatory elements (e.g., promoters, enhancers, switch elements, etc.) that direct V(D)J recombination and immunoglobulin expression, while an unrearranged TCR locus may include TCR variable region gene segments, a TCR constant region gene and associated regulatory elements (e.g., promoters, enhancers, etc.) that direct V(D)J recombination and TCR expression. Similarly, an unrearranged CAR locus may include immunoglobulin variable region gene segments, a TCR constant region gene and associated regulatory elements (e.g., promoters, enhancers, etc.) that direct V(D)J recombination and CAR expression. A locus can be endogenous or non-endogenous. The term "endogenous locus" refers to a location on a chromosome at which a particular genetic element is naturally found.

Unrearranged variable region gene segments are "operably linked" to a contiguous constant region gene if the unrearranged variable region gene segments are capable of rearranging to form a rearranged variable region gene that is expressed in conjunction with the constant region gene as a polypeptide chain of an antigen binding protein.

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

As used herein, "specific binding" and "antigen specificity" refers to the ability of an antigen binding molecule (e.g., an antibody, a TCR, a CAR) to bind to a predetermined target, such as a predetermined antigen. Typically, an antigen binding molecule specifically binds to its predetermined target with an affinity corresponding to a $K_D$ of about $10^{-7}$ M or less, and binds to the predetermined target with an affinity corresponding to $K_D$ that is at least 10 fold less, at least 100 fold less or at least 1000 fold less than its $K_D$ for a non-specific and unrelated target (e.g., BSA, casein). In some embodiments, an antigen binding molecule specifically binds to its predetermined target with an affinity corresponding to a $K_D$ of about $10^{-8}$ M or less, $10^{-9}$M or less or $10^{-19}$ M or less.

As used herein, a "T cell receptor" or "TCR" refers to an antigen binding protein in that includes both a TCR antigen binding domain (e.g., a TCR variable domain) and at least a portion of a TCR constant domain. As used herein, a "constant domain" of a TCR polypeptide includes a membrane-proximal TCR constant domain, and may also include a TCR transmembrane domain and/or a TCR cytoplasmic tail. In certain embodiments, the TCR is a soluble TCR and does not include a TCR transmembrane domain or a TCR cytoplasmic tail. For example, in some embodiments, the TCR is a dimer that includes a first polypeptide comprising a TCRβ variable domain linked to a TCRβ constant domain (or a fragment thereof) and a second polypeptide comprising a TCRα linked to a TCRα constant domain (or a fragment thereof).

The term "unrearranged" includes the state of an immunoglobulin, TCR or CAR variable region locus or variable region gene segments wherein V gene segments and J gene segments (for heavy or TCRβ variable regions, D gene segments as well) are maintained separately but are capable of being joined to form a rearranged V(D)J gene (a "variable region gene") that comprises a single V, (D), J of the V(D)J repertoire.

Genetically Modified Non-Human Animals and ES Cells

In certain aspects, provided herein are non-human animals and ES cells comprising in their genome an exogenous nucleic acid encoding TdT (e.g., human, mouse or rat TdT). In certain embodiments, the genome of the non-human animals and ES cells comprise further modifications including, for example, modifications that result in the expression of antigen binding molecules having human variable domains (e.g., antibodies, TCRs and/or CARs).

The genetically modified non-human animals and ES cells provided herein can be generated using any appropriate method known in the art. For example, non-human animal ES cells containing targeted genetic modifications can be generated using VELOCIGENE® technology, which is described in U.S. Pat. Nos. 6,586,251, 6,596,541, 7,105,348, and Valenzuela et al. (2003) "High-throughput engineering of the mouse genome coupled with high-resolution expression analysis" Nat. Biotech. 21(6): 652-659, and U.S. Pat. Pub. No. US 2014/0310828, each of which is hereby incorporated by reference. Targeted modifications can also be made using a CRISPR/Cas system, as described, for example, in U.S. Pat. No. 9,228,208, and U.S. Pub. Nos. US 2015-0159174 A1, US 2016-0060657 A1, US 2015-0376650 A1, US 2015-0376651 A1, US 2016-0046960 A1, US 2015-0376628 A1, and US 2016-0115486 A1, each of which is incorporated by reference. Targeted modifications can also be made using a meganuclease, as described, for example, in U.S. Pat. Nos. 8,703,485, 8,530,214 and 8,624,000, each of which is hereby incorporated by reference in its entirety. Non-targeted genetic modifications can be made using standard methods in the art, including, for example, as described in U.S. Pat. Nos. 6,150,584, 6,114,598, 5,633,425, 7,501,552, 6,235,883, 6,998,514 and 5,776,773, each of which are hereby incorporated by reference in its entirety.

ES cells described herein can then be used to generate a non-human animal using methods known in the art. For example, the mouse non-human animal ES cells described herein can be used to generate genetically modified mice using the VELOCIMOUSE® method, as described in U.S. Pat. No. 7,294,754 and Poueymirou et al., Nature Biotech 25:91-99 (2007), each of which is hereby incorporated by reference. Rat ES cells can be used to generate modified rats using the method described, e.g., U.S. Pat. Pub. No. US 2014/0310828, incorporated herein by reference. Resulting mice or rats can be bread to homozygosity. Multiple distinct modifications can be combined in a single genetically modified organism either by breeding of separately modified animals or by introducing additional modifications into an already modified ES cell (e.g., using the methods described herein).

In some embodiments, the non-human animal can be any non-human animal. In some embodiments, the non-human animal is a vertebrate. In some embodiments, the non-human animal is a mammal. In some embodiments, the genetically modified non-human animal described herein may be selected from a group consisting of a mouse, rat, rabbit, pig, bovine (e.g., cow, bull, buffalo), deer, sheep, goat, llama, chicken, cat, dog, ferret, primate (e.g., marmoset, rhesus monkey). For non-human animals where suitable genetically modifiable ES cells are not readily available, other methods can be employed to make a non-human animal comprising the genetic modifications described herein. Such methods include, for example, modifying a non-ES cell genome (e.g., a fibroblast or an induced pluripotent cell) and employing nuclear transfer to transfer the modified genome to a suitable cell, such as an oocyte, and gestating the modified cell (e.g., the modified oocyte) in a non-human animal under suitable conditions to form an embryo.

In some embodiments, the non-human animal is a mammal. In some embodiments, the non-human animal is a small mammal, e.g., of the superfamily Dipodoidea or Muroidea. In some embodiments, the non-human animal is a rodent. In certain embodiments, the rodent is a mouse, a rat or a hamster. In some embodiments, the rodent is selected from the superfamily Muroidea. In some embodiments, the non-human animal is from a family selected from Calomyscidae (e.g., mouse-like hamsters), Cricetidae (e.g., hamster, New World rats and mice, voles), Muridae (e.g., true mice and rats, gerbils, spiny mice, crested rats), Nesomyidae (e.g., climbing mice, rock mice, white-tailed rats, Malagasy rats and mice), Platacanthomyidae (e.g., spiny dormice), and Spalacidae (e.g., mole rats, bamboo rats, and zokors). In some embodiments, the rodent is selected from a true mouse or rat (family Muridae), a gerbil, a spiny mouse, and a crested rat. In some embodiments, the mouse is from a member of the family Muridae. In some embodiments, the non-human animal is a rodent. In some embodiments, the rodent is selected from a mouse and a rat. In some embodiments, the non-human animal is a mouse.

In some embodiments, the non-human animal is a mouse of a C57BL strain. In some embodiments, the C57BL strain is selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the non-human animal is a mouse of a 129 strain. In some embodiments, the 129 strain is selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. In some embodiments, the genetically modified mouse is a mix of a 129 strain and a C57BL strain. In some embodiments, the mouse is a mix of 129 strains and/or a mix of C57BL/6 strains. In some embodiments, the 129 strain of the mix is a 129S6 (129/SvEvTac) strain. In some embodiments, the mouse is a BALB strain (e.g., BALB/c). In some embodiments, the mouse is a mix of a BALB strain and another strain (e.g., a C57BL strain and/or a 129 strain). In some embodiments, the non-human animals provided herein can be a mouse derived from any combination of the aforementioned strains.

In some embodiments, the non-human animal provided herein is a rat. In some embodiments, the rat is selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

Non-Human Animals Expressing Exogenous TdT

In certain aspects, provided herein are genetically modified non-human animals and ES cells comprising in their germline and/or genome a nucleic acid sequence encoding an exogenous Terminal Deoxynucleotidyltransferase (TdT). Deoxynucleotidyltransferase (TdT) is a DNA polymerase that catalyzes template-independent addition of nucleotides (NP-additions) during junction formation in V(D)J recombination, which leads to an increase in antigen-receptor diversity in B and T lymphocytes. Template-independent additions, non-template additions, and non-germline additions all refer to nucleotide additions catalyzed by TdT, and these terms are used herein interchangeably.

In certain embodiments, the sequence of the exogenous TdT in the genome of the genetically modified non-human animal can be from any animal that encodes a TdT or a TdT orthologue. In some embodiments, the TdT is a vertebrate TdT. In some embodiments, the TdT is a mammalian TdT. In some embodiments, the TdT is from a mammal selected from a group consisting of a mouse, rat, rabbit, pig, bovine (e.g., cow, bull, buffalo), deer, sheep, goat, llama, chicken, cat, dog, ferret, primate (e.g., marmoset, rhesus monkey) or human. In some embodiments, the TdT is of endogenous species origin (i.e., the TdT sequence is that of the same species as the genetically modified non-human animal). In some embodiments, the TdT is human TdT, mouse TdT or rat TdT. In some embodiments, the nucleic acid sequence is the genomic TdT sequence (i.e., including exons and introns). In some embodiments, the nucleic acid sequence encodes TdT mRNA/cDNA (i.e., the exons of one or more TdT isoforms).

Human TdT (hTdT) is encoded by the DNTT gene, which is located on human chromosome 10. An exemplary genomic DNA sequences of hTdT can be found at position 96304328 to 96338564 of NCBI accession number NC_000010.11, which is hereby incorporated by reference. Exemplary mRNA sequence of isoforms of hTdT is provided by NCBI accession numbers NM_001017520.1 and NM_004088.3, each of which is hereby incorporated by reference. The protein sequences encoded by these isoforms is provided by NCBI accession numbers NP_001017520.1 and NP_004079.3, respectively, each of which is hereby incorporated by reference. Among the TdT isoforms is a short isoform (hTdTS) and two long isoforms (hTdTL1 and hTdTL2). The sequences of the three isoforms are provided, for example, in Thai and Kearney, *Adv. Immunol.* 86:113-36 (2005), which is hereby incorporated by reference. In certain embodiments the exogenous nucleic acid sequence encodes hTdTS. In some embodiments, the exogenous nucleic acid sequence encodes hTdTL1. In some embodiments, the exogenous nucleic acid sequence encodes hTdTL2. In certain embodiments, the non-human organism comprises exogenous nucleic acid sequences encoding multiple isoforms (e.g., both hTdTS and hTdTL2). In certain embodiments, the non-human organism comprises exogenous nucleic acid sequences encoding all three human isoforms (e.g., both hTdTS and hTdTL2).

Mouse TdT (mTdT) is encoded by the Dntt gene, which is located on mouse chromosome 19. An exemplary genomic DNA sequence of mTdT can be found at position 41029275 to 41059525 of NCBI accession number NC_000085.6, which is hereby incorporated by reference. Exemplary mRNA sequences of isoforms of mTdT is provided by NCBI accession numbers NM_001043228.1 and NM_009345.2, each of which is hereby incorporated by reference. The protein sequences encoded by these isoforms is provided by NCBI accession numbers NP_001036693.1 and NP_033371.2, respectively, each of which is hereby incorporated by reference.

Rat TdT (rTdT) is encoded by the Dntt gene, which is located on rat chromosome 1. An exemplary genomic DNA sequence of rTdT can be found at position 260289626 to 260321174 of NCBI accession number NC_005100.4, which is hereby incorporated by reference. An exemplary mRNA sequence of rTdT is provided by NCBI accession number NM_001012461.1, which is hereby incorporated by reference. The protein sequence encoded by this mRNA is provided by NCBI accession number NP_001012479.1, which is hereby incorporated by reference.

In some embodiments, the genome of the genetically modified non-human animal contains multiple copies of the nucleic acid sequence encoding the exogenous TdT. In some embodiments, the genetically modified non-human animal contains 2, 3, 4, 5, 6, 7, 8, 9, 10, 11, 12, 13, 14, 15, 16, 17, 18, 19 or 20 copies of the nucleic acid sequence encoding the exogenous TdT. In some embodiments, the genetically modified non-human animal contains at least 2, 3, 4, 5, 6, 7, 8, 9, 10, 11, 12, 13, 14, 15, 16, 17, 18, 19 or 20 copies of the nucleic acid sequence encoding the exogenous TdT.

In some embodiments, the nucleic acid sequence encoding the exogenous TdT is operably linked to one or more transcriptional control element (e.g., a promoter and/or an enhancer). In some embodiments, the transcriptional control element is a constitutive (i.e., ubiquitous) promoter. Examples of constitutive promoters include, but are not limited to, a SV40, a CMV promoter, an adenoviral promoter, an EF1 promoter, a β-actin promoter, an EGR1 promoter, an eIF4A1 promoter, a FerH promoter, a FerL promoter, a GAPDH promoter, a GRP78 promoter, a GRP94 promoter, a HSP70 promoter, a β-Kin promoter, a PGK-1 promoter, a ROSA promoter and an Ubiquitin B promoter. In some embodiments, the nucleic acid sequence is not operably linked to a constitutive promoter.

In some embodiments, the transcriptional control element induces expression of the encoded TdT during B cell development. In some embodiments, the transcriptional control element induces expression of TdT in pro-B cells and/or pre-B cells. In some embodiments, the transcriptional control element is a transcriptional control element (e.g., a promoter and/or enhancer) of a gene expressed during B cell development, in pro-B cells and/or in pre-B cells. In some embodiments, the transcriptional control element is a RAG1 transcriptional control element, a RAG2 transcriptional control element, an immunoglobulin heavy chain transcriptional control element, an immunoglobulin κ light chain transcriptional control element and/or an immunoglobulin λ light chain transcriptional control element. In some embodiment, the transcriptional control element is of endogenous species origin. In some embodiments, the transcriptional control element is a mouse transcriptional control element, a rat transcriptional control element or a human transcriptional control element. In some embodiments, the transcriptional control element is an endogenous transcriptional control element (e.g., the nucleotide sequence encoding the exogenous TdT is inserted into the non-human animal's genome at a position such that expression of the exogenous TdT is at least partially controlled by an endogenous transcriptional control element). In some embodiments, transcriptional control elements may include those regulating transcription of: RAG1, RAG2, λ5, VpreB, CD34, CD45, AA4.1, CD45R, IL-7R, MHC class II, CD10, CD19, CD38, CD20, CD40, various immunoglobulin light and heavy chain V gene segments promoters and enhancers (see. e.g., a list of various V gene segments listed on the International Immunogenetics Information System® website—IMGT, imgt.org, e.g., mouse $V_H$1-72 promoter and others, etc.). Transcriptional control elements may include those of human, mouse, rat, or other species origin.

In some embodiments, the transcriptional control element induces expression of the encoded TdT during T cell development. In some embodiments, the transcriptional control element induces expression of TdT in CD4/CD8 double-negative (DN) thymocytes and/or CD4/CD8 double-positive (DP) thymocytes. In some embodiments, the transcriptional control element is a transcriptional control element (e.g., a promoter and/or enhancer) of a gene expressed during T cell development, in DN thymocytes and/or in DP thymocytes. In some embodiments, the transcriptional control element is a RAG1 transcriptional control element, a RAG2 transcriptional control element, a TCRα transcriptional control element, a TCRβ transcriptional control element, a TCRγ transcriptional control element and/or a TCRδ transcriptional control element. In some embodiment, the transcriptional control element is of endogenous species origin. In some embodiments, the transcriptional control element is a mouse transcriptional control element, a rat transcriptional control element or a human transcriptional control element. In some embodiments, the transcriptional control element is an endogenous transcriptional control element (e.g., the nucleotide sequence encoding the exogenous TdT is inserted into the non-human animal's genome at a position such that expression of the exogenous TdT is at least partially controlled by an endogenous transcriptional control element). In some embodiments, transcriptional control elements may include those regulating transcription of: RAG1, RAG2, Lck, ZAP-70, CD34, CD2, HSA, CD44, CD25, PTα, CD4, CD8, CD69, various TCRα, TCRβ, TCRδ, and TCRγ V gene segments promoters and enhancers (see. e.g., a list of various V gene segments listed on the International Immunogenetics Information System® website—IMGT, imgt.org, etc.) Transcriptional control elements may include those of human, mouse, rat, or other species origin.

In some embodiments, the nucleic acid encoding the TdT is located in the genome of the non-human animal at or proximal to (e.g., within 1, 2, 3, 4, 5, 6, 7, 8, 9, 10, 20, 30, 40, 50, 60, 70, 80, 90 or 100 kb) a genomic locus of a gene that is expressed during B cell development, in pro-B cells and/or in pre-B cells. In some embodiments, the nucleic acid sequence encoding TdT is located at or proximal to an immunoglobulin κ light chain locus, an immunoglobulin λ light chain locus, an immunoglobulin heavy chain locus, a RAG1 locus or a RAG2 locus.

In some embodiments, the nucleic acid encoding the TdT is located in the genome of the non-human animal at or proximal to (e.g., within 1, 2, 3, 4, 5, 6, 7, 8, 9, 10, 20, 30, 40, 50, 60, 70, 80, 90 or 100 kb) a genomic locus of a gene that is expressed during T cell development, in DN thymocytes and/or in DP thymocytes. In some embodiments, the nucleic acid sequence encoding TdT is located at or proximal to a TCRα chain locus, a TCRβ chain locus, a TCRγ chain locus, a TCRδ chain locus, a RAG1 locus or a RAG2 locus.

In some embodiments, the non-human animal provided herein expresses elevated levels of TdT expression during one or more stages to T cell and/or B cell development (e.g., in pro-B cells, in pre-B cells, in DN thymocytes and/or in DP thymocytes) compared to a corresponding non-human animal that does not have a nucleic acid encoding an exogenous TdT in its genome. In some embodiments, the genetically modified non-human animals provided herein express at least 10%, 20%, 30%, 40%, 50%, 60%, 70%, 80%, 90%, 100% 150%, 200%, 250%, 300%, 350%, 400%, 450% or 500% more TdT in one or more stages of T cell and/or B cell development than a corresponding non-human animal.

In some embodiments, the non-human animal provided herein has a greater percentage of V-J immunoglobulin κ chain junctions containing non-template additions than a corresponding non-human animal that does not have a nucleic acid encoding an exogenous TdT in its genome. In some embodiments, the percentage of V-J immunoglobulin κ chain junctions containing non-template additions in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-J immunoglobulin κ chain junctions not containing non-template additions than a corresponding non-human animal that does not have a nucleic acid encoding an exogenous TdT in its genome. In some embodiments, the percentage of V-J immunoglobulin κ chain junctions not containing non-template additions in the genetically modified non-human animals provided herein is less than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin κ chain junctions containing at least 1 N-addition than a corresponding non-human animal that does not have a nucleic acid encoding an exogenous TdT in its genome. In some embodiments, the percentage of V-J immunoglobulin κ chain junctions containing at least 1 N-addition in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin κ chain junctions containing at least 2 N-additions than a corresponding non-human animal that does not have a nucleic acid encoding an exogenous TdT in its genome. In some embodiments, the percentage of V-J immunoglobulin κ chain junctions containing at least 2 N-additions in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin κ chain junctions containing at least 3 N-additions than a corresponding non-human animal that does not have a nucleic acid encoding an exogenous TdT in its genome. In some embodiments, the percentage of V-J immunoglobulin κ chain junctions containing at least 3 N-additions in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin κ chain junctions containing at least 4 N-additions than a corresponding non-human animal that does not have a nucleic acid encoding an exogenous TdT in its genome. In some embodiments, the percentage of V-J immunoglobulin κ chain junctions containing at least 4 N-additions in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-J immunoglobulin κ chain junctions in the animal comprise non-template additions. In some embodiments, the non-human animal has a greater frequency of unique immunoglobulin κ chain CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%. In some embodiments, the non-human animal provided herein has at least 900, 1000, 1100, 1200, 1300, 1400, 1500 or 1700 unique immunoglobulin κ chain CDR3 sequences per 10,000 immunoglobulin κ chain CDR3 sequences.

In some embodiments, the non-human animal provided herein has a greater percentage of V-J immunoglobulin λ chain junctions containing non-template additions than a corresponding non-human animal that does not have a nucleic acid encoding an exogenous TdT in its genome. In some embodiments, the percentage of V-J immunoglobulin λ chain junctions containing non-template additions in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-J immunoglobulin λ chain junctions not containing non-template additions than a corresponding non-human animal that does not have a nucleic acid encoding an exogenous TdT in its genome. In some embodiments, the percentage of V-J immunoglobulin λ chain junctions not containing non-template additions in the genetically modified non-human animals provided herein is less than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin λ chain junctions containing at least 1 N-addition than a corresponding non-human animal that does not have a nucleic acid encoding an exogenous TdT in its genome. In some embodiments, the percentage of V-J immunoglobulin λ chain junctions containing at least 1 N-addition in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin λ chain junctions containing at least 2 N-additions than a corresponding non-human animal that does not have a nucleic acid encoding an exogenous TdT in its genome. In some embodiments, the percentage of V-J immunoglobulin λ chain junctions containing at least 2 N-additions in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin λ chain junctions containing at least 3 N-additions than a corresponding non-human animal that does not have a nucleic acid encoding an exogenous TdT in its genome. In some embodiments, the percentage of V-J immunoglobulin λ chain junctions containing at least 3 N-additions in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin λ chain junctions containing at least 4 N-additions than a corresponding non-human animal that does not have a nucleic acid encoding an exogenous TdT in its genome. In some embodiments, the percentage of V-J immunoglobulin λ chain junctions containing at least 4 N-additions in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-J immunoglobulin λ chain junctions in the animal comprise non-template additions. In some embodiments, the non-human animal has a greater frequency of unique immunoglobulin λ chain CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%. In some embodiments, the non-human animal provided herein has at least 150, 160, 170, 180, 190, 200, 210, 220, 230, 240, 250, 260, 270, 280, 290 or 300 unique immunoglobulin λ chain CDR3 sequences per 10,000 immunoglobulin λ chain CDR3 sequences.

In some embodiments, the non-human animal provided herein has a greater percentage of V-D immunoglobulin heavy chain junctions containing non-template additions than a corresponding non-human animal that does not have a nucleic acid encoding an exogenous TdT in its genome. In some embodiments, the percentage of V-D immunoglobulin heavy chain junctions containing non-template additions in the genetically modified non-human animals provided herein is greater than percentage of V-D immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-D immunoglobulin heavy chain junctions not containing non-template additions than a corresponding non-human animal that does not have a nucleic acid encoding an exogenous TdT in its genome. In some embodiments, the percentage of V-D immunoglobulin heavy chain junctions not containing non-template additions in the genetically modified non-human animals provided herein is less than percentage of V-D immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D immunoglobulin heavy chain junctions containing at least 1 N-addition than a corresponding non-human animal that does not have a nucleic acid encoding an exogenous TdT in its genome. In some embodiments, the percentage of V-D immunoglobulin heavy chain junctions containing at least 1 N-addition in the genetically modified non-human animals provided herein is greater than percentage of V-D immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D immunoglobulin heavy chain junctions containing at least 2 N-additions than a corresponding non-human animal that does not have a nucleic acid encoding an exogenous TdT in its genome. In some embodiments, the percentage of V-D immunoglobulin heavy chain junctions containing at least 2 N-additions in the genetically modified non-human animals provided herein is greater than percentage of V-D immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D immunoglobulin heavy chain junctions containing at least 3 N-additions than a corresponding non-human animal that does not have a nucleic acid encoding an exogenous TdT in its genome. In some embodiments, the percentage of V-D immunoglobulin heavy chain junctions containing at least 3 N-additions in the genetically modified non-human animals provided herein is greater than percentage of V-D immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D immunoglobulin heavy chain junctions containing at least 4 N-additions than a corresponding non-human animal that does not have a nucleic acid encoding an exogenous TdT in its genome. In some embodiments, the percentage of V-D immunoglobulin heavy chain junctions containing at least 4 N-additions in the genetically modified non-human animals provided herein is greater than percentage of V-D immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-D immunoglobulin heavy chain junctions in the animal comprise non-template additions. In some embodiments, the non-human animal has a greater frequency of unique immunoglobulin heavy chain CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%.

In some embodiments, the non-human animal provided herein has a greater percentage of D-J immunoglobulin heavy chain junctions containing non-template additions than a corresponding non-human animal that does not have a nucleic acid encoding an exogenous TdT in its genome. In some embodiments, the percentage of D-J immunoglobulin heavy chain junctions containing non-template additions in the genetically modified non-human animals provided herein is greater than percentage of D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of D-J immunoglobulin heavy chain junctions not containing non-template additions than a corresponding non-human animal that does not have a nucleic acid encoding an exogenous TdT in its genome. In some embodiments, the percentage of D-J immunoglobulin heavy chain junctions not containing non-template additions in the genetically modified non-human animals provided herein is less than percentage of D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of D-J immunoglobulin heavy chain junctions containing at least 1 N-addition than a corresponding non-human animal that does not have a nucleic acid encoding an exogenous TdT in its genome. In some embodiments, the percentage of D-J immunoglobulin heavy chain junctions containing at least 1 N-addition in the genetically modified non-human animals provided herein is greater than percentage of D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of D-J immunoglobulin heavy chain junctions containing at least 2 N-additions than a corresponding non-human animal that does not have a nucleic acid encoding an exogenous TdT in its genome. In some embodiments, the percentage of D-J immunoglobulin heavy chain junctions containing at least 2

N-additions in the genetically modified non-human animals provided herein is greater than percentage of D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of D-J immunoglobulin heavy chain junctions containing at least 3 N-additions than a corresponding non-human animal that does not have a nucleic acid encoding an exogenous TdT in its genome. In some embodiments, the percentage of D-J immunoglobulin heavy chain junctions containing at least 3 N-additions in the genetically modified non-human animals provided herein is greater than percentage of D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of D-J immunoglobulin heavy chain junctions containing at least 4 N-additions than a corresponding non-human animal that does not have a nucleic acid encoding an exogenous TdT in its genome. In some embodiments, the percentage of D-J immunoglobulin heavy chain junctions containing at least 4 N-additions in the genetically modified non-human animals provided herein is greater than percentage of D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the D-J immunoglobulin heavy chain junctions in the animal comprise non-template additions.

In some embodiments, the non-human animal provided herein has a greater percentage of V-J TCRα chain junctions containing non-template additions than a corresponding non-human animal that does not have a nucleic acid encoding an exogenous TdT in its genome. In some embodiments, the percentage of V-J TCRα chain junctions containing non-template additions in the genetically modified non-human animals provided herein is greater than percentage of V-J TCRα chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-J TCRα chain junctions not containing non-template additions than a corresponding non-human animal that does not have a nucleic acid encoding an exogenous TdT in its genome. In some embodiments, the percentage of V-J TCRα chain junctions not containing non-template additions in the genetically modified non-human animals provided herein is less than percentage of V-J TCRα chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRα chain junctions containing at least 1 N-addition than a corresponding non-human animal that does not have a nucleic acid encoding an exogenous TdT in its genome. In some embodiments, the percentage of V-J TCRα chain junctions containing at least 1 N-addition in the genetically modified non-human animals provided herein is greater than percentage of V-J TCRα chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRα chain junctions containing at least 2 N-additions than a corresponding non-human animal that does not have a nucleic acid encoding an exogenous TdT in its genome. In some embodiments, the percentage of V-J TCRα chain junctions containing at least 2 N-additions in the genetically modified non-human animals provided herein is greater than percentage of V-J TCRα chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRα chain junctions containing at least 3 N-additions than a corresponding non-human animal that does not have a nucleic acid encoding an exogenous TdT in its genome. In some embodiments, the percentage of V-J TCRα chain junctions containing at least 3 N-additions in the genetically modified non-human animals provided herein is greater than percentage of V-J TCRα chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRα chain junctions containing at least 4 N-additions than a corresponding non-human animal that does not have a nucleic acid encoding an exogenous TdT in its genome. In some embodiments, the percentage of V-J TCRα chain junctions containing at least 4 N-additions in the genetically modified non-human animals provided herein is greater than percentage of V-J TCRα chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-J TCRα chain junctions in the animal comprise non-template additions. In some embodiments, the non-human animal has a greater frequency of unique TCRα CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%.

In some embodiments, the non-human animal provided herein has a greater percentage of V-D TCRβ chain junctions containing non-template additions than a corresponding non-human animal that does not have a nucleic acid encoding an exogenous TdT in its genome. In some embodiments, the percentage of V-D TCRβ chain junctions containing non-template additions in the genetically modified non-human animals provided herein is greater than percentage of V-D TCRβ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-D TCRβ chain junctions not containing non-template additions than a corresponding non-human animal that does not have a nucleic acid encoding an exogenous TdT in its genome. In some embodiments, the percentage of V-D TCRβ chain junctions not containing non-template additions in the genetically modified non-human animals provided herein is less than percentage of V-D TCRβ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D TCRβ chain junctions containing at least 1 N-addition than a corresponding non-human animal that does not have a nucleic acid encoding an exogenous TdT in its genome. In some embodiments, the percentage of V-D TCRβ chain junctions containing at least 1 N-addition in the genetically modified non-human animals provided herein is greater than percentage of V-D TCRβ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D TCRβ chain junctions containing at least 2 N-additions than a corresponding non-human animal that does not have a nucleic acid encoding an exogenous TdT in its genome. In some embodiments, the percentage of V-D TCRβ chain junctions containing at least 2 N-additions in the genetically modified non-human animals provided herein is greater than percentage of V-D TCRβ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D TCRβ chain junctions containing at least 3 N-additions than a corresponding non-human animal that does not have a nucleic acid encoding an exogenous TdT in its genome. In some embodiments, the percentage of V-D TCRβ chain junctions containing at least 3 N-additions in the genetically modified non-human animals provided herein is greater than percentage of V-D TCRβ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D TCRβ chain junctions containing at least 4 N-additions than a corresponding non-human animal that does not have a nucleic acid encoding an exogenous TdT in its genome. In some embodiments, the percentage of V-D TCRβ chain junctions containing at least 4 N-additions in the genetically modified non-human animals provided herein is greater than percentage of V-D TCRβ chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-D TCRβ chain junctions in the animal comprise non-template additions. In some embodiments, the non-human animal has a greater frequency of unique TCRβ CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%.

In some embodiments, the non-human animal provided herein has a greater percentage of D-J TCRβ chain junctions containing non-template additions than a corresponding non-human animal that does not have a nucleic acid encoding an exogenous TdT in its genome. In some embodiments, the percentage of D-J TCRβ chain junctions containing non-template additions in the genetically modified non-human animals provided herein is greater than percentage of D-J TCRβ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of D-J TCRβ chain junctions not containing non-template additions than a corresponding non-human animal that does not have a nucleic acid encoding an exogenous TdT in its genome. In some embodiments, the percentage of D-J TCRβ chain junctions not containing non-template additions in the genetically modified non-human animals provided herein is less than percentage of D-J TCRβ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of D-J TCRβ chain junctions containing at least 1 N-addition than a corresponding non-human animal that does not have a nucleic acid encoding an exogenous TdT in its genome. In some embodiments, the percentage of D-J TCRβ chain junctions containing at least 1 N-addition in the genetically modified non-human animals provided herein is greater than percentage of D-J TCRβ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of D-J TCRβ chain junctions containing at least 2 N-additions than a corresponding non-human animal that does not have a nucleic acid encoding an exogenous TdT in its genome. In some embodiments, the percentage of D-J TCRβ chain junctions containing at least 2 N-additions in the genetically modified non-human animals provided herein is greater than percentage of D-J TCRβ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of D-J TCRβ chain junctions containing at least 3 N-additions than a corresponding non-human animal that does not have a nucleic acid encoding an exogenous TdT in its genome. In some embodiments, the percentage of D-J TCRβ chain junctions containing at least 3 N-additions in the genetically modified non-human animals provided herein is greater than percentage of D-J TCRβ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of D-J TCRβ chain junctions containing at least 4 N-additions than a corresponding non-human animal that does not have a nucleic acid encoding an exogenous TdT in its genome. In some embodiments, the percentage of D-J TCRβ chain junctions containing at least 4 N-additions in the genetically modified non-human animals provided herein is greater than percentage of D-J TCRβ chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the D-J TCRβ chain junctions in the animal comprise non-template additions.

In some embodiments, the non-human animal provided herein has a greater percentage of V-J TCRγ chain junctions containing non-template additions than a corresponding non-human animal that does not have a nucleic acid encoding an exogenous TdT in its genome. In some embodiments, the percentage of V-J TCRγ chain junctions containing non-template additions in the genetically modified non-human animals provided herein is greater than percentage of V-J TCRγ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-J TCRγ chain junctions not containing non-template additions than a corresponding non-human animal that does not have a nucleic acid encoding an exogenous TdT in its genome. In some embodiments, the percentage of V-J TCRγ chain junctions not containing non-template additions in the genetically modified non-human animals provided herein is less than percentage of V-J TCRγ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRγ chain junctions containing at least 1 N-addition than a corresponding non-human animal that does not have a nucleic acid encoding an exogenous TdT in its genome. In some embodiments, the percentage of V-J TCRγ chain junctions containing at least 1 N-addition in the genetically modified non-human animals provided herein is greater than percentage of V-J TCRγ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRγ chain junctions containing at least 2 N-additions than a corresponding non-human animal that does not have a nucleic acid encoding an exogenous TdT in its genome. In some embodiments, the percentage of V-J TCRγ chain junctions containing at least 2 N-additions in the genetically modified non-human animals provided herein is greater than percentage of V-J TCRγ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRγ chain junctions containing at least 3 N-additions than a corresponding non-human animal that does not have a nucleic acid encoding an exogenous TdT in its genome. In some embodiments, the percentage of V-J TCRγ chain junctions containing at least 3 N-additions in the genetically modified non-human animals provided herein is greater than percentage of V-J TCRγ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRγ chain junctions containing at least 4 N-additions than a corresponding non-human animal that does not have a nucleic acid encoding an exogenous TdT in its genome. In some embodiments, the percentage of V-J TCRγ chain junctions containing at least 4 N-additions in the genetically modified non-human animals provided herein is greater than percentage of V-J TCRγ chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-J TCRγ chain junctions in the animal comprise non-template additions. In some embodiments, the non-human animal has a greater frequency of unique TCRγ CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%.

In some embodiments, the non-human animal provided herein has a greater percentage of V-D TCRδ chain junctions containing non-template additions than a corresponding non-human animal that does not have a nucleic acid encoding an exogenous TdT in its genome. In some embodiments, the percentage of V-D TCRδ chain junctions containing non-template additions in the genetically modified non-human animals provided herein is greater than percentage of V-D TCRδ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-D TCRδ chain junctions not containing non-template additions than a corresponding non-human animal that does not have a nucleic acid encoding an exogenous TdT in its genome. In some embodiments, the percentage of V-D TCRδ chain junctions not containing non-template additions in the genetically modified non-human animals provided herein is less than percentage of V-D TCRδ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D TCRδ chain junctions containing at least 1 N-addition than a corresponding non-human animal that does not have a nucleic acid encoding an exogenous TdT in its genome. In some embodiments, the percentage of V-D TCRδ chain junctions containing at least 1 N-addition in the genetically modified non-human animals provided herein is greater than percentage of V-D TCRδ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D TCRδ chain junctions containing at least 2 N-additions than a corresponding non-human animal that does not have a nucleic acid encoding an exogenous TdT in its genome. In some embodiments, the percentage of V-D TCRδ chain junctions containing at least 2 N-additions in the genetically modified non-human animals provided herein is greater than percentage of V-D TCRδ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D TCRδ chain junctions containing at least 3 N-additions than a corresponding non-human animal that does not have a nucleic acid encoding an exogenous TdT in its genome. In some embodiments, the percentage of V-D TCRδ chain junctions containing at least 3 N-additions in the genetically modified non-human animals provided herein is greater than percentage of V-D TCRδ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D TCRδ chain junctions containing at least 4 N-additions than a corresponding non-human animal that does not have a nucleic acid encoding an exogenous TdT in its genome. In some embodiments, the percentage of V-D TCRδ chain junctions containing at least 4 N-additions in the genetically modified non-human animals provided herein is greater than percentage of V-D TCRδ chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-D TCRδ chain junctions in the animal comprise non-template additions. In some embodiments, the non-human animal has a greater frequency of unique TCRδ CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%.

In some embodiments, the non-human animal provided herein has a greater percentage of D-J TCRδ chain junctions containing non-template additions than a corresponding non-human animal that does not have a nucleic acid encoding an exogenous TdT in its genome. In some embodiments, the percentage of D-J TCRδ chain junctions containing non-template additions in the genetically modified non-human animals provided herein is greater than percentage of D-J TCRδ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of D-J TCRδ chain junctions not containing non-template additions than a corresponding non-human animal that does not have a nucleic acid encoding an exogenous TdT in its genome. In some embodiments, the percentage of D-J TCRδ chain junctions not containing non-template additions in the genetically modified non-human animals provided herein is less than percentage of D-J TCRδ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of D-J TCRδ chain junctions containing at least 1 N-addition than a corresponding non-human animal that does not have a nucleic acid encoding an exogenous TdT in its genome. In some embodiments, the percentage of D-J TCRδ chain junctions containing at least 1 N-addition in the genetically modified non-human animals provided herein is greater than percentage of D-J TCRδ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of D-J TCRδ chain junctions containing at least 2 N-additions than a corresponding non-human animal that does not have a nucleic acid encoding an exogenous TdT in its genome. In some embodiments, the percentage of D-J TCRδ chain junctions containing at least 2 N-additions in the genetically modified non-human animals provided herein is greater than percentage of D-J TCRδ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of D-J TCRδ chain junctions containing at least 3 N-additions than a corresponding non-human animal that does not have a nucleic acid encoding an exogenous TdT in its genome. In some embodiments, the percentage of D-J TCRδ chain junctions containing at least 3 N-additions in the genetically modified non-human animals provided herein is greater than percentage of D-J TCRδ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of D-J TCRδ chain junctions containing at least 4 N-additions than a corresponding non-human animal that does not have a nucleic acid encoding an exogenous TdT in its genome. In some embodiments, the percentage of D-J TCRδ chain junctions containing at least 4 N-additions in the genetically modified non-human animals provided herein is greater than percentage of D-J TCRδ chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the D-J TCRδ chain junctions in the animal comprise non-template additions.

In some embodiments, the endogenous TdT loci in the non-human organism is intact. In some embodiments the endogenous TdT loci is inactivated. For example, in some embodiments, the endogenous TdT loci is deleted in whole or in part such that the non-human organism does not express endogenous TdT.

Non-Human Animals that Expressing Human Variable Domain Antibodies and Exogenous TdT In certain embodiments, the genetically modified non-human animals and non-human animal ES cells comprising exogenous TdT as described herein also comprise in their germline and/or genome an immunoglobulin locus (exogenous or endogenous) containing an immunoglobulin variable region comprising unrearranged human immunoglobulin variable region gene segments and an immunoglobulin constant region comprising an immunoglobulin constant region gene and in which the unrearranged human immunoglobulin variable region gene segments are operably linked to the immunoglobulin constant region gene. In some embodiments, the non-human animals and non-human ES cells comprise in their germline and/or genome multiple such immunoglobulin loci. For example, in some embodiments, the genetically modified non-human animals and non-human animal ES cells comprise in their germline and/or genome at least one immunoglobulin locus comprising unrearranged human heavy chain variable region gene segments and at least one immunoglobulin locus comprising unrearranged human light chain variable region gene segments (e.g., κ chain gene segments and/or λ chain gene segments). In some embodiments, the genetically modified non-human animals and non-human animal ES cells comprise in their germline and/or genome at least one immunoglobulin locus comprising unrearranged human heavy chain variable region gene segments, at least one immunoglobulin locus comprising unrearranged human κ chain variable region gene segments and at least one immunoglobulin locus comprising unrearranged human λ chain variable region gene segments. In some embodiments, genetically modified non-human animals, e.g., genetically modified mice or rats, comprise in their germline and/or genome genetically modified immunoglobulin loci (genetically modified rearranged or unrearranged immunoglobulin loci) such that the mice make human, humanized, partially human, reverse chimeric (human variable and non-human constant regions) antibodies.

Immunoglobulin loci comprising human variable region gene segments are known in the art and can be found, for example, in U.S. Pat. Nos. 5,633,425, 5,770,429, 5,814,318, 6,075,181, 6,114,598, 6,150,584, 6,998,514, 7,795,494, 7,910,798, 8,232,449, 8,502,018, 8,697,940, 8,703,485, 8,754,287, 8,791,323, 8,907,157, 9,035,128, 9,145,588, and 9,206,263 and each of which is hereby incorporated by reference in its entirety, as well as in U.S. Pat. Pub. Nos. 2008/0098490, 2010/0146647, 2011/0195454, 2012/0167237, 2013/0145484, 2013/0167256, 2013/0219535, 2013/0326647, 2013/0096287, 2014/013275, 2014/093908, and 2015/0113668, each of which is hereby incorporated by reference in its entirety, and in PCT Pub. Nos. WO2007117410, WO2008151081, WO2009157771, WO2010039900, WO2011004192, WO2011123708 and WO2014093908, each of which are hereby incorporated by reference in its entirety.

In some embodiments, the human unrearranged immunoglobulin variable region gene segments are heavy chain gene segments and the immunoglobulin constant region gene is a heavy chain constant region gene. In some embodiments, the human unrearranged immunoglobulin variable region gene segments are light chain, e.g., κ chain, gene segments, and the immunoglobulin constant region gene is a heavy chain constant region gene.

In some embodiments, the human unrearranged immunoglobulin variable region gene segments are heavy chain gene segments and the immunoglobulin constant region gene is a κ chain constant region gene. In some embodiments, the human unrearranged immunoglobulin variable region gene segments are κ chain gene segments and the immunoglobulin constant region gene is a κ chain constant region gene. In some embodiments, the human unrearranged immunoglobulin variable region gene segments are λ chain gene segments and the immunoglobulin constant region gene is a κ chain constant region gene. In some embodiments, the human unrearranged immunoglobulin variable region gene segments are λ chain gene segments and the immunoglobulin constant region gene is a λ chain constant region gene.

In certain embodiments, the immunoglobulin variable region contains unrearranged human Ig heavy chain variable region gene segments. In some embodiments, the unrearranged human Ig variable region gene segments comprise a plurality of human $V_H$ segments, one or more human $D_H$ segments and one or more human $J_H$ segments. In some embodiments, the unrearranged human Ig variable region gene segments comprise at least 3 $V_H$ gene segments, at least 18 $V_H$ gene segments, at least 20 $V_H$ gene segments, at least 30 $V_H$ gene segments, at least 40 $V_H$ gene segments, at least 50 $V_H$ gene segments, at least 60 $V_H$ gene segments, at least 70 $V_H$ gene segments, or at least 80 $V_H$ gene segments. In some embodiments, the unrearranged human Ig gene segments include all of the human $D_H$ gene segments. In some embodiments, the unrearranged human Ig gene segments include all of the human $J_H$ gene segments. Exemplary variable regions comprising Ig heavy chain gene segments are provided, for example, in Macdonald et al., *Proc. Natl. Acad. Sci. USA* 111:5147-52 and supplemental information, which is hereby incorporated by reference. In some embodiments, the non-human animals provided herein have a restricted immunoglobulin heavy chain locus characterized by a single polymorphic human $V_H$ gene segment, a plurality of $D_H$ gene segments and a plurality of $J_H$ gene segments (e.g., as described in U.S. Pat. Pub. No. 2013/0096287, which is hereby incorporated by reference). In some embodiments the $V_H$ gene segment is VH1-2 or VH1-69.

In various embodiments, the immunoglobulin locus modifications described herein do not affect fertility of the non-human animal. In some embodiments, the heavy chain locus comprises an endogenous Adam6a gene, Adam6b gene, or both, and the genetic modification does not affect the expression and/or function of the endogenous Adam6a gene, Adam6b gene, or both. In some embodiments, the genome of the genetically modified non-human animal comprises an ectopically located Adam6a gene, Adam6b gene, or both. Exemplary non-human animals expressing exogenous Adam6a and/or Adam6b are described in U.S. Pat. Nos. 8,642,835 and 8,697,940, each of which is hereby incorporated by reference in its entirety.

In some embodiments, the human immunoglobulin heavy chain variable region gene segments rearrange during B cell development to generate rearranged human heavy chain variable region genes in the B cells of the non-human organism. In some embodiments, the non-human animal provided herein has a greater percentage of V-D and/or D-J immunoglobulin heavy chain junctions containing non-template additions than a corresponding non-human animal that does not have a nucleic acid encoding an exogenous TdT in its genome. In some embodiments, the percentage of V-D and/or D-J immunoglobulin heavy chain junctions containing non-template additions in the genetically modified non-human animals provided herein is greater than percentage of V-D and/or D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-D immunoglobulin heavy chain junctions not containing non-template additions than a corresponding non-human animal that does not have a nucleic acid encoding an exogenous TdT in its genome. In some embodiments, the percentage of V-D and/or D-J immunoglobulin heavy chain junctions not containing non-template additions in the genetically modified non-human animals provided herein is less than percentage of V-D and/or D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J immunoglobulin heavy chain junctions containing at least 1 N-addition than a corresponding non-human animal that does not have a nucleic acid encoding an exogenous TdT in its genome. In some embodiments, the percentage of V-D and/or D-J immunoglobulin heavy chain junctions containing at least 1 N-addition in the genetically modified non-human animals provided herein is greater than percentage of V-D and/or D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J immunoglobulin heavy chain junctions containing at least 2 N-additions than a corresponding non-human animal that does not have a nucleic acid encoding an exogenous TdT in its genome. In some embodiments, the percentage of V-D and/or D-J immunoglobulin heavy chain junctions containing at least 2 N-additions in the genetically modified non-human animals provided herein is greater than percentage of V-D and/or D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J immunoglobulin heavy chain junctions containing at least 3 N-additions than a corresponding non-human animal that does not have a nucleic acid encoding an exogenous TdT in its genome. In some embodiments, the percentage of V-D and/or D-J immunoglobulin heavy chain junctions containing at least 3 N-additions in the genetically modified non-human animals provided herein is greater than percentage of V-D and/or D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J immunoglobulin heavy chain junctions containing at least 4 N-additions than a corresponding non-human animal that does not have a nucleic acid encoding an exogenous TdT in its genome. In some embodiments, the percentage of V-D and/or D-J immunoglobulin heavy chain junctions containing at least 4 N-additions in the genetically modified non-human animals provided herein is greater than percentage of V-D and/or D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-D and/or D-J immunoglobulin heavy chain junctions in the animal comprise non-template additions. In some embodiments, the non-human animal has a greater frequency of unique immunoglobulin heavy chain CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%.

In certain embodiments, the immunoglobulin variable region contains unrearranged human Ig κ variable region gene segments. In some embodiments, the unrearranged human immunoglobulin variable region gene segments comprise a plurality of human $V_\kappa$ segments and one or more human $J_\kappa$ segments. In some embodiments, the unrearranged human immunoglobulin variable region gene segments comprise all of the human $J_\kappa$ segments. In some embodiments, the immunoglobulin variable region gene segments comprise four functional $V_\kappa$ segments and all human $J_\kappa$ segments. In some embodiments, the immunoglobulin variable region gene segments comprise 16 functional $V_\kappa$ segments and all human $J_\kappa$ segments (e.g., all functional human $V_\kappa$ segments and $J_\kappa$ segments). In some embodiments, the unrearranged human immunoglobulin variable region gene segments comprise all of the human $V_\kappa$ segments and all human $J_\kappa$ segments. Exemplary variable regions comprising Ig κ gene segments are provided, for example, in Macdonald et al., *Proc. Natl. Acad. Sci. USA* 111:5147-52 and supplemental information, which is hereby incorporated by reference. In some embodiments, the non-human animals provided herein have a restricted immunoglobulin light chain locus characterized by no more than two human $V_L$ gene segments and a plurality of $J_L$ gene segments (e.g., dual light chain mice, or DLC, as described in U.S. Pat. Pub. No. 2013/0198880, which is hereby incorporated by reference). In some embodiments the $V_L$ gene segments are $V_\kappa$ gene segments. In some embodiments the $V_L$ gene segments are $V_\lambda$ gene segments. In some embodiments the $V_\kappa$ gene segments are IGKV3-20 and IGKV1-39.

In some embodiments, the human immunoglobulin κ variable region gene segments rearrange during B cell development to generate rearranged human κ variable region genes in the B cells of the non-human organism. In some embodiments, the non-human animal provided herein has a greater percentage of V-J immunoglobulin κ chain junctions containing non-template additions than a corresponding non-human animal that does not have a nucleic acid encoding an exogenous TdT in its genome. In some embodiments, the percentage of V-J immunoglobulin κ chain junctions containing non-template additions in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-J immunoglobulin κ chain junctions not containing non-template additions than a corresponding non-human animal that does not have a nucleic acid encoding an exogenous TdT in its genome. In some embodiments, the percentage of V-J immunoglobulin κ chain junctions not containing non-template additions in the genetically modified non-human animals provided herein is less than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin κ chain junctions containing at least 1 N-addition than a corresponding non-human animal that does not have a nucleic acid encoding an exogenous TdT in its genome. In some embodiments, the percentage of V-J immunoglobulin κ chain junctions containing at least 1 N-addition in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin κ chain junctions containing at least 2 N-additions than a corresponding non-human animal that does not have a nucleic acid encoding an exogenous TdT in its genome. In some embodiments, the percentage of V-J immunoglobulin κ chain junctions containing at least 2 N-additions in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin κ chain junctions containing at least 3 N-additions than a corresponding non-human animal that does not have a nucleic acid encoding an exogenous TdT in its genome. In some embodiments, the percentage of V-J immunoglobulin κ chain junctions containing at least 3 N-additions in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin κ chain junctions containing at least 4 N-additions than a corresponding non-human animal that does not have a nucleic acid encoding an exogenous TdT in its genome. In some embodiments, the percentage of V-J immunoglobulin κ chain junctions containing at least 4 N-additions in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-J immunoglobulin κ chain junctions in the animal comprise non-template additions. In some embodiments, the non-human animal has a greater frequency of unique immunoglobulin κ chain CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%. In some embodiments, the non-human animal provided herein has at least 900, 1000, 1100, 1200, 1300, 1400, 1500 or 1700 unique immunoglobulin κ chain CDR3 sequences per 10,000 immunoglobulin κ chain CDR3 sequences.

In certain embodiments, the immunoglobulin variable region contains unrearranged human Ig λ variable region gene segments. In some embodiments, the unrearranged human immunoglobulin variable region gene segments comprise a plurality of human $V_\lambda$ segments and one or more human $J_\lambda$ segments. In some embodiments, the unrearranged human immunoglobulin variable region gene segments comprise all of the human $V_\lambda$ segments. In some embodiments, the unrearranged human immunoglobulin variable region gene segments comprise all of the human $J_\lambda$ segments. Exemplary variable regions comprising Ig λ gene segments are provided, for example, U.S. Pat. Pub. Nos. 2012/0073004 and 2002/0088016, each of which is hereby incorporated by reference.

In some embodiments, the human immunoglobulin λ variable region gene segments rearrange during B cell development to generate rearranged human λ variable region genes in the B cells of the non-human organism. In some embodiments, the non-human animal provided herein has a greater percentage of V-J immunoglobulin λ chain junctions containing non-template additions than a corresponding non-human animal that does not have a nucleic acid encoding an exogenous TdT in its genome. In some embodiments, the percentage of V-J immunoglobulin λ chain junctions containing non-template additions in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-J immunoglobulin λ chain junctions not containing non-template additions than a corresponding non-human animal that does not have a nucleic acid encoding an exogenous TdT in its genome. In some embodiments, the percentage of V-J immunoglobulin λ chain junctions not containing non-template additions in the genetically modified non-human animals provided herein is less than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin λ chain junctions containing at least 1 N-addition than a corresponding non-human animal that does not have a nucleic acid encoding an exogenous TdT in its genome. In some embodiments, the percentage of V-J immunoglobulin λ chain junctions containing at least 1 N-addition in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin λ chain junctions containing at least 2 N-additions than a corresponding non-human animal that does not have a nucleic acid encoding an exogenous TdT in its genome. In some embodiments, the percentage of V-J immunoglobulin λ chain junctions containing at least 2 N-additions in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin λ chain junctions containing at least 3 N-additions than a corresponding non-human animal that does not have a nucleic acid encoding an exogenous TdT in its genome. In some embodiments, the percentage of V-J immunoglobulin λ chain junctions containing at least 3 N-additions in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin λ chain junctions containing at least 4 N-additions than a corresponding non-human animal that does not have a nucleic acid encoding an exogenous TdT in its genome. In some embodiments, the percentage of V-J immunoglobulin λ chain junctions containing at least 4 N-additions in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-J immunoglobulin λ chain junctions in the animal comprise non-template additions. In some embodiments, the non-human animal has a greater frequency of unique immunoglobulin λ chain CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%. In some embodiments, the non-human animal provided herein has at least 150, 160, 170, 180, 190, 200, 210, 220, 230, 240, 250, 260, 270, 280, 290 or 300 unique immunoglobulin λ chain CDR3 sequences per 10,000 immunoglobulin λ chain CDR3 sequences.

In some embodiments, the immunoglobulin variable region comprising unrearranged human immunoglobulin variable region gene segments also includes human immunoglobulin variable region intergenic sequences. In some embodiments, the immunoglobulin variable region includes non-human (e.g., rodent, rat, mouse) Ig variable region intergenic sequences. In some embodiments, the intergenic sequence is of endogenous species origin.

In some embodiments, the non-human organism comprises in its germline and/or genome an immunoglobulin locus comprising a rearranged heavy chain variable region (a universal heavy chain variable region). In some embodiments, the rearranged Ig heavy chain variable region gene is a human rearranged Ig heavy chain variable region gene. Exemplary rearranged Ig heavy chain variable regions are provided in U.S. Patent Pub. No. 2014/0245468, which is hereby incorporated by reference. In some embodiments, the non-human organism comprising a universal heavy chain variable region is used to produce bispecific antibodies.

In some embodiments, the non-human organism comprises in its germline and/or genome an immunoglobulin locus comprising a rearranged light variable region (a universal light chain variable region). In some embodiments, the rearranged Ig light chain variable region gene is a human rearranged Ig light chain variable region gene. Exemplary rearranged Ig light chain variable regions are provided in, e.g., U.S. Patent Pub. Nos. 2011/0195454, 2012/0021409, 2012/0192300, 2013/0045492, 2013/0185821, 2013/0302836, 2015/0313193, 2015/0059009, and 2013/0198879, which are hereby incorporated by reference. In some embodiments, the non-human organism ("universal light chain" organism) comprising a universal light chain variable region is used to produce bispecific antibodies.

In some embodiments, the non-human organism comprises in its germline and/or genome a light chain immunoglobulin locus comprising a limited repertoire of light chain variable gene segments (e.g., a dual light chain variable region comprising two light chain variable gene segments). In some embodiments, the light chain variable gene segments in the limited repertoire of light chain gene segments are a human light chain gene segments. Exemplary dual light chain variable regions are provided in U.S. Patent Pub. No. 2013/0198880, which is hereby incorporated by reference. In some embodiments, the non-human organism comprising a dual light chain variable region is used to produce bispecific antibodies.

In yet other embodiments, the non-human organism may comprise in its germline and/or genome a light chain and/or a heavy chain immunoglobulin locus that includes insertions and/or replacements of histidine codons designed to introduce pH-dependent binding properties to the antibodies generated in such non-human organism. In some of such embodiments, the histidine codons are inserted and/or replaced in the nucleic acid sequences encoding CDR3. Various such light and/or heavy immunoglobulin loci are provided in U.S. Pat. Nos. 9,301,510, 9,334,334, U.S. Patent Application Publication Nos. 2013/0247236, 20140013456, incorporated herein by reference.

In some embodiments, the immunoglobulin constant region comprises a heavy chain constant region gene. In some embodiments, the heavy chain constant region gene is a human heavy chain constant region gene. In some embodiments, the heavy chain constant region gene is of endogenous species origin. In some embodiments, the heavy chain constant region gene is a mouse constant region gene or a rat constant region gene. In some embodiments, the constant region gene is a mixture of human and non-human sequence. For example, in some embodiments, the constant region gene encodes a human CH1 region and a non-human (e.g., endogenous species origin, mouse, rat) CH2 and/or CH3 region. In some embodiments, the heavy chain constant region gene is an Cμ, Cδ, Cγ (Cγ1, Cγ2, Cγ3, Cγ4), Cα or Cε constant region gene. In some embodiments, the constant region gene is an endogenous constant region gene. In some embodiments, the constant region gene encodes a mutated CH1 region so that the non-human animal expresses heavy chain only antibodies (see, e.g., U.S. Pat. No. 8,754,287, U.S. Patent Application Publication No. 2015/0289489, incorporated herein by reference). In some embodiments, e.g., where the goal is to generate heavy chains to make bispecific antibodies (e.g., in universal or dual light chain organisms), the Fc domains of the heavy chains comprise modifications to facilitate heavy chain heterodimer formation and/or to inhibit heavy chain homodimer formation. Such modifications are provided, for example, in U.S. Pat. Nos. 5,731,168, 5,807,706, 5,821,333, 7,642,228 and 8,679, 785 and in U.S. Pat. Pub. No. 2013/0195849, each of which is hereby incorporated by reference.

In some embodiments, the immunoglobulin constant region comprises a light chain constant region gene. In some embodiments, the light chain constant region gene is a κ constant region gene. In some embodiments, the light chain constant region gene is a λ constant region gene. In some embodiments, the light chain constant region gene is of endogenous species origin. In some embodiments, the light chain constant region gene is a mouse constant region gene or a rat constant region gene. In some embodiments, the light chain constant region gene is a mixture of human and non-human sequence.

In some embodiments, the immunoglobulin variable region comprising human variable region gene segments and the immunoglobulin constant region gene to which the variable region gene segments are operably linked are located at an endogenous immunoglobulin locus. In some embodiments, the endogenous immunoglobulin locus is an endogenous heavy chain locus. In some embodiments, the endogenous immunoglobulin locus is an endogenous κ locus. In some embodiments, the endogenous immunoglobulin locus is an endogenous λ locus. In some embodiments, the constant region gene to which the human variable region gene segments are operably linked is an endogenous constant region gene.

In some embodiments, one or more of the endogenous immunoglobulin loci or a portion of the one or more endogenous loci (e.g., a variable region and/or a constant region) in the genome of the non-human animal provided herein is inactivated. Endogenous immunoglobulin variable region gene loci and portions thereof can be inactivated using any method known in the art, including, but not limited to, the deletion of the locus or a portion thereof from the genome of the organism, the replacement of a locus or a portion thereof with a different nucleic acid sequence, the inversion of a portion of the locus and/or the displacement of a portion of the locus to another position in the genome of the non-human organism. In some embodiments the inactivation of the locus is only a partial inactivation. In some embodiments, the variable region of the locus is inactivated but the constant region remains functional (e.g., because it is operably linked to non-endogenous variable region gene segments).

In some embodiments, the genetically modified non-human animal includes an inactivated endogenous immunoglobulin heavy chain locus. In some embodiments, the endogenous immunoglobulin heavy chain locus or a portion thereof is inactivated by deletion, replacement, displacement and/or inversion of at least part of the endogenous variable region of the endogenous heavy chain locus. In some embodiments, the at least part of the variable region of the endogenous heavy chain locus that is deleted, replaced, displaced, and/or inverted comprises the J segments of the variable region. In some embodiments, the endogenous immunoglobulin heavy chain locus or portion thereof is inactivated by deletion, replacement, displacement and/or inversion of at least part of the endogenous constant region of the endogenous heavy chain locus. In some embodiments, the at least part of the constant region of the endogenous heavy chain locus that is deleted, replaced, displaced, and/or inverted comprises the Cμ gene of the endogenous constant region.

In some embodiments, the genetically modified non-human animal includes an inactivated endogenous immunoglobulin κ chain locus. In some embodiments, the endogenous immunoglobulin κ chain locus or a portion thereof is inactivated by deletion, replacement, displacement and/or inversion of at least part of the endogenous variable region of the endogenous κ chain locus. In some embodiments, the at least part of the variable region of the endogenous κ chain locus that is deleted, replaced, displaced, and/or inverted comprises the J segments of the variable region. In some embodiments, the endogenous immunoglobulin κ chain locus or portion thereof is inactivated by deletion, replacement, displacement and/or inversion of at least part of the endogenous constant region of the endogenous κ chain locus. In some embodiments, the at least part of the constant region of the endogenous κ chain locus that is deleted, replaced, displaced, and/or inverted comprises the Cκ gene of the endogenous constant region.

In some embodiments, the genetically modified non-human animal includes an inactivated endogenous immunoglobulin λ chain locus. In some embodiments, the endogenous immunoglobulin λ chain locus or a portion thereof is inactivated by deletion, replacement, displacement and/or inversion of at least part of an endogenous variable region of the endogenous λ chain locus. In some embodiments, the at least part of at least one V-J-C gene cluster in the endogenous λ chain locus is deleted, replaced, displaced, and/or inverted. In some embodiments, the endogenous immunoglobulin λ chain locus or portion thereof is inactivated by deletion, replacement, displacement and/or inversion of at least part of an endogenous constant region of the endogenous λ chain locus. In some embodiments, the at least part of the constant region of the endogenous λ chain locus that is deleted, replaced, displaced, and/or inverted comprises a Cλ gene of the endogenous constant region.

In some embodiments, the genetically modified non-human animal provided herein expresses antibodies having human variable domains (e.g., a human variable domain derived from the unrearranged human variable region gene segments described herein). In some embodiments, the human variable domain is a human heavy chain variable domain. In some embodiments, the antibodies are heavy chain only antibodies. In some embodiments, the human variable domain is a human light chain variable domain. In some embodiments, the antibodies produced by the non-human animals have both human heavy chain variable domains and human light chain variable domains. In some embodiments, the antibodies have human heavy chain constant domains. In some embodiments, the antibodies have human light chain constant domains. In some embodiments, the heavy and/or light chain constant domain is of non-human origin. For example, in some embodiments, the heavy chain constant domain is of endogenous species origin. In some embodiments, the heavy chain constant domain is of mouse or rat origin. In some embodiments, the light chain constant domain is of endogenous species origin. In some embodiments, the light chain constant domain is of rat or mouse origin.

Non-Human Animals Expressing Human Variable Domain T Cell Receptors and Exogenous TdT In certain embodiments, the genetically modified non-human animals and non-human animal ES cells that comprise exogenous TdT as described herein also comprise in their germline and/or genome a TCR locus (exogenous or endogenous) containing a TCR variable region comprising unrearranged human TCR variable region gene segments and a TCR constant region comprising a TCR constant region gene and in which the unrearranged human TCR variable region gene segments are operably linked to the TCR constant region gene. In some embodiments, various genetically modified non-human animals, e.g., genetically modified mice, comprise in their germline and/or genome genetically modified T cell receptor loci (genetically modified TCRα, β, γ and/or δ loci) such that the mice express human, humanized, partially human, reverse chimeric (human variable and non-human constant regions) T cell receptors. In one embodiment, the exemplary non-human animal is provided in U.S. Pat. No. 9,113,616 and International Pub. No. WO 2016/164492, incorporated herein by reference.

In some embodiments, the TCR constant region gene is a non-human TCR constant region gene. In some embodiments, the TCR constant region gene is a rodent constant region gene, such as a rat constant region gene or a mouse constant region gene. In some embodiments, the constant region gene is of endogenous species origin. In some embodiments, the TCR constant region gene is a human constant region gene.

In some embodiments, the non-human animals and non-human ES cells comprise in their germline and/or genome multiple such TCR loci. For example, in some embodiments, the genetically modified non-human animals and non-human animal ES cells comprise in their germline and/or genome at least one TCR locus comprising unrearranged TCRα variable region gene segments and at least one TCR locus comprising unrearranged TCRβ variable region gene segments. In some embodiments, the genetically modified non-human animals and non-human animal ES cells comprise in their germline and/or genome at least one TCR locus comprising unrearranged human TCRγ variable region gene segments and at least one TCR locus comprising unrearranged human TCRδ variable region gene segments.

In some embodiments, the human unrearranged TCR variable region gene segments are TCRα gene segments and the TCR constant region gene is a TCRα constant region gene. In some embodiments, the human unrearranged TCR variable region gene segments are TCRβ chain gene segments and the TCR constant region gene is a TCRβ constant region gene. In some embodiments, the human unrearranged TCR variable region gene segments are TCRγ chain gene segments and the TCR constant region gene is a TCRγ constant region gene. In some embodiments, the human unrearranged TCR variable region gene segments are TCRδ chain gene segments and the TCR constant region gene is a TCRδ constant region gene. Exemplary variable regions comprising human TCR gene segments are provided, for example, in U.S. Pat. No. 9,113,616 and Li et al., Nature Medicine 16:1029-1035 (2010), each of which is hereby incorporated by reference.

In some embodiments, the TCR variable region contains unrearranged human TCRβ variable region gene segments. In some embodiments, the human TCRβ variable region gene segments rearrange during T cell development to generate rearranged human TCRβ variable region genes in the T cells of the non-human organism. In some embodiments, the non-human animal provided herein has a greater percentage of V-D and/or D-J TCRβ junctions containing non-template additions than a corresponding non-human animal that does not have a nucleic acid encoding an exogenous TdT in its genome. In some embodiments, the percentage of V-D and/or D-J TCRβ junctions containing non-template additions in the genetically modified non-human animals provided herein is greater than percentage of V-D and/or D-J TCRβ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-D TCRβ junctions not containing non-template additions than a corresponding non-human animal that does not have a nucleic acid encoding an exogenous TdT in its genome. In some embodiments, the percentage of V-D and/or D-J TCRβ junctions not containing non-template additions in the genetically modified non-human animals provided herein is less than percentage of V-D and/or D-J TCRβ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J TCRβ junctions containing at least 1 N-addition than a corresponding non-human animal that does not have a nucleic acid encoding an exogenous TdT in its genome. In some embodiments, the percentage of V-D and/or D-J TCRβ junctions containing at least 1 N-addition in the genetically modified non-human animals provided herein is greater than percentage of V-D and/or D-J TCRβ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J TCRβ junctions containing at least 2 N-additions than a corresponding non-human animal that does not have a nucleic acid encoding an exogenous TdT in its genome. In some embodiments, the percentage of V-D and/or D-J TCRβ junctions containing at least 2 N-additions in the genetically modified non-human animals provided herein is greater than percentage of V-D and/or D-J TCRβ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J TCRβ junctions containing at least 3 N-additions than a corresponding non-human animal that does not have a nucleic acid encoding an exogenous TdT in its genome. In some embodiments, the percentage of V-D and/or D-J TCRβ junctions containing at least 3 N-additions in the genetically modified non-human animals provided herein is greater than percentage of V-D and/or D-J TCRβ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J TCRβ junctions containing at least 4 N-additions than a corresponding non-human animal that does not have a nucleic acid encoding an exogenous TdT in its genome. In some embodiments, the percentage of V-D and/or D-J TCRβ junctions containing at least 4 N-additions in the genetically modified non-human animals provided herein is greater than percentage of V-D and/or D-J TCRβ junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-D and/or D-J TCRβ junctions in the animal comprise non-template additions. In some embodiments, the non-human animal has a greater frequency of unique TCRβ CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%.

In some embodiments, the TCR variable region contains unrearranged human TCRα variable region gene segments. In some embodiments, the human TCRα variable region gene segments rearrange during T cell development to generate rearranged human TCRα variable region genes in the T cells of the non-human organism. In some embodiments, the non-human animal provided herein has a greater percentage of V-J TCRα junctions containing non-template additions than a corresponding non-human animal that does not have a nucleic acid encoding an exogenous TdT in its genome. In some embodiments, the percentage of V-J TCRα junctions containing non-template additions in the genetically modified non-human animals provided herein is greater than percentage of V-J TCRα junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-D TCRα junctions not containing non-template additions than a corresponding non-human animal that does not have a nucleic acid encoding an exogenous TdT in its genome. In some embodiments, the percentage of V-J TCRα junctions not containing non-template additions in the genetically modified non-human animals provided herein is less than percentage of V-J TCRα junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRα junctions containing at least 1 N-addition than a corresponding non-human animal that does not have a nucleic acid encoding an exogenous TdT in its genome. In some embodiments, the percentage of V-J TCRα junctions containing at least 1 N-addition in the genetically modified non-human animals provided herein is greater than percentage of V-J TCRα junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRα junctions containing at least 2 N-additions than a corresponding non-human animal that does not have a nucleic acid encoding an exogenous TdT in its genome. In some embodiments, the percentage of V-J TCRα junctions containing at least 2 N-additions in the genetically modified non-human animals provided herein is greater than percentage of V-J TCRα junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRα junctions containing at least 3 N-additions than a corresponding non-human animal that does not have a nucleic acid encoding an exogenous TdT in its genome. In some embodiments, the percentage of V-J TCRα junctions containing at least 3 N-additions in the genetically modified non-human animals provided herein is greater than percentage of V-J TCRα junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRα junctions containing at least 4 N-additions than a corresponding non-human animal that does not have a nucleic acid encoding an exogenous TdT in its genome. In some embodiments, the percentage of V-J TCRα junctions containing at least 4 N-additions in the genetically modified non-human animals provided herein is greater than percentage of V-J TCRα junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-J TCRα junctions in the animal comprise non-template additions. In some embodiments, the non-human animal has a greater frequency of unique TCRα CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%.

In some embodiments, the TCR variable region contains unrearranged human TCRδ variable region gene segments. In some embodiments, the human TCRδ variable region gene segments rearrange during T cell development to generate rearranged human TCRδ variable region genes in the T cells of the non-human organism. In some embodiments, the non-human animal provided herein has a greater percentage of V-D and/or D-J TCRδ junctions containing non-template additions than a corresponding non-human animal that does not have a nucleic acid encoding an exogenous TdT in its genome. In some embodiments, the percentage of V-D and/or D-J TCRδ junctions containing non-template additions in the genetically modified non-human animals provided herein is greater than percentage of V-D and/or D-J TCRδ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-D TCRδ junctions not containing non-template additions than a corresponding non-human animal that does not have a nucleic acid encoding an exogenous TdT in its genome. In some embodiments, the percentage of V-D and/or D-J TCRδ junctions not containing non-template additions in the genetically modified non-human animals provided herein is less than percentage of V-D and/or D-J TCRδ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J TCRδ junctions containing at least 1 N-addition than a corresponding non-human animal that does not have a nucleic acid encoding an exogenous TdT in its genome. In some embodiments, the percentage of V-D and/or D-J TCRδ junctions containing at least 1 N-addition in the genetically modified non-human animals provided herein is greater than percentage of V-D and/or D-J TCRδ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J TCRδ junctions containing at least 2 N-additions than a corresponding non-human animal that does not have a nucleic acid encoding an exogenous TdT in its genome. In some embodiments, the percentage of V-D and/or D-J TCRδ junctions containing at least 2 N-additions in the genetically modified non-human animals provided herein is greater than percentage of V-D and/or D-J TCRδ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J TCRδ junctions containing at least 3 N-additions than a corresponding non-human animal that does not have a nucleic acid encoding an exogenous TdT in its genome. In some embodiments, the percentage of V-D and/or D-J TCRδ junctions containing at least 3 N-additions in the genetically modified non-human animals provided herein is greater than percentage of V-D and/or D-J TCRδ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J TCRδ junctions containing at least 4 N-additions than a corresponding non-human animal that does not have a nucleic acid encoding an exogenous TdT in its genome. In some embodiments, the percentage of V-D and/or D-J TCRδ junctions containing at least 4 N-additions in the genetically modified non-human animals provided herein is greater than percentage of V-D and/or D-J TCRδ junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-D and/or D-J TCRδ junctions in the animal comprise non-template additions. In some embodiments, the non-human animal has a greater frequency of unique TCRδ CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%.

In some embodiments, the TCR variable region contains unrearranged human TCRγ variable region gene segments. In some embodiments, the human TCRγ variable region gene segments rearrange during T cell development to generate rearranged human TCRγ variable region genes in the T cells of the non-human organism. In some embodiments, the non-human animal provided herein has a greater percentage of V-J TCRγ junctions containing non-template additions than a corresponding non-human animal that does not have a nucleic acid encoding an exogenous TdT in its genome. In some embodiments, the percentage of V-J TCRγ junctions containing non-template additions in the genetically modified non-human animals provided herein is greater than percentage of V-J TCRγ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-D TCRγ junctions not containing non-template additions than a corresponding non-human animal that does not have a nucleic acid encoding an exogenous TdT in its genome. In some embodiments, the percentage of V-J TCRγ junctions not containing non-template additions in the genetically modified non-human animals provided herein is less than percentage of V-J TCRγ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRγ junctions containing at least 1 N-addition than a corresponding non-human animal that does not have a nucleic acid encoding an exogenous TdT in its genome. In some embodiments, the percentage of V-J TCRγ junctions containing at least 1 N-addition in the genetically modified non-human animals provided herein is greater than percentage of V-J TCRγ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRγ junctions containing at least 2 N-additions than a corresponding non-human animal that does not have a nucleic acid encoding an exogenous TdT in its genome. In some embodiments, the percentage of V-J TCRγ junctions containing at least 2 N-additions in the genetically modified non-human animals provided herein is greater than percentage of V-J TCRγ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRγ junctions containing at least 3 N-additions than a corresponding non-human animal that does not have a nucleic acid encoding an exogenous TdT in its genome. In some embodiments, the percentage of V-J TCRγ junctions containing at least 3 N-additions in the genetically modified non-human animals provided herein is greater than percentage of V-J TCRγ junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J TCRγ junctions containing at least 4 N-additions than a corresponding non-human animal that does not have a nucleic acid encoding an exogenous TdT in its genome. In some embodiments, the percentage of V-J TCRγ junctions containing at least 4 N-additions in the genetically modified non-human animals provided herein is greater than percentage of V-J TCRγ junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-J TCRγ junctions in the animal comprise non-template additions. In some embodiments, the non-human animal has a greater frequency of unique TCRγ CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%.

In some embodiments, the TCR variable region comprising unrearranged human TCR variable region gene segments also includes human TCR variable region intergenic sequences. In some embodiments, the TCR variable region includes non-human (e.g., rodent, rat, mouse) TCR variable region intergenic sequences. In some embodiments, the intergenic sequences are of endogenous species origin.

In some embodiments, TCR variable region comprising human variable region gene segments and the TCR constant region gene to which the variable region gene segments are operably linked are located at an endogenous TCR locus. In some embodiments, the endogenous TCR locus is an endogenous TCRα locus. In some embodiments, the endogenous TCR locus is an endogenous TCRβ locus. In some embodiments, the endogenous TCR locus is an endogenous TCRγ locus. In some embodiments, the endogenous TCR locus is an endogenous TCRδ locus. In some embodiments, the constant region gene to which the human variable region gene segments are operably linked is an endogenous constant region gene, e.g., the corresponding endogenous constant region.

In some embodiments, one or more of the endogenous TCR loci or a portion of the one or more endogenous loci (e.g., a variable region and/or a constant region) in the genome of the non-human animal provided herein is inactivated. Endogenous TCR variable region gene loci and portions thereof can be inactivated using any method known in the art, including, but not limited to, the deletion of the locus or a portion thereof from the genome of the organism, the replacement of a locus or a portion thereof with a different nucleic acid sequence, the inversion of a portion of the locus and/or the displacement of a portion of the locus to another position in the genome of the non-human organism. In some embodiments the inactivation of the locus is only a partial inactivation. In some embodiments, the variable region of the locus is inactivated but the constant region remains functional (e.g., because it is operably linked to non-endogenous variable region gene segments). Examples of inactivated TCR loci are described, for example, in Mombaerts et al., *Proc. Natl. Acad. Sci. USA* 88:3084-3087 (1991) and Mombaerts et al., *Nature* 390:225-231 (1992), each of which is hereby incorporated by reference.

In some embodiments, the genetically modified non-human animal provided herein expresses TCR having human variable domains (e.g., a human variable domain derived from the unrearranged human variable region gene segments described herein). In some embodiments, the human variable domain is a human TCRα variable domain. In some embodiments, the human variable domain is a human TCRβ variable domain. In some embodiments, the human variable domain is a human TCRγ variable domain. In some embodiments, the human variable domain is a human TCRδ variable domain. In some embodiments, the TCR produced by the non-human animals have both human TCRα variable domains and human TCRβ variable domains. In some embodiments, the TCR produced by the non-human animals have both human TCRγ variable domains and human TCRδ variable domains. In some embodiments, the TCR produced by the non-human animals have both human TCRα variable domains and human TCRβ variable domains, and both human TCRγ variable domains and human TCRδ variable domains. In some embodiments, the TCR have human constant domains. In some embodiments, the constant domains are of non-human origin. For example, in some embodiments, constant domains are of endogenous species origin. In some embodiments, the constant domains are of mouse or rat origin.

Non-Human Animals Expressing Chimeric Antigen Receptors (CARs) and Exogenous TdT In certain aspects, provided herein are genetically modified non-human animals and non-human animal ES cells comprising exogenous TdT as described herein that also comprise chimeric antigen receptor (CAR) loci. Such CAR loci generally comprise a variable region and a constant region. The variable region includes unrearranged human Ig variable region gene segments, while the constant region locus includes a TCR constant region gene, wherein the Ig variable region gene segments are operably linked to the constant region gene. In some embodiments, the TCR constant region gene is a non-human TCR constant region gene. In some embodiments, the TCR constant region gene is a rodent constant region gene, such as a rat constant region gene or a mouse constant region gene. In some embodiments, the constant region gene is of endogenous species origin. In some embodiments, the TCR constant region gene is a human constant region gene.

In some embodiments, the CAR loci described herein are located at an endogenous TCR loci. For example, in some embodiments, a CAR locus comprising a TCRα constant region gene is located at an endogenous TCRα constant region locus. In some embodiments, such a locus is created by replacing some or all of the TCRα unrearranged variable region with an unrearranged Ig variable region. In some embodiments, a CAR locus comprising a TCRβ constant region gene is located at an endogenous TCRβ constant region locus. In some embodiments, such a locus is created by replacing some or all of the TCRβ unrearranged variable region with an unrearranged Ig variable region.

In certain embodiments, the CAR variable region locus will contain unrearranged human Ig variable region gene segments. Exemplary variable region loci comprising human variable region gene segments have been described in the art. For example, such loci are described in U.S. Pat. Nos. 5,633,425, 5,770,429, 5,814,318, 6,075,181, 6,114,598, 6,150,584, 6,998,514, 7,795,494, 7,910,798, 8,232,449, 8,502,018, 8,697,940, 8,703,485, 8,754,287, 8,791,323, 8,907,157, 9,035,128, 9,145,588, and 9,206,263 and each of which is hereby incorporated by reference in its entirety, as well as in U.S. Pat. Pub. Nos. 2008/0098490, 2010/0146647, 2011/0195454, 2012/0167237, 2013/0145484, 2013/0167256, 2013/0219535, 2013/0326647, 2014/013275, 2014/093908, 2015/0113668 and 2016/0081314, each of which is hereby incorporated by reference in its entirety, and in PCT Pub. Nos. WO2007117410, WO2008151081, WO2009157771, WO2010039900, WO2011004192, WO2011123708, WO2014093908 and WO2016/044745, each of which are hereby incorporated by reference in its entirety.

In certain embodiments, the CAR variable region locus contains unrearranged human Ig heavy chain variable region gene segments. In some embodiments, the unrearranged human Ig variable region gene segments comprise a plurality of human $V_H$ segments, one or more human $D_H$ segments and one or more human $J_H$ segments. In some embodiments, the unrearranged human Ig variable region gene segments comprise at least 3 $V_H$ gene segments, at least 18 $V_H$ gene segments, at least 20 $V_H$ gene segments, at least 30 $V_H$ gene segments, at least 40 $V_H$ gene segments, at least 50 $V_H$ gene segments, at least 60 $V_H$ gene segments, at least 70 $V_H$ gene segments, or at least 80 $V_H$ gene segments. In some embodiments, the unrearranged human Ig gene segments include all of the human $D_H$ gene segments. In some embodiments, the CAR variable region further comprises TCRβ variable region gene segments (e.g., V, D and/or J gene segments). In one embodiment, the CAR variable region further comprises distal TCR Vβ gene segments, e.g., TCR Vβ31 gene segment. In another embodiment, the distal TCR Vβ gene segments, e.g., TCR Vβ31 gene segment, has been functionally inactivated or deleted. In some embodiments, the unrearranged human Ig gene segments include all of the human $J_H$ gene segments. Exemplary variable regions comprising Ig heavy chain gene segments are provided, for example, in Macdonald et al., *Proc. Natl. Acad. Sci. USA* 111:5147-52 and supplemental information, which is hereby incorporated by reference.

In some embodiments, the human immunoglobulin heavy chain variable region gene segments rearrange during T cell development to generate rearranged human heavy chain variable region genes in the T cells of the non-human organism. In some embodiments, the non-human animal provided herein has a greater percentage of V-D and/or D-J immunoglobulin heavy chain junctions containing non-template additions than a corresponding non-human animal that does not have a nucleic acid encoding an exogenous TdT in its genome. In some embodiments, the percentage of V-D and/or D-J immunoglobulin heavy chain junctions containing non-template additions in the genetically modified non-human animals provided herein is greater than percentage of V-D and/or D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-D immunoglobulin heavy chain junctions not containing non-template additions than a corresponding non-human animal that does not have a nucleic acid encoding an exogenous TdT in its genome. In some embodiments, the percentage of V-D and/or D-J immunoglobulin heavy chain junctions not containing non-template additions in the genetically modified non-human animals provided herein is less than percentage of V-D and/or D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J immunoglobulin heavy chain junctions containing at least 1 N-addition than a corresponding non-human animal that does not have a nucleic acid encoding an exogenous TdT in its genome. In some embodiments, the percentage of V-D and/or D-J immunoglobulin heavy chain junctions containing at least 1 N-addition in the genetically modified non-human animals provided herein is greater than percentage of V-D and/or D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J immunoglobulin heavy chain junctions containing at least 2 N-additions than a corresponding non-human animal that does not have a nucleic acid encoding an exogenous TdT in its genome. In some embodiments, the percentage of V-D and/or D-J immunoglobulin heavy chain junctions containing at least 2 N-additions in the genetically modified non-human animals provided herein is greater than percentage of V-D and/or D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J immunoglobulin heavy chain junctions containing at least 3 N-additions than a corresponding non-human animal that does not have a nucleic acid encoding an exogenous TdT in its genome. In some embodiments, the percentage of V-D and/or D-J immunoglobulin heavy chain junctions containing at least 3 N-additions in the genetically modified non-human animals provided herein is greater than percentage of V-D and/or D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-D and/or D-J immunoglobulin heavy chain junctions containing at least 4 N-additions than a corresponding non-human animal that does not have a nucleic acid encoding an exogenous TdT in its genome. In some embodiments, the percentage of V-D and/or D-J immunoglobulin heavy chain junctions containing at least 4 N-additions in the genetically modified non-human animals provided herein is greater than percentage of V-D and/or D-J immunoglobulin heavy chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-D and/or D-J immunoglobulin heavy chain junctions in the animal comprise non-template additions. In some embodiments, the non-human animal has a greater frequency of unique immunoglobulin heavy chain CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%.

In some embodiments, the CAR variable gene locus comprising unrearranged human Ig heavy chain variable region gene segments also includes human Ig heavy chain variable region intergenic sequences. In some embodiments, the CAR variable gene locus includes non-human (e.g., rodent, rat, mouse) Ig heavy chain variable region intergenic sequences. In some embodiments, the CAR variable gene locus includes human or non-human (e.g., rodent, rat, mouse) TCRβ variable region intergenic sequences. For example, in some embodiments the unrearranged variable region of the CAR locus comprises one or more (e.g., 1, 2, 3, 4, 5, 6, 7, 8, 9, 10, 11, 12, 13, 14, 15, 16, 17, 18, 19 or 20) trypsinogen (TRY) genes (e.g., TRY genes and/or pseudogenes normally present in the TCRβ variable region locus). In some embodiments, the TRY genes are non-human, e.g., mouse TRY genes. In some embodiments, the mouse TRY genes are selected from the group consisting of Try1, Try2, Try3, Try4, Try5, Try6, Try7, Try8, Try9, Try10, Try11, Try12, Try13, Try14, Try15, Try16, Try17, Try18, Try19 and Try20. In some embodiments, one or more TRY genes are located upstream of the $V_H$ segments of the unrearranged variable region. In some embodiments, one or more TRY genes are located downstream of the $V_H$ segments and upstream of the $D_H$ segments of the unrearranged variable region. In some embodiments, Try1-7 are located upstream of the $V_H$ segments of the unrearranged variable region and Try 8-20 are located downstream of the $V_H$ segments and upstream of the $D_H$ segments of the unrearranged variable region. Additional information regarding the TRY genes located in the human and/or mouse TCRβ locus is provided in Glusman et al., *Immunity* 15:337-349 (2001) and Skok et al., *Nature Immunology* 8:378-387 (2007), each of which is incorporated by reference. In some embodiments, the CAR gene locus comprises non-human regulatory elements (e.g., non-human promoters and/or enhancers). In some embodiments, the non-human regulatory elements are rodent regulatory elements (e.g., rat or mouse promoters or enhancers). In some embodiments, the CAR locus comprises an IgM enhancer (Eμ). In some embodiments, the IgM enhancer is a non-human Eμ (e.g., a rodent Eμ, such as a mouse or rat Eμ).

In certain embodiments, the CAR variable region locus contains unrearranged human Ig κ variable region gene segments. In some embodiments, the unrearranged human immunoglobulin variable region gene segments comprise a plurality of human $V_κ$ segments and one or more human $J_κ$ segments. In some embodiments, the immunoglobulin variable region gene segments comprise four functional $V_κ$ segments and all human $J_κ$ segments. In some embodiments, the immunoglobulin variable region gene segments comprise 16 functional $V_κ$ segments and all human $J_κ$ segments. In some embodiments, the unrearranged human immunoglobulin variable region gene segments comprise all of the human Vκ segments and all human $J_κ$ segments (e.g., all functional human Vκ segments and $J_κ$ segments). Exemplary variable regions comprising Ig κ gene segments are provided, for example, in Macdonald et al., *Proc. Natl. Acad. Sci. USA* 111:5147-52 and supplemental information, which is hereby incorporated by reference. In some embodiments, the unrearranged human immunoglobulin variable region gene segments comprise all of the human Jκ segments. In some embodiments, the CAR variable region further comprises TCRα variable region gene segments (e.g., V, and/or J gene segments).

In some embodiments, the human immunoglobulin κ variable region gene segments rearrange during T cell development to generate rearranged human κ variable region genes in the T cells of the non-human organism. In some embodiments, the non-human animal provided herein has a greater percentage of V-J immunoglobulin κ chain junctions containing non-template additions than a corresponding non-human animal that does not have a nucleic acid encoding an exogenous TdT in its genome. In some embodiments, the percentage of V-J immunoglobulin κ chain junctions containing non-template additions in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-J immunoglobulin κ chain junctions not containing non-template additions than a corresponding non-human animal that does not have a nucleic acid encoding an exogenous TdT in its genome. In some embodiments, the percentage of V-J immunoglobulin κ chain junctions not containing non-template additions in the genetically modified non-human animals provided herein is less than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin κ chain junctions containing at least 1 N-addition than a corresponding non-human animal that does not have a nucleic acid encoding an exogenous TdT in its genome. In some embodiments, the percentage of V-J immunoglobulin κ chain junctions containing at least 1 N-addition in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin κ chain junctions containing at least 2 N-additions than a corresponding non-human animal that does not have a nucleic acid encoding an exogenous TdT in its genome. In some embodiments, the percentage of V-J immunoglobulin κ chain junctions containing at least 2 N-additions in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin κ chain junctions containing at least 3 N-additions than a corresponding non-human animal that does not have a nucleic acid encoding an exogenous TdT in its genome. In some embodiments, the percentage of V-J immunoglobulin κ chain junctions containing at least 3 N-additions in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin κ chain junctions containing at least 4 N-additions than a corresponding non-human animal that does not have a nucleic acid encoding an exogenous TdT in its genome. In some embodiments, the percentage of V-J immunoglobulin κ chain junctions containing at least 4 N-additions in the genetically modified non-human animals provided herein is greater than percentage of V-J immunoglobulin κ chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-J immunoglobulin κ chain junctions in the animal comprise non-template additions. In some embodiments, the non-human animal has a greater frequency of unique immunoglobulin κ chain CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%. In some embodiments, the non-human animal provided herein has at least 900, 1000, 1100, 1200, 1300, 1400, 1500 or 1700 unique immunoglobulin κ chain CDR3 sequences per 10,000 immunoglobulin κ chain CDR3 sequences.

In certain embodiments, the CAR variable region locus contains unrearranged human Ig λ variable region gene segments. In some embodiments, the unrearranged human immunoglobulin variable region gene segments comprise a plurality of human $V_\lambda$ segments and one or more human $J_\lambda$ segments. In some embodiments, the unrearranged human immunoglobulin variable region gene segments comprise all of the human $V_\lambda$ segments (e.g., all functional human $V_\lambda$ segments). In some embodiments, the unrearranged human immunoglobulin variable region gene segments comprise all of the human $J_\lambda$ segments. In some embodiments, the CAR variable region further comprises TCRα variable region gene segments (e.g., V, and/or J gene segments). Exemplary variable regions comprising Ig λ gene segments are provided, for example, U.S. Pat. Pub. Nos. 2012/0073004 and 2002/0088016, each of which is hereby incorporated by reference.

In some embodiments, the human immunoglobulin λ variable region gene segments rearrange during T cell development to generate rearranged human λ variable region genes in the T cells of the non-human organism. In some embodiments, the non-human animal provided herein has a greater percentage of V-J immunoglobulin λ chain junctions containing non-template additions than a corresponding non-human animal that does not have a nucleic acid encoding an exogenous TdT in its genome. In some embodiments, the percentage of V-J immunoglobulin λ chain junctions containing non-template additions in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a lower percentage of V-J immunoglobulin λ chain junctions not containing non-template additions than a corresponding non-human animal that does not have a nucleic acid encoding an exogenous TdT in its genome. In some embodiments, the percentage of V-J immunoglobulin λ chain junctions not containing non-template additions in the genetically modified non-human animals provided herein is less than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin λ chain junctions containing at least 1 N-addition than a corresponding non-human animal that does not have a nucleic acid encoding an exogenous TdT in its genome. In some embodiments, the percentage of V-J immunoglobulin λ chain junctions containing at least 1 N-addition in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin λ chain junctions containing at least 2 N-additions than a corresponding non-human animal that does not have a nucleic acid encoding an exogenous TdT in its genome. In some embodiments, the percentage of V-J immunoglobulin λ chain junctions containing at least 2 N-additions in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin λ chain junctions containing at least 3 N-additions than a corresponding non-human animal that does not have a nucleic acid encoding an exogenous TdT in its genome. In some embodiments, the percentage of V-J immunoglobulin λ chain junctions containing at least 3 N-additions in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, the non-human animal provided herein has a greater percentage of V-J immunoglobulin λ chain junctions containing at least 4 N-additions than a corresponding non-human animal that does not have a nucleic acid encoding an exogenous TdT in its genome. In some embodiments, the percentage of V-J immunoglobulin λ chain junctions containing at least 4 N-additions in the genetically modified non-human animals provided herein is greater than percentage of V-J immunoglobulin λ chain junctions in the corresponding non-human animal by at least 1%, 2%, 3%, 4%, 5%, 6%, 7%, 8%, 9%, 10%, 15%, 20%, 30% or 40%. In some embodiments, at least 10%, 15%, 20%, 25%, 30%, 35% or 40% of the V-J immunoglobulin λ chain junctions in the animal comprise non-template additions. In some embodiments, the non-human animal has a greater frequency of unique immunoglobulin λ chain CDR3 sequences then a corresponding non-human animal by at least 1%, 2%, 3%, 4%, 5%, 6%, 7%, 8%, 9%, 10%, 15%, 20%, 25%, 30%, 35%, 40%, 40%, 45%, 50%, 60%, 70%, 80%, 90% or 100%. In some embodiments, the non-human animal provided herein has at least 150, 160, 170, 180, 190, 200, 210, 220, 230, 240, 250, 260, 270, 280, 290 or 300 unique immunoglobulin λ chain CDR3 sequences per 10,000 immunoglobulin λ chain CDR3 sequences.

In some embodiments, the CAR variable gene locus containing unrearranged human Ig light chain variable region gene segments also includes human Ig light chain variable region intergenic sequences (e.g., κ variable region intergenic sequences and/or λ variable region intergenic sequences). In some embodiments, the CAR variable gene locus includes non-human (e.g., rodent, rat, mouse) Ig light chain variable region intergenic sequences (e.g., κ variable region intergenic sequences and/or λ variable region intergenic sequences). In some embodiments, the CAR variable gene locus includes human or non-human (e.g., rodent, rat, mouse) TCRα variable region intergenic sequences. In some embodiments, the CAR gene locus comprises non-human regulatory elements (e.g., non-human promoters and/or enhancers). In some embodiments, the non-human regulatory elements are rodent regulatory elements (e.g., rat or mouse promoters or enhancers).

In some embodiments, the CAR variable region locus is a rearranged variable region locus comprising a Ig heavy chain variable region gene (a universal heavy chain variable region). In some embodiments, the rearranged Ig heavy chain variable region gene is a human rearranged Ig heavy chain variable region gene. Use of universal heavy chain variable regions facilitate the generation of bispecific antibodies in which at least one antigen-binding domain has specificity for a peptide/MHC complex. Exemplary rearranged Ig heavy chain variable regions are provided in U.S. Patent Pub. No. 2014/0245468, which is hereby incorporated by reference.

In some embodiments, the CAR variable region locus is a rearranged variable region locus comprising a Ig light chain variable region gene (a universal light chain variable region). In some embodiments, the rearranged Ig light chain variable region gene is a human rearranged Ig light chain variable region gene. Use of universal light chain variable regions facilitate the generation of bispecific antibodies in which at least one antigen-binding domain has binding specificity for a peptide/MHC complex. Exemplary rearranged Ig heavy chain variable regions are provided in U.S. Patent Pub. No. 2013/0185821, which is hereby incorporated by reference.

Other Genetic Modifications

In some embodiments, the genetically modified non-human animals and ES cells described herein that express exogenous TdT, humanized TCRs or CARs also express and/or comprise in their genome loci encoding humanized MHC class I α chain polypeptides (e.g., humanized HLA-A, HLA-B, HLA-C, HLA-E, HLA-F, HLA-g, HLA-K and/or HLA-L). In some embodiments, the humanized MHC class I α chain polypeptide is fully human. In some embodiments, the humanized MHC class I α chain polypeptide comprises a human extracellular domain (e.g., a human α1, α2, and α3 domains) and a cytoplasmic domain of endogenous species origin. Humanized MHC class I α chain polypeptides, loci encoding humanized MHC class I α chain polypeptides and non-human animals expressing humanized MHC class I α chain polypeptides are described in U.S. Pat. Pub. Nos. 2013/0111617, 2013/0185819 and 2014/0245467, each of which is incorporated by reference herein.

In some embodiments, the genetically modified non-human animals and ES cells described herein that express exogenous TdT, humanized TCRs or CARs also express and/or comprise in their genome a locus encoding humanized β-2-microglobulin polypeptide. Humanized β-2-microglobulin polypeptides, loci encoding humanized β-2-microglobulin polypeptides and non-human animals expressing humanized β-2-microglobulin polypeptides are described in U.S. Pat. Pub. Nos. 2013/0111617 and 2013/0185819, each of which is incorporated by reference herein.

In some embodiments, the genetically modified non-human animals and ES cells described herein that express exogenous TdT, humanized TCRs or CARs also express and/or comprise in their genome a loci encoding humanized MHC class II α chain polypeptides (e.g., humanized HLA-DMA, HLA-DOA, HLA-DPA, HLA-DQA and/or HLA-DRA). In some embodiments, the humanized MHC class II α chain polypeptide is fully human. In some embodiments, the humanized MHC class II α chain polypeptide comprises a human extracellular domain and a cytoplasmic domain of endogenous species origin. Humanized MHC class II α chain polypeptides, loci encoding humanized MHC class II α chain polypeptides and non-human animals expressing humanized MHC class II α chain polypeptides are described in U.S. Pat. Nos. 8,847,005 and 9,043,996 and U.S. Pat. Pub. No. 2014/0245467, each of which is incorporated by reference herein.

In some embodiments, the genetically modified non-human animals and ES cells described herein that express exogenous TdT, humanized TCRs or CARs also express and/or comprise in their genome a loci encoding humanized MHC class II β chain polypeptides (e.g., humanized HLA-DMB, HLA-DOB, HLA-DPB, HLA-DQB and/or HLA- DRB). In some embodiments, the humanized MHC class II β chain polypeptide is fully human. In some embodiments, the humanized MHC class II β chain polypeptide comprises a human extracellular domain and a cytoplasmic domain of endogenous species origin. Humanized MHC class II β chain polypeptides, loci encoding humanized MHC class II β chain polypeptides and non-human animals expressing humanized MHC class II (3 chain polypeptides are described in U.S. Pat. Nos. 8,847,005 and 9,043,996 and U.S. Pat. Pub. No. 2014/0245467, each of which is incorporated by reference herein.

Genetically modified non-human animals comprising exogenous TdT, humanized TCR loci and humanized MHC I and/or MHC II (MHC IIα/IIβ) loci can be generated by breeding using conventional methods; alternatively, they can be generated by homologous recombination in ES cells already comprising one or more genetically engineered loci (e.g., humanized TCR loci), and generating a non-human animal from said ES cells.

Genetically modified non-human animals comprising exogenous TdT, humanized CAR loci and humanized MHC I and/or MHC II (MHC IIα/IIβ) loci can be generated by breeding using conventional methods; alternatively, they can be generated by homologous recombination in ES cells already comprising one or more genetically engineered loci (e.g., humanized CAR loci), and generating a non-human animal from said ES cells.

In some embodiments, the genetically modified non-human animals and ES cells described herein that express exogenous TdT, humanized TCRs or CARs also express and/or comprise in their genome a locus encoding a humanized CD8 α chain polypeptide. In some embodiments, the humanized CD8 α chain polypeptide is fully human. In some embodiments, the humanized CD8 α chain polypeptide comprises a human extracellular immunoglobulin domain and a cytoplasmic domain of endogenous species origin. Humanized CD8 α chain polypeptides, loci encoding humanized CD8 α chain polypeptides and non-human animals expressing humanized CD8 α chain polypeptides are described in U.S. Pat. Pub. Nos. 2014/0245466 which is incorporated by reference herein.

In some embodiments, the genetically modified non-human animals and ES cells described herein that express exogenous TdT, humanized TCRs or CARs also express and/or comprise in their genome a locus encoding a humanized CD8 β chain polypeptide. In some embodiments, the humanized CD8 β chain polypeptide is fully human. In some embodiments, the humanized CD8 β chain polypeptide comprises a human extracellular immunoglobulin domain and a cytoplasmic domain of endogenous species origin. Humanized CD8 β chain polypeptides, loci encoding humanized CD8 β chain polypeptides and non-human animals expressing humanized CD8 β chain polypeptides are described in U.S. Pat. Pub. Nos. 2014/0245466 which is incorporated by reference herein.

In some embodiments, the genetically modified non-human animals and ES cells described herein that express exogenous TdT, humanized TCRs or CARs also express and/or comprise in their genome a locus encoding a humanized CD4 polypeptide. In some embodiments, the humanized CD4 polypeptide is fully human. In some embodiments, the humanized CD4 polypeptide comprises at least one human extracellular immunoglobulin domain and a cytoplasmic domain of endogenous species origin. In some embodiments, the humanized CD4 polypeptide comprises at least a human D1 immunoglobulin domain, a human D2 immunoglobulin domain, and a human D3 immunoglobulin domain, and a cytoplasmic domain of endogenous species origin. In some embodiments, the humanized CD4 polypeptide comprises a human D1 immunoglobulin domain, a human D2 immunoglobulin domain, a human D3 immunoglobulin domain, a D4 immunoglobulin domain of endogenous species origin and a cytoplasmic domain of endogenous species origin. Humanized CD4 polypeptides, loci encoding humanized CD4 polypeptides and non-human animals expressing humanized CD4 polypeptides are described in U.S. Pat. Pub. Nos. 2014/0245466 which is incorporated by reference herein.

Genetically modified non-human animals comprising exogenous TdT, humanized TCR loci and humanized CD4 and/or CD8 (CD8α/CD8β) loci can be generated by breeding using conventional methods; alternatively, they can be generated by homologous recombination in ES cells already comprising one or more genetically engineered loci (e.g., humanized TCR loci), and generating a non-human animal from said ES cells.

Genetically modified non-human animals comprising exogenous TdT, humanized CAR loci and humanized CD4 and/or CD8 (CD8α/CD8β) loci can be generated by breeding using conventional methods; alternatively, they can be generated by homologous recombination in ES cells already comprising one or more genetically engineered loci (e.g., humanized CAR loci), and generating a non-human animal from said ES cells.

Methods of Using the Genetically Modified Non-Human Animals

In certain aspects, provided herein are methods of using the genetically modified non-human animals described herein to generate antigen binding proteins (e.g., antibodies, CARs, TCRs), cells expressing such antigen binding proteins (e.g., B cells, T cells, B cell hybridomas, T cell hybridomas) and nucleic acids encoding such antigen binding proteins or portions thereof (e.g., variable domains). In some embodiments, provided herein are methods of making more diverse antigen binding proteins (e.g., antibodies, CARs, TCRs). In some embodiments, provided herein are methods of making rearranged variable regions of antigen binding proteins (e.g., antibodies, CARs, TCRs) that have increased numbers of nucleotide additions.

In certain embodiments, the method comprises exposing a genetically modified non-human animal described herein that has been modified to express exogenous TdT and antibodies or antigen-binding fragments thereof having human variable domains to an antigen such that the genetically modified non-human animal produces an antibody or an antigen-binding fragment thereof comprising a human variable domain specific for the antigen.

In some embodiments the method comprises exposing a genetically modified non-human animal described herein that has been modified to express exogenous TdT and antibodies or antigen-binding fragments thereof having human variable domains to an antigen; and obtaining a B cell expressing an antibody or an antigen-binding fragment thereof comprising a human variable domain specific for the antigen from the non-human animal.

In some embodiments, the method comprises exposing a genetically modified non-human animal described herein that has been modified to express exogenous TdT and antibodies or antigen-binding fragments thereof having human variable domains to an antigen; obtaining a B cell expressing an antibody or an antigen-binding fragment thereof comprising a human variable domain specific for the antigen from the non-human animal; and making a hybridoma from the B cell.

In some embodiments, the method comprises exposing a genetically modified non-human animal described herein that has been modified to express exogenous TdT and antibodies or antigen-binding fragments thereof having human variable domains to an antigen; and obtaining a nucleic acid encoding a human immunoglobulin variable domain specific for the antigen from the non-human animal.

In certain embodiment, the method comprises exposing a genetically modified non-human animal described herein that has been modified to express exogenous TdT and antibodies or antigen-binding fragments thereof having human variable domains to an antigen; obtaining a B cell expressing an antibody or an antigen-binding fragment thereof comprising a human variable domain specific for the antigen from the non-human animal; optionally making a hybridoma from the B cell; and obtaining a nucleic acid encoding a human immunoglobulin variable domain specific for the antigen from the B cell or the hybridoma.

In some embodiments, the method comprises exposing a non-human animal described herein that has been modified to express exogenous TdT and antibodies or antigen-binding fragments thereof having human variable domains to an antigen; obtaining a B cell expressing an antibody or an antigen-binding fragment thereof comprising a human variable domain specific for the antigen from the non-human animal; optionally making a hybridoma from the B cell; obtaining a nucleic acid encoding a human immunoglobulin variable domain specific for the antigen from the B cell or the hybridoma; operably linking the nucleic acid encoding the immunoglobulin variable domain with a nucleic acid encoding a human immunoglobulin constant domain in a host cell; and culturing the host cell under conditions such that the host cell expresses a human antibody comprising the immunoglobulin variable domain and the immunoglobulin constant domain.

In some embodiments, the method comprises exposing a genetically modified non-human animal described herein that has been modified to express exogenous TdT and TCR having human variable domains to an antigen comprising a peptide or a nucleic acid encoding an antigen comprising a peptide such that the peptide is presented on a MHC in the non-human animal; and obtaining a T cell expressing a TCR specific for the peptide presented on the MHC from the genetically modified non-human animal.

In some embodiments, the method comprises exposing a genetically modified non-human animal described herein that has been modified to express exogenous TdT and TCR having human variable domains to an antigen comprising a peptide or a nucleic acid encoding an antigen comprising a peptide such that the peptide is presented on a MHC in the non-human animal; obtaining a T cell expressing a TCR specific for the peptide presented on the MHC from the genetically modified non-human animal; and making a T cell hybridoma from the T cell.

In some embodiments, the method comprises exposing a non-human animal described herein that has been modified to express exogenous TdT and TCR having human variable domains to an antigen comprising a peptide or a nucleic acid encoding an antigen comprising a peptide such that the peptide is presented on a MHC in the non-human animal; obtaining a T cell expressing a TCR specific for the peptide presented on the MHC from the genetically modified non-human animal; and isolating a nucleic acid encoding a human TCR variable domain of the TCR from the T cell.

In some embodiments, the method comprises exposing a non-human animal described herein that has been modified to express exogenous TdT and TCR having human variable domains to an antigen comprising a peptide or a nucleic acid encoding an antigen comprising a peptide such that the peptide is presented on a MHC in the non-human animal; obtaining a T cell expressing a TCR specific for the peptide presented on the MHC from the genetically modified non-human animal; isolating a nucleic acid encoding a TCR variable domain of the TCR from the T cell; and operably linking the nucleic acid encoding the TCR variable domain with a TCR constant domain in a cell such that the cell expresses a TCR comprising the TCR variable domain and the TCR constant domain.

In some embodiments, the method comprises exposing a genetically modified non-human animal described herein that has been modified to express exogenous TdT and CAR having human variable domains to an antigen comprising a peptide or a nucleic acid encoding an antigen comprising a peptide such that the peptide is presented on a MHC in the non-human animal; and obtaining a T cell expressing a CAR specific for the peptide presented on the MHC from the genetically modified non-human animal.

In some embodiments, the method comprises exposing a genetically modified non-human animal described herein that has been modified to express exogenous TdT and CAR having human variable domains to an antigen comprising a peptide or a nucleic acid encoding an antigen comprising a peptide such that the peptide is presented on a MHC in the non-human animal; obtaining a T cell expressing a CAR specific for the peptide presented on the MHC from the genetically modified non-human animal; and making a T cell hybridoma from the T cell.

In some embodiments, the method comprises exposing a non-human animal described herein that has been modified to express exogenous TdT and CAR having human variable domains to an antigen comprising a peptide or a nucleic acid encoding an antigen comprising a peptide such that the peptide is presented on a MHC in the non-human animal; obtaining a T cell expressing a chimeric antigen receptor (CAR) specific for the peptide presented on the MHC from the genetically modified non-human animal; and isolating a nucleic acid encoding a human TCR variable domain of the CAR from the T cell.

In some embodiments, the method comprises exposing a non-human animal described herein that has been modified to express exogenous TdT and CAR having human variable domains to an antigen comprising a peptide or a nucleic acid encoding an antigen comprising a peptide such that the peptide is presented on a MHC in the non-human animal; obtaining a T cell expressing a chimeric antigen receptor (CAR) specific for the peptide presented on the MHC from the genetically modified non-human animal; isolating a nucleic acid encoding a human immunoglobulin variable domain of the CAR from the T cell; and operably linking the nucleic acid encoding the human immunoglobulin variable domain with a human immunoglobulin constant domain in a cell such that the cell expresses an antibody comprising the human immunoglobulin variable domain and the human immunoglobulin constant domain.

In certain embodiments, the methods described herein include a step in which a non-human animal described herein is exposed to an antigen (immunized) in order to induce an immune response (e.g., a B cell immune response and/or a T cell immune response). In some embodiments the genetically modified non-human animal is immunized with a whole protein antigen or a fragment thereof. Rodents can be immunized by any method known in the art (see, for example, Harlow and Lane (1988) Antibodies: A Laboratory Manual 1988 Cold Spring Harbor Laboratory; Malik and Lillehoj (1994) Antibody Techniques, Academic Press, CA).

In some embodiments, the genetically modified non-human animal is exposed to the antigen by administering to the non-human animal a virus (e.g., a retrovirus, an adenovirus, a vaccinia virus or a lentivirus) comprising a nucleic acid sequence encoding the antigen. Methods for viral vaccination are provided, for example, in U.S. Pat. Nos. 6,001,349, 8,663,622, 8,691,502, 8,377,688, as well as Precopio et al., *JEM* 204:1405-1416 (2007), each of which is hereby incorporated by reference in its entirety. In some embodiments, the non-human animal is administered the virus directly. In some embodiments, a cell (e.g., an antigen presenting cell, such as a dendritic cell) is infected with the virus in vitro or ex vivo which is then administered to the non-human animal. In some embodiments, the virus encodes a peptide/MHC complex (e.g., a single-chain peptide/MHC complex). Examples of single-chain peptide/MHC based vaccines are provided in Truscott et al., *J. Immunol.* 178: 6280-6289 (2007), EP1773383, Kim et al., *Vaccine* 30:2178-2186 (2012), Kim et al., *J. Immunol.* 184:4423-4430 (2010), each of which are hereby incorporated by reference.

In some embodiments, the genetically modified non-human animal is exposed to the antigen by administering to the animal a nucleic acid encoding the antigen. In some embodiments, the non-human animal is administered a nucleic acid encoding a single chain peptide/MHC complex. Examples of single-chain peptide/MHC based vaccines are provided in Truscott et al., *J. Immunol.* 178:6280-6289 (2007), EP1773383, Kim et al., *Vaccine* 30:2178-2186 (2012), Kim et al., *J. Immunol.* 184:4423-4430 (2010), each of which are hereby incorporated by reference. In certain embodiments, the nucleic acid is a DNA vector. The delivery of nucleic acids can be by any technique known in the art including viral mediated gene transfer and liposome mediated gene transfer. A polynucleotide of interest is associated with a liposome to form a gene delivery vehicle as described in, for example, U.S. Pat. Nos. 6,770,291, 7,001,614, 6,749,863, 5,512,295 and 7,112,338, each of which is hereby incorporated by reference. In some embodiments, the nucleic acid is an mRNA vector. Exemplary methods for generating and administering mRNA vectors are described in, for example, U.S. Pat. No. 8,278,036 and U.S. Pat. Pub. Nos. 2013/151736 and 2012/135805, each of which is hereby incorporated by reference.

In some embodiments, antigen is a cancer-associated antigen. Examples of cancer-associated antigens include, but are not limited to, adipophilin, AIM-2, ALDH1A1, alpha-actinin-4, alpha-fetoprotein ("AFP"), ALK, ANKRD30A, ARTC1, B-RAF, BAGE-1, BCLX (L), BCR-ABL fusion protein b3a2, beta-catenin, BING-4, BIRC7, CA-125, CA9, CALCA, carcinoembryonic antigen ("CEA"), CALR, CASP-5, CASP-8, CCR5, CD19, CD20, CD22, CD27, CD274, CD30, CD33, CD38, CD40, CD44, CD45, CD52, CD56, CD79, Cdc27, CDK12, CDK4, CDKN2A, CEA, CLEC12A, CLPP, COA-1, CPSF, CSNK1A1, CTAG1, CTAG2, cyclin D1, Cyclin-A1, dek-can fusion protein, DKK1, EFTUD2, EGFR, EGFR variant III, Elongation factor 2, ENAH (hMena), Ep-CAM, EpCAM, EphA2, EphA3, epithelial tumor antigen ("ETA"), ERBB3, ERBB4, ETV6-AML1 fusion protein, EZH2, FCRL3, FGF5, FLT3-ITD, FN1, FOLR1, G250/MN/CAIX, GAGE-1,2,8, GAGE-3,4,5,6,7, GAS7, glypican-3, GnTV, gp100/Pme117, GPNMB, GM3, GPR112, IL3RA, HAUS3, Hepsin, HER-2/neu, HERV-K-MEL, HLA-A11, HLA-A2, HLA-DOB, hsp70-2, IDO1, IGF2B3, IL13Ralpha2, Intestinal carboxyl esterase, K-ras, Kallikrein 4, KIF20A, KIT, KK-LC-1, KKLC1, KMHN1 also known as CCDC110, KRAS, LAGE-1, LDLR-fucosyltransferaseAS fusion protein, Lengsin, LGR5, LMP2, M-CSF, MAGE-A1, MAGE-A10, MAGE-A12, MAGE-A2, MAGE-A3, MAGE-A4, MAGE-A6, MAGE-A9, MAGE-C1, MAGE-C2, malic enzyme, mammaglobin-A, MART2, MATN, MC1R, MCSP, mdm-2, MEL Melan-A/MART-1, Meloe, Midkine, MMP-2, MMP-7, MUC1, MUC2, MUC3, MUC4, MUC5, MUCSAC, MUC16, mucin, MUM-1, MUM-2, MUM-3, Myosin, Myosin class I, N-raw, NA88-A, neo-PAP, NFYC, NY-BR-1, NY-ESO-1/LAGE-2, OA1, OGT, OS-9, OX40, P polypeptide, p53, PAP, PAX3, PAXS, PBF, PLAC1, PMEL, pml-RARalpha fusion protein, polymorphic epithelial mucin ("PEM"), PPP1R3B, PRAME, PRDX5, PRLR, PSA, PSMA, PTPRK, RAB38/NY-MEL-1, RAGE-1, RBAF600, RET, RGSS, RhoC, RNF43, ROR1, RU2AS, SAGE, SART1, SART3, secemin 1, SIRT2, SLAMF7, SLC39A6, SNRPD1, SOX10, Sp17, SPA17, SSX-2, SSX-4, STEAP1, STEAP2, survivin, SYT-SSX1 or -SSX2 fusion protein, TAG-1, TAG-2, Telomerase, TERT, TGF-betaRII, Thompson-nouvelle antigen, TMPRSS2, TNFRSF17, TPBG, TRAG-3, Triosephosphate isomerase, TRP-1/gp75, TRP-2, TRP2-INT2, tyrosinase, tyrosinase ("TYR"), UPK3A, VEGF, VTCN1, WT1, XAGE-1b/GAGED2a. In some embodiments, the antigen is a neo-antigen.

In some embodiment, the antigen is an antigen expressed by an infectious pathogen. In some embodiments, the pathogen is a virus, a bacteria, a fungus, a helminth, or a protozoa. Nonlimiting examples of viruses include HIV, hepatitis A, hepatitis B, hepatitis C, herpes virus (e.g., HSV-1, HSV-2, CMV, HAV-6, VZV, Epstein Barr virus), adenovirus, influenza virus, flavivirus, echovirus, rhinovirus, coxsackie virus, coronavirus, respiratory syncytial virus, mumps virus, rotavirus, measles virus, rubella virus, parvovirus, vaccinia virus, HTLV, dengue virus, papillomavirus, molluscum virus, poliovirus, rabies virus, JC virus, ebola virus, and arboviral encephalitis virus antigen. In some embodiments, the parasite is malaria. In some embodiments, pathogen is *Aspergillus, Brugia, Candida, Chlamydia, Coccidia, Cryptococcus, Dirofilaria, Gonococcus, Histoplasma, Klebsiella, Legionella, Leishmania, Meningococci, Mycobacterium, Mycoplasma, Paramecium, Pertussis, Plasmodium, Pneumococcus, Pneumocystis, Pseudomonas, Rickettsia, Salmonella, Shigella, Staphylococcus, Streptococcus, Toxoplasma* and *Vibriocholerae*. Exemplary species include *Neisseria gonorrhea, Mycobacterium tuberculosis, Candida albicans, Candida tropicalis, Trichomonas vaginalis, Haemophilus vaginalis,* Group B *Streptococcus* sp., *Microplasma hominis, Hemophilus ducreyi, Granuloma inguinale, Lymphopathia venereum, Treponema pallidum, Brucella abortus, Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani, Clostridium botulinum*; or, a fungus, such as, e.g., *Paracoccidioides brasiliensis*; or other pathogen, e.g., *Plasmodium falciparum*.

In some embodiments of the methods described herein, the method includes the step of obtaining a T cell and/or or B cell from the genetically modified non-human animal. In certain embodiments, any method known in the art can be used to obtain such cells. For example, such T cells and/or B cells can be obtained from the spleen, lymph nodes and/or peripheral blood of the animal. Such T cells and/or B cells can be screened for binding specificity using methods available in the art.

In some embodiments, the methods described herein include the step of making a B cell hybridoma from a B cell. Methods useful for making a B cell hybridoma are known in the art and described, for example, in Harlow and Lane (1988) Antibodies: A Laboratory Manual 1988 Cold Spring Harbor Laboratory; Malik and Lillehoj (1994) Antibody Techniques, Academic Press, CA, which is hereby incorporated by reference.

In some embodiments, the methods described herein include the step of making a T cell hybridoma from a T cell. Methods useful for making a T cell hybridoma are known in the art and described, for example, in Hedrick et al., *Cell* 30:141-152 (1982) and Kruisbeek *Curr. Protoc. Immunol.* Chapter 3 (2001) and White et al., *Methods in Molecular Biology* 134:185-193 (2000), each of which is hereby incorporated by reference.

In some embodiments, the methods provided herein include the step of isolating a nucleic acid encoding an Ig or TCR variable region. In some embodiments of the methods described herein, any method can be used to isolate the nucleic acid encoding the Ig or TCR variable region.

In some embodiments, the step of isolating the nucleic acid comprises making a B cell or T cell hybridoma from a B cell or T cell respectively and isolating the nucleic acid from the hybridoma. In some embodiments, the nucleic acid is isolated using a nucleic acid amplification process. For example, in some embodiments the nucleic acid amplification process is polymerase chain reaction (PCR), ligase chain reaction (LCR), strand displacement amplification (SDA), transcription mediated amplification (TMA), self-sustained sequence replication (3SR), Qβ replicase based amplification, nucleic acid sequence-based amplification (NASBA), repair chain reaction (RCR), boomerang DNA amplification (BDA) or rolling circle amplification (RCA).

In some embodiments, the nucleic acid is isolated by sequencing the rearranged Ig or TCR variable region gene in a B cell, T cell, B cell hybridoma or T cell hybridoma and synthesizing a nucleic acid sequence comprising the rearranged Ig or TCR variable region gene. Exemplary nucleic acid sequencing processes include, but are not limited to chain termination sequencing, sequencing by ligation, sequencing by synthesis, pyrosequencing, ion semiconductor sequencing, single-molecule real-time sequencing, 454 sequencing, and/or Dilute-'N'-Go sequencing.

When DNA fragments encoding heavy and/or light chain Ig variable regions are obtained, these DNA fragments can be further manipulated by standard recombinant DNA techniques, for example to convert the variable region genes to full-length antibody chain genes, to Fab fragment genes or to a scFv gene. In these manipulations, a variable region-encoding DNA fragment is operably linked to another DNA fragment encoding another protein, such as an antibody constant region or a flexible linker. The term "operably linked", as used in this context, is intended to mean that the two DNA fragments are joined such that the amino acid sequences encoded by the two DNA fragments remain in-frame.

The isolated DNA encoding the heavy chain variable region can be converted to a full-length heavy chain gene by operably linking the variable region-encoding DNA to another DNA molecule encoding heavy chain constant domain (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242, or Lefranc, The Immunoglobulin Handbook, London: Academic Press 2001) and DNA fragments encompassing these regions can be obtained by standard PCR amplification. The heavy chain constant domain can be, for example, an IgG1, IgG2, IgG3, IgG4, IgA, IgE, IgM or IgD constant domain. For a Fab fragment heavy chain gene, the $V_H$-encoding DNA can be operably linked to another DNA molecule encoding only the heavy chain CH1 constant region.

Thus, in some embodiments, the methods described herein include the step of operably linking a nucleic acid sequence encoding a heavy chain Ig variable domain with a nucleic acid sequence encoding a heavy chain Ig constant domain in a host cell such that the host cell expresses an Ig heavy chain polypeptide comprising the Ig heavy chain variable domain and the Ig heavy chain constant domain. In some embodiments, the method includes the step of operably linking a nucleic acid sequence encoding a light chain Ig variable domain with a nucleic acid sequence encoding a light chain Ig constant domain in a host cell such that the host cell expresses an Ig light chain polypeptide comprising the Ig light chain variable domain and the Ig heavy chain constant domain. In some embodiments, the method includes the step of operably linking a nucleic acid sequence encoding a heavy chain Ig variable domain with a nucleic acid sequence encoding a heavy chain Ig constant domain in a host cell and operably linking a nucleic acid sequence encoding a light chain Ig variable domain with a nucleic acid sequence encoding a light chain Ig constant domain in the host cell such that the host cell expresses an antibody having a heavy chain comprising the heavy chain Ig variable domain and the heavy chain Ig constant domain and a light chain comprising the light chain Ig variable domain and the light chain Ig constant domain. Ig variable regions can be linked with Ig constant regions using standard molecular biology techniques well known in the art. In some embodiments, any host cell capable of expressing an immunoglobulin polypeptide can be used. In some embodiments the cell is a CHO cell, a HEK-293 cell, a BHK cell, a NS0 cell, a SP2/0 cell or a Vero cell or a retinal cell expressing a viral nucleic acid sequence (e.g., PERC.6™ cell).

In some embodiments, the nucleic acid encoding the heavy chain constant domain encodes a constant domain that comprises a modified Fc domain (e.g., a mutation that alters the interaction between the Fc and a Fc receptor). For example, in some embodiments, the constant domain comprises modification to its Fc domain at position 235, 236, 237, 239, 265, 267, 268, 269, 270, 298, 326, 327, 330, 332, 350, 351, 366, 392, 394, 405 and/or 407 (using the EU numbering system). In some embodiments, the modification is selected from the group consisting of L235A, G236E, G237F, S239E, S239D, D265E, D265S, S267E, S267D, S267G, H268E, H268D, E269L, D270N, D270E, S298A, K326A, K326D, A327H, A327V, A327L, A330I, A330S, I332E, T350V, L351Y, T366L, K392M, K392L, T394W, F405A and/or Y407V (using the EU numbering system). In some embodiments, the constant domain comprises multiple modifications to its Fc domain. In some embodiments, the multiple modifications are selected from the group consisting of D270N/K326D, S239E/S298A/K326A/A327H, L235A/S239E/D265E/A327H, G236E/G237F/S239E, G237F/S239E/D265E, G327F/S239E/H268D, G236E/D270N/A327V/I332E, G237F/S239E/A327H, G237F/A327L/A330I, S239D/D265S/S298A/I332E, S239E/

D265S/H268D/I332E, S239E/D265S/I332E, S239E/S267E/H268D, S239E/A327L/A330I, D265E/S267D/A330S, S267G/H268E/D270E, H268D/E269L/S298A/K326A/A327H, H268D/K326A/A327H. Additional Fc modifications and combinations of Fc modifications are provided in U.S. Pat. Nos. 5,624,821, 5,648,260, 6,528,624, 6,737,056, 7,122,637, 7,183,387, 7,297,775, 7,317,091, 7,332,581, 7,632,497, 7,662,925, 7,695,936, 8,093,359, 8,216,805, 8,218,805, 8,388,955 and 8,937,158, and U.S. Patent Publication Nos. 2005/0054832, 2006/0222653, 2006/0275282, 2006/0275283, 2007/0190063, 2008/0154025, 2009/0042291 2013/0108623 and 2013/0089541, each of which is hereby incorporated by reference.

Antigen Binding Proteins

In certain aspects, provided herein are antigen binding proteins (e.g., antibodies, TCRs, CARs and antigen binding fragments thereof) obtainable and/or obtained according to a method described herein (e.g., using a non-human animal described herein).

In certain embodiments, the antigen binding molecules provided herein are able to specifically bind a target antigen with a dissociation constant of no greater than $10^{-6}$, $10^{-7}$, $10^{-8}$ or $10^{-9}$ M. In some embodiments, the binding affinity of the antigen binding protein to an antigen (as expressed by $K_D$) is at least 10 fold less, at least 100 fold less or at least 1000 fold less than the affinity of the antigen binding protein for an unrelated antigen. In some embodiments, the antigen binding protein binds to a peptide/MHC complex with a dissociation constant of no greater than $10^{-6}$, $10^{-7}$, $10^{-8}$ or $10^{-9}$ M. In some embodiments, the binding affinity of the antigen binding protein to a peptide/MHC complex (as expressed by $K_D$) is at least 10 fold less, at least 100 fold less or at least 1000 fold less than the affinity of the antigen binding protein for the peptide for the same MHC protein presenting an unrelated peptide. Standard assays to evaluate the binding ability of the antigen binding proteins are known in the art, including for example, ELISAs, Western blots and RIAs. The binding kinetics (e.g., binding affinity) of the antigen binding protein also can be assessed by standard assays known in the art, such as by Biacore analysis.

In some embodiments, the antigen comprises an epitope of and/or is a cancer-associated antigen. Examples of cancer-associated antigens include, but are not limited to, adipophilin, AIM-2, ALDH1A1, alpha-actinin-4, alpha-fetoprotein ("AFP"), ARTC1, B-RAF, BAGE-1, BCLX (L), BCR-ABL fusion protein b3a2, beta-catenin, BING-4, CA-125, CALCA, carcinoembryonic antigen ("CEA"), CASP-5, CASP-8, CD274, CD45, Cdc27, CDK12, CDK4, CDKN2A, CEA, CLPP, COA-1, CPSF, CSNK1A1, CTAG1, CTAG2, cyclin D1, Cyclin-AL dek-can fusion protein, DKK1, EFTUD2, Elongation factor 2, ENAH (hMena), Ep-CAM, EpCAM, EphA3, epithelial tumor antigen ("ETA"), ETV6-AML1 fusion protein, EZH2, FGF5, FLT3-ITD, FN1, G250/MN/CAIX, GAGE-1,2,8, GAGE-3,4,5,6,7, GAS7, glypican-3, GnTV, gp100/Pme117, GPNMB, HAUS3, Hepsin, HER-2/neu, HERV-K-MEL, HLA-A11, HLA-A2, HLA-DOB, hsp70-2, IDOL IGF2B3, IL13Ralpha2, Intestinal carboxyl esterase, K-ras, Kallikrein 4, KIF20A, KK-LC-1, KKLC1, KM-HN-1, KMHN1 also known as CCDC110, LAGE-1, LDLR-fucosyltransferaseAS fusion protein, Lengsin, M-CSF, MAGE-A1, MAGE-A10, MAGE-A12, MAGE-A2, MAGE-A3, MAGE-A4, MAGE-A6, MAGE-A9, MAGE-C1, MAGE-C2, malic enzyme, mammaglobin-A, MART2, MATN, MC1R, MCSP, mdm-2, MEL Melan-A/MART-1, Meloe, Midkine, MMP-2, MMP-7, MUC1, MUCSAC, mucin, MUM-1, MUM-2, MUM-3, Myosin, Myosin class I, N-raw, NA88-A, neo-PAP, NFYC, NY-BR-1, NY-ESO-1/LAGE-2, OA1, OGT, OS-9, P polypeptide, p53, PAP, PAXS, PBF, pml-RARalpha fusion protein, polymorphic epithelial mucin ("PEM"), PPP1R3B, PRAME, PRDX5, PSA, PSMA, PTPRK, RAB38/NY-MEL-1, RAGE-1, RBAF600, RGSS, RhoC, RNF43, RU2AS, SAGE, secernin 1, SIRT2, SNRPD1, SOX10, Sp17, SPA17, SSX-2, SSX-4, STEAP1, survivin, SYT-SSX1 or -SSX2 fusion protein, TAG-1, TAG-2, Telomerase, TGF-betaRII, TPBG, TRAG-3, Triosephosphate isomerase, TRP-1/gp75, TRP-2, TRP2-INT2, tyrosinase, tyrosinase ("TYR"), VEGF, WT1, XAGE-1b/GAGED2a. In some embodiments, the antigen is a neo-antigen.

In some embodiment, the antigen comprises an epitope of and/or is an antigen expressed by an infectious pathogen. In some embodiments, the pathogen is a virus, a bacteria, a fungus, a helminth, or a protozoa. Some nonlimiting examples of viruses include HPV, HBV, hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, and influenza virus. In some embodiments, the parasite is malaria. In some embodiments, pathogen is *Aspergillus, Brugia, Candida, Chlamydia, Coccidia, Cryptococcus, Dirofilaria, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma* and *Vibriocholerae*. Exemplary species include *Neisseria gonorrhea, Mycobacterium tuberculosis, Candida albicans, Candida tropicalis, Trichomonas vaginalis, Haemophilus vaginalis*, Group B *Streptococcus* sp., *Microplasma hominis, Hemophilus ducreyi, Granuloma inguinale, Lymphopathia venereum, Treponema pallidum, Brucella abortus. Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani, Clostridium botulinum*; or, a fungus, such as, e.g., *Paracoccidioides brasiliensis*; or other pathogen, e.g., *Plasmodium falciparum*.

In some embodiments, the antigen comprises an epitope of and/or is a protein that is the target of an autoreactive T cell in an inflammatory disease, skin or organ transplantation rejection, graft-versus-host disease (GVHD), or autoimmune diseases. Examples of autoimmune diseases include, for example, glomerular nephritis, arthritis, dilated cardiomyopathy-like disease, ulceous colitis, Sjogren syndrome, Crohn disease, systemic erythematodes, chronic rheumatoid arthritis, multiple sclerosis, psoriasis, allergic contact dermatitis, polymyosiis, pachyderma, periarteritis nodosa, rheumatic fever, vitiligo vulgaris, insulin dependent diabetes mellitus, Behcet disease, Hashimoto disease, Addison disease, dermatomyositis, myasthenia gravis, Reiter syndrome, Graves' disease, anaemia perniciosa, Goodpasture syndrome, sterility disease, chronic active hepatitis, pemphigus, autoimmune thrombopenic purpura, and autoimmune hemolytic anemia, active chronic hepatitis, Addison's disease, anti-phospholipid syndrome, atopic allergy, autoimmune atrophic gastritis, achlorhydra autoimmune, celiac disease, Cushing's syndrome, dermatomyositis, discoid lupus, erythematosis, Goodpasture's syndrome, Hashimoto's thyroiditis, idiopathic adrenal atrophy, idiopathic thrombocytopenia, insulin-dependent diabetes, Lambert-Eaton syndrome, lupoid hepatitis, some cases of lymphopenia, mixed connective tissue disease, pemphigoid, pemphigus vulgaris, pernicious anema, phacogenic uveitis, polyarteritis nodosa, polyglandular autosyndromes, primary biliary cirrhosis, primary sclerosing cholangitis, Raynaud's syndrome, relapsing polychondritis, Schmidt's syndrome, limited scleroderma (or crest syndrome), sympathetic ophthalmia, systemic lupus erythematosis, Takayasu's arteritis, temporal arteritis, thyrotoxicosis, type b insulin resistance, ulcerative colitis and Wegener's granulomatosis. Exemplary proteins include targeted by autoreactive T cells include, for example, p205, insulin, thyroid-stimulating hormone, tyrosinase, TRP1, and myelin.

In some embodiments, the antigen binding protein is an antibody. In some embodiments, the antibodies provided herein comprise human heavy chain variable domains. In some embodiments, the antibodies comprise human heavy chain constant domains. In some embodiments, the antibodies provided herein comprise a IgG1, IgG2, IgG3, IgG4, IgA, IgE, IgM or IgD constant domain. The sequences of human heavy chain constant domains are known in the art (see e.g., Kabat, E. A., et al. (1991) Sequences of Proteins of Immunological Interest, Fifth Edition, U.S. Department of Health and Human Services, NIH Publication No. 91-3242, or Lefranc, The Immunoglobulin Handbook, London: Academic Press 2001). In some embodiments, the antibodies provided herein lack a heavy chain constant domain or a portion thereof.

In some embodiments, the antibodies provided herein comprise a modified Fc domain (e.g., a mutation that alters the interaction between the Fc and a Fc receptor). For example, in some embodiments, the antibodies provided herein comprise modification to their Fc domain at position 235, 236, 237, 239, 265, 267, 268, 269, 270, 298, 326, 327, 330, 332, 350, 351, 366, 392, 394, 405 and/or 407 (using the EU numbering system). In some embodiments, the modification is selected from the group consisting of L235A, G236E, G237F, S239E, S239D, D265E, D265S, S267E, S267D, S267G, H268E, H268D, E269L, D270N, D270E, S298A, K326A, K326D, A327H, A327V, A327L, A330I, A330S, I332E, T350V, L351Y, T366L, K392M, K392L, T394W, F405A and/or Y407V (using the EU numbering system). In some embodiments, the antibodies comprise multiple modifications to their Fc domain. In some embodiments, the multiple modifications are selected from the group consisting of D270N/K326D, S239E/S298A/K326A/A327H, L235A/S239E/D265E/A327H, G236E/G237F/S239E, G237F/S239E/D265E, G327F/S239E/H268D, G236E/D270N/A327V/I332E, G237F/S239E/A327H, G237F/A327L/A330I, S239D/D265S/S298A/I332E, S239E/D265S/H268D/I332E, S239E/D265S/I332E, S239E/S267E/H268D, S239E/A327L/A330I, D265E/S267D/A330S, S267G/H268E/D270E, H268D/E269L/S298A/K326A/A327H, H268D/K326A/A327H.

Additional Fc modifications and combinations of Fc modifications are provided in U.S. Pat. Nos. 5,624,821, 5,648,260, 6,528,624, 6,737,056, 7,122,637, 7,183,387, 7,297,775, 7,317,091, 7,332,581, 7,632,497, 7,662,925, 7,695,936, 8,093,359, 8,216,805, 8,218,805, 8,388,955 and 8,937,158, and U.S. Patent Publication Nos. 2005/0054832, 2006/0222653, 2006/0275282, 2006/0275283, 2007/0190063, 2008/0154025, 2009/0042291 2013/0108623 and 2013/0089541, each of which is hereby incorporated by reference.

In some embodiments, the antibody is a bi-specific antibody. In some embodiments, the two antigen binding domains of the bi-specific antibody have distinct heavy chain variable domains but have identical light chain variable domains. In some embodiments, the Fc domains of the heavy chains comprise modifications to facilitate heavy chain heterodimer formation and/or to inhibit heavy chain homodimer formation. Such modifications are provided, for example, in U.S. Pat. Nos. 5,731,168, 5,807,706, 5,821,333, 7,642,228 and 8,679,785 and in U.S. Pat. Pub. No. 2013/0195849, each of which is hereby incorporated by reference.

In some embodiments, the antibodies provided herein have human light chain variable domains. In some embodiments, the light chain variable domains are λ light chain variable domains. In some embodiments, the light chain variable domains are κ light chain variable domains. In some embodiments, the antibodies have human light chain constant domains. In some embodiments, the light chain constant domains are λ light chain constant domains. In some embodiments, the light chain constant domains are κ light chain constant domains. The sequences of human light chain constant domains are known in the art (see e.g., Kabat, E. A., et al. (1991) Sequences of Proteins of Immunological Interest, Fifth Edition, U.S. Department of Health and Human Services, NIH Publication No. 91-3242, or Lefranc, The Immunoglobulin Handbook, London: Academic Press 2001).

In some embodiments, the antibodies described herein are intact antibodies. In some embodiments, the antibodies described herein are antibody fragments that retain antigen binding. In some embodiments, the antibody fragment is a Fab, Fab', F(ab')2, Fv, scFv, disulfide linked Fv, Fd, single-chain antibodies, isolated CDRH3 or another antibody fragment that retain at least a portion of the variable domain of an intact antibody.

In certain embodiments, the antigen binding protein is a CAR. In some embodiments, the CAR is membrane-bound. In some embodiments, the CAR is a soluble CAR (e.g., lacking a transmembrane or cytoplasmic domain). In some embodiments, such CARs comprise a first CAR polypeptide comprising an Ig heavy chain variable domain and a TCRβ constant domain and a second CAR polypeptide comprising an Ig light chain variable domain (e.g., an Ig κ variable domain or an Ig λ variable domain) and a TCRα constant domain. In some embodiments, the Ig heavy chain variable domain and/or the Ig light chain variable domain are human Ig variable domains. In some embodiments, the TCRβ constant domain and/or the TCRα constant domain are non-human constant domains (e.g., rat or mouse constant domains). In some embodiments, the TCRβ constant domain and/or the TCRα constant domain are human constant domains.

In certain embodiments, the antigen binding protein is a TCR. In some embodiments, the TCR is membrane-bound. In some embodiments, the TCR is a soluble TCR (e.g., lacking a transmembrane or cytoplasmic domain). In some embodiments, such TCRs comprise a first TCR polypeptide comprising a TCRβ variable domain and a TCRβ constant domain and a second TCR polypeptide comprising a TCRα variable domain and a TCRα constant domain. In some embodiments, the TCRα variable domain and/or the TCRβ variable domain are human TCR variable domains. In some embodiments, the TCRβ constant domain and/or the TCRα constant domain are non-human constant domains (e.g., rat or mouse constant domains). In some embodiments, the TCRβ constant domain and/or the TCRα constant domain are human constant domains.

Pharmaceutical Compositions

In certain embodiments, provided herein is a composition, e.g., a pharmaceutical composition, containing at least one agent described herein (e.g., an antigen binding molecule described herein, such as an antibody, a CAR or a TCR described herein, obtained from the non-human animal described herein) formulated together with a pharmaceutically acceptable carrier.

The pharmaceutical compositions provided herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; or (2) parenteral administration, for example, by subcutaneous, intramuscular, intravenous or epidural injection as, for example, a sterile solution or suspension, or sustained-release formulation.

Pharmaceutical compositions provided herein suitable for parenteral administration comprise one or more agents described herein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In certain embodiments, the compositions comprise an antibody, a TCR and/or a CAR described herein in a concentration resulting in a w/v appropriate for a desired dose. The antibody, TCR and/or CAR may be present in the composition at a concentration of at least 1 mg/mL, at least 5 mg/mL, at least 10 mg/mL, at least 15 mg/mL, at least 20 mg/mL, at least 25 mg/mL, at least 30 mg/mL, at least 35 mg/mL, at least 40 mg/mL, at least 45 mg/mL, at least 50 mg/mL, at least 55 mg/mL, at least 60 mg/mL, at least 65 mg/mL, at least 70 mg/mL, at least 75 mg/mL, at least 80 mg/mL, at least 85 mg/mL, at least 90 mg/mL, at least 95 mg/mL, at least 100 mg/mL, at least 105 mg/mL, at least 110 mg/mL, at least 115 mg/mL, at least 120 mg/mL, at least 125 mg/mL, at least 130 mg/mL, at least 135 mg/mL, at least 140 mg/mL, at least 150 mg/mL, at least 200 mg/mL, at least 250 mg/mL, or at least 300 mg/mL.

In some embodiments, the composition comprises one or more active compounds as necessary for the particular indication being treated, typically those with complementary activities that do not adversely affect each other. Such additional active compounds are suitably present in combination in amounts that are effective for the purpose intended.

In some embodiments, compositions are prepared by mixing an antibody, a TCR and/or a CAR described herein with optional physiologically acceptable carriers, excipients or stabilizers, including, but not limited to buffering agents, saccharides, salts, surfactants, solubilizers, polyols, diluents, binders, stabilizers, salts, lipophilic solvents, amino acids, chelators, preservatives, or the like (Goodman and Gilman's The Pharmacological Basis of Therapeutics, 12th edition, L. Brunton, et al. and Remington's Pharmaceutical Sciences, 16th edition, Osol, A. Ed. (1999)), in the form of lyophilized compositions or aqueous solutions at a desired final concentration. Acceptable carriers, excipients, or stabilizers are nontoxic to recipients at the dosages and concentrations employed, and include buffers such as histidine, phosphate, citrate, glycine, acetate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrolidone; amino acids such as glycine, glutamine, asparagine, histidine, arginine, or lysine; monosaccharides, disaccharides, and other carbohydrates including trehalose, glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, polysorbate 80, PLURONICS® or polyethylene glycol (PEG).

In some embodiments, the buffering agent is histidine, citrate, phosphate, glycine, or acetate. The saccharide excipient may be trehalose, sucrose, mannitol, maltose or raffinose. The surfactant may be polysorbate 20, polysorbate 40, polysorbate 80, or Pluronic F68. The salt may be NaCl, KCl, MgCl2, or CaCl2.

In some embodiments, the composition comprises a buffering or pH adjusting agent to provide improved pH control. Such a composition may have a pH of between about 3.0 and about 9.0, between about 4.0 and about 8.0, between about 5.0 and about 8.0, between about 5.0 and about 7.0, between about 5.0 and about 6.5, between about 5.5 and about 8.0, between about 5.5 and about 7.0, or between about 5.5 and about 6.5. In a further embodiment, such a composition has a pH of about 3.0, about 3.5, about 4.0, about 4.5, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.5, about 8.0, about 8.5, or about 9.0. In a specific embodiment, a composition has a pH of about 6.0. One of skill in the art understands that the pH of a composition generally should not be equal to the isoelectric point of the particular antibody, TCR or CAR to be used in the composition. Typically, the buffering agent is a salt prepared from an organic or inorganic acid or base. Representative buffering agents include, but are not limited to, organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. In addition, amino acid components can also function in a buffering capacity. Representative amino acid components which may be utilized in the composition as buffering agents include, but are not limited to, glycine and histidine. In certain embodiments, the buffering agent is chosen from histidine, citrate, phosphate, glycine, and acetate. In a specific embodiment, the buffering agent is histidine. In another specific embodiment, the buffering agent is citrate. In yet another specific embodiment, the buffering agent is glycine. The purity of the buffering agent should be at least 98%, or at least 99%, or at least 99.5%. As used herein, the term "purity" in the context of histidine and glycine refers to chemical purity of histidine or glycine as understood in the art, e.g., as described in The Merck Index, 13th ed., O'Neil et al. ed. (Merck & Co., 2001).

In certain embodiments, the composition comprises histidine as a buffering agent. In certain embodiments the histidine is present in the composition at a concentration of at least about 1 mM, at least about 5 mM, at least about 10 mM, at least about 20 mM, at least about 30 mM, at least about 40 mM, at least about 50 mM, at least about 75 mM, at least about 100 mM, at least about 150 mM, or at least about 200 mM histidine. In another embodiment, a composition comprises between about 1 mM and about 200 mM, between about 1 mM and about 150 mM, between about 1 mM and about 100 mM, between about 1 mM and about 75 mM, between about 10 mM and about 200 mM, between about 10 mM and about 150 mM, between about 10 mM and about 100 mM, between about 10 mM and about 75 mM, between about 10 mM and about 50 mM, between about 10 mM and about 40 mM, between about 10 mM and about 30 mM, between about 20 mM and about 75 mM, between about 20 mM and about 50 mM, between about 20 mM and about 40 mM, or between about 20 mM and about 30 mM histidine. In a further embodiment, the composition comprises about 1 mM, about 5 mM, about 10 mM, about 20 mM, about 25 mM, about 30 mM, about 35 mM, about 40 mM, about 45 mM, about 50 mM, about 60 mM, about 70 mM, about 80 mM, about 90 mM, about 100 mM, about 150 mM, or about 200 mM histidine. In a specific embodiment, a composition may comprise about 10 mM, about 25 mM, or no histidine.

In some embodiments, the composition comprises a carbohydrate excipient. Carbohydrate excipients can act, e.g., as viscosity enhancing agents, stabilizers, bulking agents, solubilizing agents, and/or the like. Carbohydrate excipients are generally present at between about 1% to about 99% by weight or volume, e.g., between about 0.1% to about 20%, between about 0.1% to about 15%, between about 0.1% to about 5%, between about 1% to about 20%, between about 5% to about 15%, between about 8% to about 10%, between about 10% and about 15%, between about 15% and about 20%, between 0.1% to 20%, between 5% to 15%, between 8% to 10%, between 10% and 15%, between 15% and 20%, between about 0.1% to about 5%, between about 5% to about 10%, or between about 15% to about 20%. In still other specific embodiments, the carbohydrate excipient is present at 1%, or at 1.5%, or at 2%, or at 2.5%, or at 3%, or at 4%, or at 5%, or at 10%, or at 15%, or at 20%.

In some embodiments, the composition comprises a carbohydrate excipient. Carbohydrate excipients suitable for use in the compositions include, but are not limited to, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and the like. In certain embodiments, the carbohydrate excipients for use in the compositions provided herein are chosen from sucrose, trehalose, lactose, mannitol, and raffinose. In a specific embodiment, the carbohydrate excipient is trehalose. In another specific embodiment, the carbohydrate excipient is mannitol. In yet another specific embodiment, the carbohydrate excipient is sucrose. In still another specific embodiment, the carbohydrate excipient is raffinose. The purity of the carbohydrate excipient should be at least 98%, or at least 99%, or at least 99.5%.

In some embodiments, the composition comprises trehalose. In certain embodiments, a composition comprises at least about 1%, at least about 2%, at least about 4%, at least about 8%, at least about 20%, at least about 30%, or at least about 40% trehalose. In another embodiment, a composition comprises between about 1% and about 40%, between about 1% and about 30%, between about 1% and about 20%, between about 2% and about 40%, between about 2% and about 30%, between about 2% and about 20%, between about 4% and about 40%, between about 4% and about 30%, or between about 4% and about 20% trehalose. In a further embodiment, a composition comprises about 1%, about 2%, about 4%, about 6%, about 8%, about 15%, about 20%, about 30%, or about 40% trehalose. In a specific embodiment, a composition comprises about 4%, about 6% or about 15% trehalose.

In certain embodiments, the composition comprises an excipient. In a specific embodiment, a composition comprises at least one excipient chosen from: sugar, salt, surfactant, amino acid, polyol, chelating agent, emulsifier and preservative. In certain embodiments, a composition comprises a salt, e.g., a salt selected from: NaCl, KCl, CaCl2, and MgCl2. In a specific embodiment, the composition comprises NaCl.

In some embodiments, the composition comprises an amino acid, e.g., lysine, arginine, glycine, histidine or an amino acid salt. The composition may comprise at least about 1 mM, at least about 10 mM, at least about 25 mM, at least about 50 mM, at least about 100 mM, at least about 150 mM, at least about 200 mM, at least about 250 mM, at least about 300 mM, at least about 350 mM, or at least about 400 mM of an amino acid. In another embodiment, the composition may comprise between about 1 mM and about 100 mM, between about 10 mM and about 150 mM, between about 25 mM and about 250 mM, between about 25 mM and about 300 mM, between about 25 mM and about 350 mM, between about 25 mM and about 400 mM, between about 50 mM and about 250 mM, between about 50 mM and about 300 mM, between about 50 mM and about 350 mM, between about 50 mM and about 400 mM, between about 100 mM and about 250 mM, between about 100 mM and about 300 mM, between about 100 mM and about 400 mM, between about 150 mM and about 250 mM, between about 150 mM and about 300 mM, or between about 150 mM and about 400 mM of an amino acid. In a further embodiment, a composition comprises about 1 mM, 1.6 mM, 25 mM, about 50 mM, about 100 mM, about 150 mM, about 200 mM, about 250 mM, about 300 mM, about 350 mM, or about 400 mM of an amino acid.

In some embodiments, the composition comprises a surfactant. The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials. Pharmaceutically acceptable surfactants like polysorbates (e.g., polysorbates 20 or 80); poly-oxamers (e.g., poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUA® series (Mona Industries, Inc., Paterson, N.J.), polyethyl glycol, polypropyl glycol, and copolymers of ethylene and propylene glycol (e.g., PLURONICS® PF68, etc.), can optionally be added to the compositions to reduce aggregation. In certain embodiments, a composition comprises Polysorbate 20, Polysorbate 40, Polysorbate 60, or Polysorbate 80. Surfactants are particularly useful if a pump or plastic container is used to administer the composition. The presence of a pharmaceutically acceptable surfactant mitigates the propensity for the protein to aggregate. The compositions may comprise a polysorbate which is at a concentration ranging from between about 0.001% to about 1%, or about 0.001% to about 0.1%, or about 0.01% to about 0.1%. In other specific embodiments, the compositions comprise a polysorbate which is at a concentration of 0.001%, or 0.002%, or 0.003%, or 0.004%, or 0.005%, or 0.006%, or 0.007%, or 0.008%, or 0.009%, or 0.01%, or 0.015%, or 0.02%.

In some embodiments, the composition comprises other excipients and/or additives including, but not limited to, diluents, binders, stabilizers, lipophilic solvents, preservatives, adjuvants, or the like. Pharmaceutically acceptable excipients and/or additives may be used in the compositions provided herein. Commonly used excipients/additives, such as pharmaceutically acceptable chelators (for example, but not limited to, EDTA, DTPA or EGTA) can optionally be added to the compositions to reduce aggregation. These additives are particularly useful if a pump or plastic container is used to administer the composition.

In some embodiments, the composition comprises a preservative. Preservatives, such as phenol, m-cresol, p-cresol, o-cresol, chlorocresol, benzyl alcohol, phenylmercuric nitrite, phenoxyethanol, formaldehyde, chlorobutanol, magnesium chloride (for example, but not limited to, hexahydrate), alkylparaben (methyl, ethyl, propyl, butyl and the like), benzalkonium chloride, benzethonium chloride, sodium dehydroacetate and thimerosal, or mixtures thereof can optionally be added to the compositions at any suitable concentration such as between about 0.001% to about 5%, or any range or value therein. The concentration of preservative used in the compositions is a concentration sufficient to yield a microbial effect. Such concentrations are dependent on the preservative selected and are readily determined by the skilled artisan.

In some embodiments, the composition is isotonic with human blood, wherein the compositions have essentially the same osmotic pressure as human blood. Such isotonic compositions will generally have an osmotic pressure from about 250 mOSm to about 350 mOSm. Isotonicity can be measured by, for example, using a vapor pressure or ice-freezing type osmometer. Tonicity of a composition is adjusted by the use of tonicity modifiers. "Tonicity modifiers" are those pharmaceutically acceptable inert substances that can be added to the composition to provide an isotonity of the composition. Tonicity modifiers suitable for the compositions provided herein include, but are not limited to, saccharides, salts and amino acids.

In certain embodiments, the composition is a pyrogen-free composition which is substantially free of endotoxins and/or related pyrogenic substances. Endotoxins include toxins that are confined inside a microorganism and are released only when the microorganisms are broken down or die. Pyrogenic substances also include fever-inducing, thermostable substances from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one-hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with proteins of interest (e.g., antibodies), even trace amounts of harmful and dangerous endotoxin must be removed. In some embodiments, the endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg.

When used for in vivo administration, the composition described herein should be sterile. The composition may be sterilized by various sterilization methods, including sterile filtration, radiation, etc. In certain embodiments, composition is filter-sterilized with a presterilized 0.22-micron filter. Sterile compositions for injection can be formulated according to conventional pharmaceutical practice as described in "Remington: The Science & Practice of Pharmacy", 21st ed., Lippincott Williams & Wilkins, (2005). Compositions comprising proteins of interest (e.g., antibodies or TCRs or CARs) such as those disclosed herein, ordinarily will be stored in lyophilized form or in solution. It is contemplated that sterile compositions comprising proteins of interest (e.g., antibody, TCR or CAR) are placed into a container having a sterile access port, for example, an intravenous solution bag or vial having an adapter that allows retrieval of the composition, such as a stopper pierceable by a hypodermic injection needle. In certain embodiments, a composition is provided as a pre-filled syringe.

In certain embodiments, the composition is a lyophilized formulation. The term "lyophilized" or "freeze-dried" includes a state of a substance that has been subjected to a drying procedure such as lyophilization, where at least 50% of moisture has been removed.

Regardless of the route of administration selected, agents provided herein, which may be used in a suitable hydrated form, and/or the pharmaceutical compositions of the provided herein, are formulated into pharmaceutically-acceptable dosage forms by conventional methods known to those of skill in the art.

Therapeutic Methods

In certain aspects, provided herein are methods of treating a disease or disorder comprising administering to a subject an antigen binding protein (e.g., an antibody, a TCR and/or a CAR described herein, such as a fully human antibody, TCR or CAR). In some embodiments, the antibody, a TCR and/or a CAR is an antibody, a TCR and/or a CAR obtained from or obtainable using the methods described herein (e.g., using a non-human animal described herein).

In certain embodiments, provided herein are methods of treating cancer in a subject comprising administering to the subject a pharmaceutical composition described herein (e.g., a pharmaceutic composition comprising an antibody described herein, such as a fully human antibody, TCR or CAR described herein, obtained from the non-human animal as described herein). In some embodiments, the methods described herein can be used to treat any cancerous or pre-cancerous tumor. Cancers that may be treated by methods and compositions described herein include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. Nonlimiting examples of various histological types of cancer include: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In certain embodiments, the antibody, TCR or CAR in the pharmaceutical composition administered to the subject has binding specificity for an epitope of a cancer-associated antigen (e.g., an epitope expressed by the cancer being treated). Examples of cancer-associated antigens include, but are not limited to, adipophilin, AIM-2, ALDH1A1, alpha-actinin-4, alpha-fetoprotein ("AFP"), ARTC1, B-RAF, BAGE-1, BCLX (L), BCR-ABL fusion protein b3a2, beta-catenin, BING-4, CA-125, CALCA, carcinoembryonic antigen ("CEA"), CASP-5, CASP-8, CD274, CD45, Cdc27, CDK12, CDK4, CDKN2A, CEA, CLPP, COA-1, CPSF, CSNK1A1, CTAG1, CTAG2, cyclin D1, Cyclin-A1, dek-can fusion protein, DKK1, EFTUD2, Elongation factor 2, ENAH (hMena), Ep-CAM, EpCAM, EphA3, epithelial tumor antigen ("ETA"), ETV6-AML1 fusion protein, EZH2, FGF5, FLT3-ITD, FN1, G250/MN/CAIX, GAGE-1,2,8, GAGE-3,4,5,6,7, GAS7, glypican-3, GnTV, gp100/Pme117, GPNMB, HAUS3, Hepsin, HER-2/neu, HERV-K-MEL, HLA-A11, HLA-A2, HLA-DOB, hsp70-2, IDO1, IGF2B3, IL13Ralpha2, Intestinal carboxyl esterase, K-ras, Kallikrein 4, KIF20A, KK-LC-1, KKLC1, KM-HN-1, KMHN1 also known as CCDC110, LAGE-1, LDLR-fucosyltransferaseAS fusion protein, Lengsin, M-CSF, MAGE-A1, MAGE-A10, MAGE-A12, MAGE-A2, MAGE-A3, MAGE-A4, MAGE-A6, MAGE-A9, MAGE-C1, MAGE-C2, malic enzyme, mammaglobin-A, MART2, MATN, MC1R, MCSP, mdm-2, MEL Melan-A/MART-1, Meloe, Midkine, MMP-2, MMP-7, MUC1, MUCSAC, mucin, MUM-1, MUM-2, MUM-3, Myosin, Myosin class I, N-raw, NA88-A, neo-PAP, NFYC, NY-BR-1, NY-ESO-1/LAGE-2, OA1, OGT, OS-9, P polypeptide, p53, PAP, PAXS, PBF, pml-RARalpha fusion protein, polymorphic epithelial mucin ("PEM"), PPP1R3B, PRAME, PRDX5, PSA, PSMA, PTPRK, RAB38/NY-MEL-1, RAGE-1, RBAF600, RGSS, RhoC, RNF43, RU2AS, SAGE, secemin 1, SIRT2, SNRPD1, SOX10, Sp17, SPA17, SSX-2, SSX-4, STEAP1, survivin, SYT-SSX1 or -SSX2 fusion protein, TAG-1, TAG-2, Telomerase, TGF-betaRII, TPBG, TRAG-3, Triosephosphate isomerase, TRP-1/gp75, TRP-2, TRP2-INT2, tyrosinase, tyrosinase ("TYR"), VEGF, WT1, XAGE-1b/GAGED2a. In some embodiments, the antigen is a neo-antigen.

In certain embodiments, provided herein are methods of treating a subject suffering from an infection, including a viral infection, a fungal infection, a bacterial infection, a helminth infection, or a protozoan infection, comprising administering to the subject a pharmaceutical composition described herein (e.g., a pharmaceutic composition comprising an antibody, TCR or CAR described herein obtained from the non-human animals described herein). Nonlimiting examples of viral infectious diseases include HPV, HBV, hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, and influenza virus. A nonlimiting example of parasitic infection is malaria. Nonlimiting examples of bacterial, fungal and other pathogenic diseases include *Aspergillus, Brugia, Candida, Chlamydia, Coccidia, Cryptococcus, Dirofilaria, Gonococcus, Histoplasma, Leishmania, Mycobacterium, Mycoplasma,* Paramecium, Pertussis, *Plasmodium, Pneumococcus, Pneumocystis, Rickettsia, Salmonella, Shigella, Staphylococcus, Streptococcus, Toxoplasma* and Vibriocholerae. Exemplary species include *Neisseria gonorrhea, Mycobacterium tuberculosis, Candida albicans, Candida tropicalis, Trichomonas vaginalis, Haemophilus vaginalis,* Group B *Streptococcus* sp., *Microplasma hominis, Hemophilus ducreyi, Granuloma inguinale, Lymphopathia venereum, Treponema pallidum, Brucella abortus. Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani, Clostridium botulinum*; or, a fungus, such as, e.g., *Paracoccidioides brasiliensis*; or other pathogen, e.g., *Plasmodium falciparum*.

In certain embodiments, the antibody, TCR or CAR in the pharmaceutical composition administered to the subject has binding specificity for an epitope of an antigen expressed by an infectious pathogen (e.g., an epitope expressed by the infectious pathogen being treated).

In some embodiments, provided herein is a method of treating an inflammatory disease, skin or organ transplantation rejection, graft-versus-host disease (GVHD), or autoimmune diseases, comprising administering to a subject a pharmaceutical composition described herein (e.g., a pharmaceutic composition comprising an antibody, TCR or CAR described herein obtained from the non-human animals described herein). Examples of autoimmune diseases include, for example, glomerular nephritis, arthritis, dilated cardiomyopathy-like disease, ulceous colitis, Sjogren syndrome, Crohn disease, systemic erythematodes, chronic rheumatoid arthritis, multiple sclerosis, psoriasis, allergic contact dermatitis, polymyosiis, pachyderma, periarteritis nodosa, rheumatic fever, vitiligo vulgaris, insulin dependent diabetes mellitus, Behcet disease, Hashimoto disease, Addison disease, dermatomyositis, myasthenia gravis, Reiter syndrome, Graves' disease, anaemia perniciosa, Goodpasture syndrome, sterility disease, chronic active hepatitis, pemphigus, autoimmune thrombopenic purpura, and autoimmune hemolytic anemia, active chronic hepatitis, Addison's disease, anti-phospholipid syndrome, atopic allergy, autoimmune atrophic gastritis, achlorhydra autoimmune, celiac disease, Cushing's syndrome, dermatomyositis, discoid lupus, erythematosis, Goodpasture's syndrome, Hashimoto's thyroiditis, idiopathic adrenal atrophy, idiopathic thrombocytopenia, insulin-dependent diabetes, Lambert-Eaton syndrome, lupoid hepatitis, some cases of lymphopenia, mixed connective tissue disease, pemphigoid, pemphigus vulgaris, pernicious anema, phacogenic uveitis, polyarteritis nodosa, polyglandular autosyndromes, primary biliary cirrhosis, primary sclerosing cholangitis, Raynaud's syndrome, relapsing polychondritis, Schmidt's syndrome, limited scleroderma (or crest syndrome), sympathetic ophthalmia, systemic lupus erythematosis, Takayasu's arteritis, temporal arteritis, thyrotoxicosis, type b insulin resistance, ulcerative colitis and Wegener's granulomatosis.

In certain embodiments, the antibody, TCR or CAR in the pharmaceutical composition administered to the subject has binding specificity for the target of an autoreactive T cell in the disease being treated (e.g., an epitope targeted by autoreactive T cells in an autoimmune disease). Exemplary proteins include targeted by autoreactive T cells include, for example, p205, insulin, thyroid-stimulating hormone, tyrosinase, TRP1, and myelin.

The pharmaceutical compositions described herein may be delivered by any suitable route of administration, including orally, nasally, as by, for example, a spray, rectally, intravaginally, parenterally, intracisternally and topically, as by powders, ointments or drops, including buccally and sublingually. In certain embodiments the pharmaceutical compositions are delivered generally (e.g., via oral or parenteral administration).

Actual dosage levels of the active ingredients in the pharmaceutical compositions described herein may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

In some embodiments, the CAR and/or TCR described here are used for T cell based therapy. For example, in certain embodiments, T cells expressing a CAR and/or TCR described herein are administered to a subject to induce a T cell based immune response in the subject. Methods useful in T cell based therapy is described in, for example, in Schumacher *Nat. Rev. Immunol.* 2:512-519 (2002) and Bitton et al., *Frontiers in Bioscience* 4:d386-393 (1999), each of which is incorporated by reference herein.

In some aspects, provided herein is a method of inducing an immune response (e.g., a T cell based immune response) in a subject. In some embodiments, the method includes administering to the subject a cell (e.g., a human T cell, such as a CD4 T cell or a CD8 T cell) expressing a CAR or TCR described herein.

In some embodiments, the subject is a subject in need thereof. In some embodiments, the subject is a subject with cancer or a subject infected with a pathogen. In such embodiments, the peptide in the peptide/MHC complex recognized by the CAR or TCR is a peptide of a cancer antigen or a peptide from an antigen expressed by an infectious pathogen.

In some aspects, provided herein is a method of inhibiting an immune response in a subject. In some embodiments, the method includes administering to the subject a regulatory T cell (e.g., a CD4$^+$, CD-25$^+$ and Foxp3$^+$ regulatory T cell or a Treg17 T cell) expressing a CAR or TCR described.

In some embodiments, the subject is a subject in need thereof, e.g., a subject with an autoimmune disease. In such embodiments, the T cell is a regulatory T cell (i.e., a suppressor T cell) and the peptide in the peptide/MHC complex recognized by the TCR or CAR is a self-antigen to which the subject is undergoing an autoimmune response.

Nucleic Acid Molecules

Provided herein are nucleic acid molecules that encode the antibodies, TCRs or CARs described herein and/or portions of antibodies, TCRs and CARs described herein. In some embodiments, the nucleic acid encodes a variable domain of an antibody, TCR or CAR described herein. The nucleic acid molecules may be present, for example, in whole cells, in a cell lysate, or in a partially purified or substantially pure form.

In certain aspects, provided herein are nucleic acids encoding an antibody, TCR and/or CAR polypeptide described herein or a portion thereof. The nucleic acids may be present, for example, in whole cells, in a cell lysate, or in a partially purified or substantially pure form. Nucleic acids described herein can be obtained using standard molecular biology techniques. For example, nucleic acid molecules described herein can be cloned using standard PCR techniques or chemically synthesized. For nucleic acids encoding CARs, TCRs or antibodies expressed by hybridomas, cDNAs encoding each chain of the antibody, TCR or CAR made by the hybridoma can be obtained by standard PCR amplification or cDNA cloning techniques.

In certain embodiments, provided herein are vectors that contain the nucleic acid molecules described herein. As used herein, the term "vector," refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby be replicated along with the host genome. Moreover, certain vectors are capable of directing the expression of genes. Such vectors are referred to herein as "recombinant expression vectors" (or simply, "expression vectors").

In certain embodiments, provided herein are cells that contain a nucleic acid described herein (e.g., a nucleic acid encoding an antibody, TCR or CAR described herein or a portion thereof). The cell can be, for example, prokaryotic, eukaryotic, mammalian, avian, murine and/or human. In certain embodiments the nucleic acid described herein is operably linked to a transcription control element such as a promoter. In some embodiments the cell transcribes the nucleic acid described herein and thereby expresses an antibody, antigen binding fragment thereof or polypeptide described herein. The nucleic acid molecule can be integrated into the genome of the cell or it can be extrachromasomal.

Nucleic acid molecules provided herein can be obtained using standard molecular biology techniques. For example, nucleic acid molecules described herein can be cloned using standard PCR techniques or chemically synthesized.

For antibodies and CAR nucleic acids described herein, once DNA fragments encoding a $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operably linked to another DNA fragment encoding another protein, such as an antibody constant region or a flexible linker. The term "operably linked", as used in this context, is intended to mean that the two DNA fragments are joined such that the amino acid sequences encoded by the two DNA fragments remain in-frame.

The isolated DNA encoding the heavy chain variable region can be converted to a full-length heavy chain gene by operably linking the heavy chain variable region DNA to another DNA molecule encoding heavy chain constant regions (e.g., CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242, or Lefranc, The Immunoglobulin Handbook, London: Academic Press 2001) and DNA fragments encompassing these regions can be obtained by standard PCR amplification. The heavy chain constant region can be an IgG1, IgG2, IgG3, IgG4, IgA, IgE, IgM or IgD constant region. For a Fab fragment heavy chain gene, the $V_H$-encoding DNA can be operably linked to another DNA molecule encoding only the heavy chain CH1 constant region.

The isolated DNA encoding the light chain variable region can be converted to a full-length light chain gene (as well as a Fab light chain gene) by operably linking the light chain variable region encoding DNA to another DNA molecule encoding a light chain constant region. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242, or Lefranc, The Immunoglobulin Handbook, London: Academic Press 2001) and DNA fragments encompassing these regions can be obtained by standard PCR amplification. The light chain constant region can be a kappa or lambda constant region.

Additional Exemplary Embodiments

In exemplary embodiment 1, provided herein is a genetically modified non-human animal comprising in its genome a nucleic acid sequence encoding human Terminal Deoxynucleotidyltransferase (hTdT).

In exemplary embodiment 2, provided herein is the genetically modified non-human animal of embodiment 1, wherein the nucleic acid sequence encoding hTdT is operably linked to a transcriptional control element.

In exemplary embodiment 3, provided herein is the genetically modified non-human animal of embodiment 2, wherein the transcriptional control element drives expression of the nucleic acid sequence encoding hTdT in pro-B cells and/or pre-B cells.

In exemplary embodiment 4, provided herein is the genetically modified non-human animal of embodiment 2, wherein the transcriptional control element is selected from the group consisting of a RAG1 transcriptional control element, a RAG2 transcriptional control element, an immunoglobulin heavy chain transcriptional control element, an immunoglobulin κ light chain transcriptional control element and/or an immunoglobulin λ light chain transcriptional control element.

In exemplary embodiment 5, provided herein is the genetically modified non-human animal of any one of embodiments 1 to 4, wherein the non-human animal expresses hTdT in pro-B cells and/or pre-B cells.

In exemplary embodiment 6, provided herein is the genetically modified non-human animal of embodiment 2, wherein the transcriptional control element drives expression of the nucleic acid sequence encoding hTdT in CD4/CD8 double-negative (DN) thymocytes and/or CD4/CD8 double-positive (DP) thymocytes.

In exemplary embodiment 7, provided herein is the genetically modified non-human animal of embodiment 2, wherein the transcriptional control element is a RAG1 transcriptional control element, a RAG2 transcriptional control element, a TCRα transcriptional control element, a TCRβ transcriptional control element, a TCRγ transcriptional control element and/or a TCRδ transcriptional control element.

In exemplary embodiment 8, provided herein is the genetically modified non-human animal of any one of embodiments 1 to 7, wherein the non-human animal expresses hTdT in DN thymocytes and/or DP thymocytes.

In exemplary embodiment 9, provided herein is the genetically modified non-human animal of any one of embodiments 1 to 8, wherein the nucleic acid sequence encoding hTdT is located at an immunoglobulin κ light chain locus, an immunoglobulin λ light chain locus, an immunoglobulin heavy chain locus, a RAG1 locus, a RAG2 locus, a TCRα chain locus, a TCRβ chain locus, a TCRγ chain locus and/or a TCRδ chain locus.

In exemplary embodiment 10, provided herein is the genetically modified non-human animal of any one of embodiments 1 to 9, wherein the nucleic acid sequence encoding hTdT is not operably linked to a constitutive transcriptional control element.

In exemplary embodiment 11, provided herein is the genetically modified non-human animal of any one of embodiments 1 to 10, wherein the hTdT is not constitutively expressed.

In exemplary embodiment 12, provided herein is the genetically modified non-human animal of any one of embodiments 1 to 11, wherein at least 10% of the V-J immunoglobulin light chain junctions in the animal comprise non-template additions.

In exemplary embodiment 13, provided herein is the genetically modified non-human animal of embodiment 12, wherein at least 20% of the V-J immunoglobulin light chain junctions in the animal comprise non-template additions.

In exemplary embodiment 14, provided herein is the genetically modified non-human animal of embodiment 12, wherein at least 40% of the V-J immunoglobulin light chain junctions in the animal comprise non-template additions.

In exemplary embodiment 15, provided herein is a genetically modified non-human animal comprising in its genome: a nucleic acid sequence encoding an exogenous Terminal Deoxynucleotidyltransferase (TdT); and an immunoglobulin variable region comprising unrearranged human immunoglobulin variable region gene segments operably linked to an immunoglobulin constant region gene.

In exemplary embodiment 16, provided herein is the genetically modified non-human animal of embodiment 15, wherein the exogenous TdT is human TdT.

In exemplary embodiment 17, provided herein is the genetically modified non-human animal of embodiment 15 or 16, wherein the nucleic acid sequence encoding the exogenous TdT is operably linked to a transcriptional control element.

In exemplary embodiment 18, provided herein is the genetically modified non-human animal of embodiment 17, wherein the transcriptional control element drives expression of the nucleic acid sequence encoding the exogenous TdT in pro-B cells and/or pre-B cells.

In exemplary embodiment 19, provided herein is the genetically modified non-human animal of embodiment 17, wherein the transcriptional control element is selected from the group consisting of a RAG1 transcriptional control element, a RAG2 transcriptional control element, an immunoglobulin heavy chain transcriptional control element, an immunoglobulin κ light chain transcriptional control element and/or an immunoglobulin λ light chain transcriptional control element.

In exemplary embodiment 20, provided herein is the genetically modified non-human animal of any one of embodiments 15 to 19, wherein the non-human animal expresses the exogenous TdT in pro-B cells and/or pre-B cells.

In exemplary embodiment 21, provided herein is the genetically modified non-human animal of embodiment 17, wherein the transcriptional control element drives expression of the nucleic acid sequence encoding the exogenous TdT in CD4/CD8 double-negative (DN) thymocytes and/or CD4/CD8 double-positive (DP) thymocytes.

In exemplary embodiment 22, provided herein is the genetically modified non-human animal of embodiment 17, wherein the transcriptional control element is a RAG1 transcriptional control element or a RAG2 transcriptional control element.

In exemplary embodiment 23, provided herein is the genetically modified non-human animal of any one of embodiments 15 to 22, wherein the non-human animal expresses the exogenous TdT in DN thymocytes and/or DP thymocytes.

In exemplary embodiment 24, provided herein is the genetically modified non-human animal of any one of embodiments 15 to 23, wherein the nucleic acid sequence encoding the exogenous TdT is located at an immunoglobulin κ light chain locus, an immunoglobulin λ light chain locus, an immunoglobulin heavy chain locus, a RAG1 locus, a RAG2 locus, a TCRα chain locus, a TCRβ chain locus, a TCRγ chain locus and/or a TCRδ chain locus.

In exemplary embodiment 25, provided herein is the genetically modified non-human animal of any one of embodiments 15 to 24, wherein the nucleic acid sequence encoding the exogenous TdT is not operably linked to a constitutive transcriptional control element.

In exemplary embodiment 26, provided herein is the genetically modified non-human animal of any one of embodiments 15 to 25, wherein the exogenous TdT is not constitutively expressed.

In exemplary embodiment 27, provided herein is the genetically modified non-human animal of any one of embodiments 15 to 26, wherein at least 10% of the V-J immunoglobulin light chain junctions in the animal comprise non-template additions.

In exemplary embodiment 28, provided herein is the genetically modified non-human animal of embodiment 27, wherein at least 20% of the V-J immunoglobulin light chain junctions in the animal comprise non-template additions.

In exemplary embodiment 29, provided herein is the genetically modified non-human animal of embodiment 27, wherein at least 40% of the V-J immunoglobulin light chain junctions in the animal comprise non-template additions.

In exemplary embodiment 30, provided herein is the genetically modified non-human animal of any one of embodiments 15 to 26, wherein the human immunoglobulin variable region gene segments are human heavy chain variable region gene segments.

In exemplary embodiment 31, provided herein is the genetically modified non-human animal of embodiment 30, wherein the constant region gene is a heavy chain constant region gene.

In exemplary embodiment 32, provided herein is the genetically modified non-human animal of embodiment 31, wherein the heavy chain constant region gene is a Cμ gene, a Cδ gene, a Cγ gene, a Cε gene or a Cα gene.

In exemplary embodiment 33, provided herein is the genetically modified non-human animal of embodiment 31 or 32, wherein the heavy chain constant region gene is of endogenous species origin.

In exemplary embodiment 34, provided herein is the genetically modified non-human animal of embodiment 31 or 32, wherein the heavy chain constant region gene is a mouse constant region gene.

In exemplary embodiment 35, provided herein is the genetically modified non-human animal of embodiment 31 or 32, wherein the heavy chain constant region gene is a rat constant region gene.

In exemplary embodiment 36, provided herein is the genetically modified non-human animal of embodiment 31 or 32, wherein the heavy chain constant region gene is a human constant region gene.

In exemplary embodiment 37, provided herein is the genetically modified non-human animal of embodiment 31 or 32, wherein the heavy chain constant region gene has a human CH1 domain and non-human CH2 and CH3 domains.

In exemplary embodiment 38, provided herein is the genetically modified non-human animal of embodiment 37, wherein the non-human CH2 and CH3 domains are of endogenous species origin.

In exemplary embodiment 39, provided herein is the genetically modified non-human animal of embodiment 37, wherein the non-human CH2 and CH3 domains are mouse CH2 and CH3 domains.

In exemplary embodiment 40, provided herein is the genetically modified non-human animal of embodiment 37, wherein the non-human CH2 and CH3 domains are rat CH2 and CH3 domains.

In exemplary embodiment 10, provided herein is the genetically modified non-human animal of embodiments 15-40, wherein the animal lacks a functional CH1 domain in an immunoglobulin heavy chain constant region selected from IgG, IgA, IgE, IgD, or a combination thereof.

In exemplary embodiment 20, provided herein is the genetically modified non-human animal of any one of embodiments 31 to 41, wherein the immunoglobulin variable region and the immunoglobulin constant region gene are located at an endogenous immunoglobulin heavy chain locus.

In exemplary embodiment 43, provided herein is the genetically modified non-human animal of any one of embodiments 30 to 42, further comprising in its genome an immunoglobulin variable region comprising unrearranged human light chain variable region gene segments operably linked to a second immunoglobulin constant region gene.

In exemplary embodiment 44, provided herein is the genetically modified non-human animal of embodiment 43, wherein the human immunoglobulin variable region gene segments operably linked to the second immunoglobulin constant region gene are human κ chain variable region gene segments.

In exemplary embodiment 45, provided herein is the genetically modified non-human animal of embodiment 43, wherein the human immunoglobulin variable region gene segments operably linked to the second immunoglobulin constant region gene are human λ chain variable region gene segments.

In exemplary embodiment 46, provided herein is the genetically modified non-human animal of any one of embodiments 43 to 45, wherein the second constant region gene is a light chain constant region gene.

In exemplary embodiment 47, provided herein is the genetically modified non-human animal of embodiment 46, wherein the second constant region gene is a κ constant region gene.

In exemplary embodiment 48, provided herein is the genetically modified non-human animal of embodiment 46, wherein the second constant region gene is a λ constant region gene.

In exemplary embodiment 49, provided herein is the genetically modified non-human animal of any one of embodiments 43 to 48, wherein the second constant region gene is of endogenous species origin.

In exemplary embodiment 50, provided herein is the genetically modified non-human animal of any one of embodiments 43 to 48, wherein the second constant region gene is a mouse constant region gene.

In exemplary embodiment 51, provided herein is the genetically modified non-human animal of any one of embodiments 43 to 48, wherein the second constant region gene is a rat constant region gene.

In exemplary embodiment 52, provided herein is the genetically modified non-human animal of any one of embodiments 43 to 48, wherein the second constant region gene is a human constant region gene.

In exemplary embodiment 53, provided herein is the genetically modified non-human animal of any one of embodiments 43 to 52, wherein the immunoglobulin variable region operably linked to the second immunoglobulin constant region gene is located at an endogenous immunoglobulin light chain locus.

In exemplary embodiment 54, provided herein is the genetically modified non-human animal of embodiment 53, wherein the second constant region gene is a κ constant region gene and the endogenous immunoglobulin light chain locus is an immunoglobulin κ locus.

In exemplary embodiment 55, provided herein is the genetically modified non-human animal of embodiment 53, wherein the second constant region gene is a λ constant region gene and the endogenous immunoglobulin light chain locus is an immunoglobulin λ locus.

In exemplary embodiment 56, provided herein is the genetically modified non-human animal of any one of embodiments 30 to 42, further comprising in its genome an immunoglobulin variable region comprising rearranged human light chain variable region (V/J) gene segments operably linked to a second immunoglobulin constant region gene.

In exemplary embodiment 57, provided herein is the genetically modified non-human animal of embodiment 56, wherein the rearranged human light chain variable region (V/J) gene segments operably linked to a second immunoglobulin constant region gene comprise a Vκ gene segments selected from Vκ1-39 and Vκ3-20, rearranged to a Jκ gene segment.

In exemplary embodiment 58, provided herein is the genetically modified non-human animal of embodiment 57, wherein the animal comprises in its genome an immunoglobulin light chain variable region comprising a Vκ1-39/Jκ5 or a Vκ3-20/Jκ1 sequence.

In exemplary embodiment 59, provided herein is the genetically modified non-human animal of any one of embodiments 30 to 42, further comprising in its genome an immunoglobulin variable region comprising a limited repertoire of human light chain variable region (V and J) gene segments operably linked to a second immunoglobulin constant region gene.

In exemplary embodiment 60, provided herein is the genetically modified non-human animal of embodiment 59, wherein the limited repertoire of human light chain variable region (V and J) gene segments operably linked to a second immunoglobulin constant region gene comprises two V gene segments and at least two, preferably five, J gene segments.

In exemplary embodiment 61, provided herein is the genetically modified non-human animal of embodiment 60, wherein the two V gene segments are Vk1-39 and Vk3-20 gene segments.

In exemplary embodiment 62, provided herein is the genetically modified non-human animal of any one of embodiments 15 to 29, wherein the human immunoglobulin variable region gene segments are human light chain variable region gene segments.

In exemplary embodiment 63, provided herein is the genetically modified non-human animal of embodiment 62, wherein the human immunoglobulin variable region gene segments are human κ chain variable region gene segments.

In exemplary embodiment 64, provided herein is the genetically modified non-human animal of embodiment 63, wherein the human immunoglobulin variable region gene segments are human λ chain variable region gene segments.

In exemplary embodiment 65, provided herein is the genetically modified non-human animal of any one of embodiments 62 to 64, wherein the constant region gene is a light chain constant region gene.

In exemplary embodiment 66, provided herein is the genetically modified non-human animal of embodiment 65, wherein the constant region gene is a κ constant region gene.

In exemplary embodiment 67, provided herein is the genetically modified non-human animal of embodiment 65, wherein the constant region gene is λ constant region gene.

In exemplary embodiment 68, provided herein is the genetically modified non-human animal of any one of embodiments 62 to 64, wherein the constant region gene is a heavy chain constant region gene.

In exemplary embodiment 69, provided herein is the genetically modified non-human animal of any one of embodiments 62 to 68, wherein the constant region gene is of endogenous species origin.

In exemplary embodiment 70, provided herein is the genetically modified non-human animal of any one of embodiments 62 to 68, wherein the constant region gene is a mouse constant region gene.

In exemplary embodiment 71, provided herein is the genetically modified non-human animal of any one of embodiments 62 to 68, wherein the constant region gene is a rat constant region gene.

In exemplary embodiment 72, provided herein is the genetically modified non-human animal of any one of embodiments 62 to 68, wherein the constant region gene is a human constant region gene.

In exemplary embodiment 73, provided herein is the genetically modified non-human animal of any one of embodiments 62 to 72, wherein the immunoglobulin variable region and the immunoglobulin constant region gene are located at an endogenous immunoglobulin light chain locus.

In exemplary embodiment 74, provided herein is the genetically modified non-human animal of embodiment 73, wherein the constant region gene is a κ constant region gene and the endogenous immunoglobulin light chain locus is an immunoglobulin κ locus.

In exemplary embodiment 75, provided herein is the genetically modified non-human animal of embodiment 73, wherein the constant region gene is λ constant region gene and the endogenous immunoglobulin light chain locus is an immunoglobulin λ locus.

In exemplary embodiment 76, provided herein is the genetically modified non-human animal of any one of embodiments 15 to 75, wherein the immunoglobulin variable region comprises immunoglobulin variable region intergenic sequences of human origin.

In exemplary embodiment 77, provided herein is the genetically modified non-human animal of any one of embodiments 15 to 75, wherein the immunoglobulin variable region comprises immunoglobulin variable region intergenic sequences of endogenous species origin.

In exemplary embodiment 78, provided herein is the genetically modified non-human animal of any one of embodiments 15 to 75, wherein the immunoglobulin variable region comprises immunoglobulin variable region intergenic sequences of mouse origin.

In exemplary embodiment 79, provided herein is the genetically modified non-human animal of any one of embodiments 15 to 75, wherein the immunoglobulin variable region comprises immunoglobulin variable region intergenic sequences of rat origin.

In exemplary embodiment 80, provided herein is the genetically modified non-human animal of any one of embodiments 15 to 79, further comprising in its genome an inactivated endogenous immunoglobulin locus.

In exemplary embodiment 81, provided herein is the genetically modified non-human animal of embodiment 80, wherein the inactivated endogenous immunoglobulin locus is an endogenous immunoglobulin heavy chain locus.

In exemplary embodiment 82, provided herein is the genetically modified non-human animal of embodiment 81, wherein the endogenous immunoglobulin heavy chain locus is inactivated by deletion of at least part of the variable region of the endogenous heavy chain locus.

In exemplary embodiment 83, provided herein is the genetically modified non-human animal of embodiment 82, wherein the deletion of the at least part of the variable region comprises deletion of the J gene segments of the variable region.

In exemplary embodiment 84, provided herein is the genetically modified non-human animal of embodiment 81, wherein the endogenous immunoglobulin heavy chain locus is inactivated by deletion of at least part of the constant region of the endogenous heavy chain locus.

In exemplary embodiment 85, provided herein is the genetically modified non-human animal of embodiment 84, wherein the deletion of the at least part of the constant region comprises deletion of the Cµ gene of the constant region.

In exemplary embodiment 86, provided herein is the genetically modified non-human animal of embodiment 80, wherein the inactivated endogenous immunoglobulin locus is an endogenous immunoglobulin κ chain locus.

In exemplary embodiment 87, provided herein is the genetically modified non-human animal of embodiment 86, wherein the endogenous immunoglobulin κ chain locus is inactivated by deletion of at least part of the variable region of the endogenous κ chain locus.

In exemplary embodiment 88, provided herein is the genetically modified non-human animal of embodiment 87, wherein the deletion of the at least part of the variable region comprises deletion of the J gene segments of the variable region.

In exemplary embodiment 89, provided herein is the genetically modified non-human animal of embodiment 86, wherein the endogenous immunoglobulin κ locus is inactivated by deletion of at least part of the constant region of the endogenous κ chain locus.

In exemplary embodiment 90, provided herein is the genetically modified non-human animal of embodiment 89, wherein the deletion of the at least part of the constant region comprises deletion of the Cκ gene of the constant region.

In exemplary embodiment 91, provided herein is the genetically modified non-human animal of embodiment 80, wherein the inactivated endogenous immunoglobulin locus is an endogenous immunoglobulin λ chain locus.

In exemplary embodiment 92, provided herein is the genetically modified non-human animal of embodiment 91, wherein the endogenous immunoglobulin λ chain locus is inactivated by deletion of at least part of a V-J-C cluster of the endogenous λ chain locus.

In exemplary embodiment 93, provided herein is the genetically modified non-human animal of any one of embodiments 15 to 92, wherein the unrearranged human immunoglobulin variable region gene segments undergo rearrangement during B cell development to generate rearranged variable region genes in the B cells of the non-human animal.

In exemplary embodiment 94, provided herein is the genetically modified non-human animal of embodiment 93, wherein at least 10% of the rearranged variable region genes comprise non-template additions.

In exemplary embodiment 95, provided herein is the genetically modified non-human animal of embodiment 93, wherein at least 20% of the rearranged variable region genes comprise non-template additions.

In exemplary embodiment 96, provided herein is the genetically modified non-human animal of embodiment 93, wherein at least 40% of the rearranged variable region genes comprise non-template additions.

In exemplary embodiment 97, provided herein is the genetically modified non-human animal of any one of embodiments 93 to 96, wherein the animal expresses antibodies comprising a variable domain encoded by the rearranged variable region gene and a constant domain encoded by the constant region gene.

In exemplary embodiment 98, provided herein is the genetically modified non-human animal of any one of embodiments 15 to 97 further comprising a functional ectopic mouse Adam6 gene.

In exemplary embodiment 99, provided herein is a genetically modified non-human animal comprising in its genome: a nucleic acid sequence encoding an exogenous Terminal Deoxynucleotidyltransferase (TdT); and a T cell receptor (TCR) variable region comprising unrearranged human TCR variable region gene segments operably linked to a TCR constant region gene.

In exemplary embodiment 100, provided herein is the genetically modified non-human animal of embodiment 99, wherein the exogenous TdT is human TdT.

In exemplary embodiment 101, provided herein is the genetically modified non-human animal of embodiment 99 or 100, wherein the nucleic acid sequence encoding the exogenous TdT is operably linked to a transcriptional control element.

In exemplary embodiment 102, provided herein is the genetically modified non-human animal of embodiment 101, wherein the transcriptional control element drives expression of the nucleic acid sequence encoding the exogenous TdT in CD4/CD8 double-negative (DN) thymocytes and/or CD4/CD8 double-positive (DP) thymocytes.

In exemplary embodiment 103, provided herein is the genetically modified non-human animal of embodiment 101, wherein the transcriptional control element is a RAG1 transcriptional control element, a RAG2 transcriptional control element, a TCRα transcriptional control element, a TCRβ transcriptional control element, a TCRγ transcriptional control element and/or a TCRδ transcriptional control element.

In exemplary embodiment 104, provided herein is the genetically modified non-human animal of any one of embodiments 99 to 103, wherein the non-human animal expresses the exogenous TdT in DN thymocytes and/or DP thymocytes.

In exemplary embodiment 105, provided herein is the genetically modified non-human animal of any one of embodiments 99 to 104, wherein the nucleic acid sequence encoding the exogenous TdT is located at a RAG1 locus, a RAG2 locus, a TCRα chain locus, a TCRβ chain locus, a TCRγ chain locus and/or a TCRδ chain locus.

In exemplary embodiment 106, provided herein is the genetically modified non-human animal of any one of embodiments 99 to 105, wherein the nucleic acid sequence encoding the exogenous TdT is not operably linked to a constitutive transcriptional control element.

In exemplary embodiment 107, provided herein is the genetically modified non-human animal of any one of embodiments 99 to 106, wherein the exogenous TdT is not constitutively expressed.

In exemplary embodiment 108, provided herein is the genetically modified non-human animal of any one of embodiments 99 to 107, wherein the human TCR variable region gene segments are human TCRα variable region gene segments.

In exemplary embodiment 109, provided herein is the genetically modified non-human animal of any one of embodiments 99 to 107, wherein the human TCR variable region gene segments are human TCRβ variable region gene segments.

In exemplary embodiment 110, provided herein is the genetically modified non-human animal of any one of embodiments 99 to 108, wherein the TCR constant region gene is a TCRα constant region gene.

In exemplary embodiment 111, provided herein is the genetically modified non-human animal of any one of embodiments 99 to 107 and 109, wherein the TCR constant region gene is a TCRβ constant region gene.

In exemplary embodiment 112, provided herein is the genetically modified non-human animal of any one of embodiments 99 to 111, wherein the TCR constant region gene is of endogenous species origin.

In exemplary embodiment 113, provided herein is the genetically modified non-human animal of any one of embodiments 99 to 111, wherein the TCR constant region gene is a mouse constant region gene.

In exemplary embodiment 114, provided herein is the genetically modified non-human animal of any one of embodiments 99 to 111, wherein the TCR constant region gene is a rat constant region gene.

In exemplary embodiment 115, provided herein is the genetically modified non-human animal of any one of embodiments 99 to 111, wherein the TCR constant region gene is a human constant region gene.

In exemplary embodiment 116, provided herein is the genetically modified non-human animal of any one of embodiments 99 to 115, wherein the TCR variable region and the TCR constant region gene are located at an endogenous TCR locus.

In exemplary embodiment 117, provided herein is the genetically modified non-human animal of any one of embodiments 99 to 108, 110, 112-115, wherein the endogenous TCR locus is an endogenous TCRα locus.

In exemplary embodiment 118, provided herein is the genetically modified non-human animal of any one of embodiments 99-107, 109, 111-115, wherein the endogenous TCR locus is an endogenous TCRβ locus.

In exemplary embodiment 119, provided herein is the genetically modified non-human animal of any one of embodiments 99 to 118, wherein the TCR variable region comprises TCR variable region intergenic sequences of human origin.

In exemplary embodiment 120, provided herein is the genetically modified non-human animal of any one of embodiments 99 to 118, wherein the TCR variable region comprises TCR variable region intergenic sequences of endogenous species origin.

In exemplary embodiment 121, provided herein is the genetically modified non-human animal of any one of embodiments 99 to 120, further comprising in its genome an inactivated endogenous TCR locus.

In exemplary embodiment 122, provided herein is the genetically modified non-human animal of embodiment 121, wherein the inactivated endogenous TCR locus is a TCRα locus.

In exemplary embodiment 123, provided herein is the genetically modified non-human animal of embodiment 121, wherein the inactivated endogenous TCR locus is a TCRβ locus.

In exemplary embodiment 124, provided herein is the genetically modified non-human animal of any one of embodiments 99 to 123, wherein the unrearranged human TCR variable region gene segments undergo rearrangement during T cell development to generate rearranged TCR variable region genes in the T cells of the non-human animal.

In exemplary embodiment 125, provided herein is the genetically modified non-human animal of embodiment 124, wherein at least 10% of the rearranged variable region genes comprise non-template additions.

In exemplary embodiment 126, provided herein is the genetically modified non-human animal of embodiment 124, wherein at least 20% of the rearranged variable region genes comprise non-template additions.

In exemplary embodiment 127, provided herein is the genetically modified non-human animal of embodiment 124, wherein at least 40% of the rearranged variable region genes comprise non-template additions.

In exemplary embodiment 128, provided herein is the genetically modified non-human animal of any one of embodiments 124 to 127, wherein the animal expresses TCRs comprising a variable domain encoded by the rearranged TCR variable region gene and a constant domain encoded by the TCR constant region gene.

In exemplary embodiment 129, provided herein is a genetically modified non-human animal comprising in its genome: a nucleic acid sequence encoding an exogenous Terminal Deoxynucleotidyltransferase (TdT); and an immunoglobulin variable region comprising unrearranged human immunoglobulin variable region gene segments operably linked to a TCR constant region gene.

In exemplary embodiment 130, provided herein is the genetically modified non-human animal of embodiment 129, wherein the exogenous TdT is human TdT.

In exemplary embodiment 131, provided herein is the genetically modified non-human animal of embodiment 129 or 130, wherein the nucleic acid sequence encoding the exogenous TdT is operably linked to a transcriptional control element.

In exemplary embodiment 132, provided herein is the genetically modified non-human animal of embodiment 131, wherein the transcriptional control element drives expression of the nucleic acid sequence encoding the exogenous TdT in CD4/CD8 double-negative (DN) thymocytes and/or CD4/CD8 double-positive (DP) thymocytes.

In exemplary embodiment 133, provided herein is the genetically modified non-human animal of embodiment 131, wherein the transcriptional control element is a RAG1 transcriptional control element, a RAG2 transcriptional control element, a TCRα transcriptional control element, a TCRβ transcriptional control element, a TCRγ transcriptional control element and/or a TCRδ transcriptional control element.

In exemplary embodiment 134, provided herein is the genetically modified non-human animal of any one of embodiments 131 to 132, wherein the non-human animal expresses the exogenous TdT in DN thymocytes and/or DP thymocytes.

In exemplary embodiment 135, provided herein is the genetically modified non-human animal of any one of embodiments 129 to 134, wherein the nucleic acid sequence encoding the exogenous TdT is located at a RAG1 locus, a RAG2 locus, a TCRα chain locus, a TCRβ chain locus, a TCRγ chain locus and/or a TCRδ chain locus.

In exemplary embodiment 136, provided herein is the genetically modified non-human animal of any one of embodiments 129 to 135, wherein the nucleic acid sequence encoding the exogenous TdT is not operably linked to a constitutive transcriptional control element.

In exemplary embodiment 137, provided herein is the genetically modified non-human animal of any one of embodiments 129 to 136, wherein the exogenous TdT is not constitutively expressed.

In exemplary embodiment 138, provided herein is the genetically modified non-human animal of any one of embodiments 129 to 137, wherein the human immunoglobulin variable region gene segments are human light chain variable region gene segments.

In exemplary embodiment 139, provided herein is the genetically modified non-human animal of embodiment 138, wherein the human light chain variable region gene segments are κ gene segments.

In exemplary embodiment 140, provided herein is the genetically modified non-human animal of embodiment 138, wherein the human light chain variable region gene segments are λ gene segments.

In exemplary embodiment 141, provided herein is the genetically modified non-human animal of any one of embodiments 138 to 140, wherein at least 10% of the V-J immunoglobulin light chain junctions in the animal comprise non-template additions.

In exemplary embodiment 142, provided herein is the genetically modified non-human animal of embodiment 141, wherein at least 20% of the V-J immunoglobulin light chain junctions in the animal comprise non-template additions.

In exemplary embodiment 143, provided herein is the genetically modified non-human animal of embodiment 141, wherein at least 40% of the V-J immunoglobulin light chain junctions in the animal comprise non-template additions.

In exemplary embodiment 144, provided herein is the genetically modified non-human animal of any one of embodiments 129 to 137, wherein the human immunoglobulin variable region gene segments are human heavy chain variable region gene segments.

In exemplary embodiment 145, provided herein is the genetically modified non-human animal of any one of embodiments 129 to 143, wherein the TCR constant region gene is a TCRα constant region gene.

In exemplary embodiment 146, provided herein is the genetically modified non-human animal of embodiments 145, wherein the immunoglobulin variable region and the TCRα constant region gene are located at an endogenous TCRα locus.

In exemplary embodiment 147, provided herein is the genetically modified non-human animal of embodiment 144, wherein the TCR constant region gene is a TCRβ constant region gene.

In exemplary embodiment 148, provided herein is the genetically modified non-human animal of embodiment 147, wherein the immunoglobulin variable region and the TCRβ constant region gene are located at an endogenous TCRβ locus.

In exemplary embodiment 149, provided herein is the genetically modified non-human animal of any one of embodiments 129 to 148, wherein the TCR constant region gene is of endogenous species origin.

In exemplary embodiment 150, provided herein is the genetically modified non-human animal of any one of embodiments 129 to 148, wherein the TCR constant region gene is a mouse constant region gene.

In exemplary embodiment 151, provided herein is the genetically modified non-human animal of any one of embodiments 129 to 148, wherein the TCR constant region gene is a rat constant region gene.

In exemplary embodiment 152, provided herein is the genetically modified non-human animal of any one of embodiments 129 to 148, wherein the TCR constant region gene is a human constant region gene.

In exemplary embodiment 153, provided herein is the genetically modified non-human animal of any one of embodiments 129 to 152, wherein the immunoglobulin variable region comprises immunoglobulin variable region intergenic sequences of human origin.

In exemplary embodiment 154, provided herein is the genetically modified non-human animal of any one of embodiments 141 to 152, wherein the immunoglobulin variable region comprises immunoglobulin variable region intergenic sequences of endogenous species origin.

In exemplary embodiment 155, provided herein is the genetically modified non-human animal of any one of embodiments 141 to 152, wherein the immunoglobulin variable region comprises immunoglobulin variable region intergenic sequences of mouse origin.

In exemplary embodiment 156, provided herein is the genetically modified non-human animal of any one of embodiments 141 to 152, wherein the immunoglobulin variable region comprises immunoglobulin variable region intergenic sequences of rat origin.

In exemplary embodiment 157, provided herein is the genetically modified non-human animal of any one of embodiments 141 to 155, further comprising in its genome an inactivated endogenous immunoglobulin locus.

In exemplary embodiment 158, provided herein is the genetically modified non-human animal of embodiment 157, wherein the inactivated endogenous immunoglobulin locus is an endogenous immunoglobulin heavy chain locus.

In exemplary embodiment 159, provided herein is the genetically modified non-human animal of embodiment 158, wherein the endogenous immunoglobulin heavy chain locus is inactivated by deletion of at least part of the variable region of the endogenous heavy chain locus.

In exemplary embodiment 160, provided herein is the genetically modified non-human animal of embodiment 159, wherein the deletion of the at least part of the variable region comprises deletion of the J gene segments of the variable region.

In exemplary embodiment 161, provided herein is the genetically modified non-human animal of embodiment 158, wherein the endogenous immunoglobulin heavy chain locus is inactivated by deletion of at least part of the constant region of the endogenous heavy chain locus.

In exemplary embodiment 162, provided herein is the genetically modified non-human animal of embodiment 161, wherein the deletion of the at least part of the constant region comprises deletion of the Cμ gene of the constant region.

In exemplary embodiment 163, provided herein is the genetically modified non-human animal of embodiment 157, wherein the inactivated endogenous immunoglobulin locus is an endogenous immunoglobulin κ chain locus.

In exemplary embodiment 164, provided herein is the genetically modified non-human animal of embodiment 163, wherein the endogenous immunoglobulin κ chain locus is inactivated by deletion of at least part of the variable region of the endogenous κ chain locus.

In exemplary embodiment 165, provided herein is the genetically modified non-human animal of embodiment 164, wherein the deletion of the at least part of the variable region comprises deletion of the J gene segments of the variable region.

In exemplary embodiment 166, provided herein is the genetically modified non-human animal of embodiment 163, wherein the endogenous immunoglobulin κ locus is inactivated by deletion of at least part of the constant region of the endogenous κ chain locus.

In exemplary embodiment 167, provided herein is the genetically modified non-human animal of embodiment 164, wherein the deletion of the at least part of the constant region comprises deletion of the Cκ gene of the constant region.

In exemplary embodiment 168, provided herein is the genetically modified non-human animal of embodiment 157, wherein the inactivated endogenous immunoglobulin locus is an endogenous immunoglobulin λ chain locus.

In exemplary embodiment 169, provided herein is the genetically modified non-human animal of embodiment 168, wherein the endogenous immunoglobulin λ chain locus is inactivated by deletion of at least part of a V-J-C cluster of the endogenous λ chain locus.

In exemplary embodiment 170, provided herein is the genetically modified non-human animal of any one of embodiments 129 to 169, wherein the unrearranged human immunoglobulin variable region gene segments undergo rearrangement during T cell development to generate rearranged immunoglobulin variable region genes in the T cells of the non-human animal.

In exemplary embodiment 171, provided herein is the genetically modified non-human animal of embodiment 170, wherein at least 10% of the rearranged variable region genes comprise non-template additions.

In exemplary embodiment 172, provided herein is the genetically modified non-human animal of embodiment 170, wherein at least 20% of the rearranged variable region genes comprise non-template additions.

In exemplary embodiment 173, provided herein is the genetically modified non-human animal of embodiment 170, wherein at least 40% of the rearranged variable region genes comprise non-template additions.

In exemplary embodiment 174, provided herein is the genetically modified non-human animal of any one of embodiments 170 to 173, wherein the animal expresses chimeric antigen receptors comprising a variable domain encoded by the rearranged variable region gene and a constant domain encoded by the TCR constant region gene.

In exemplary embodiment 175, provided herein is the genetically modified non-human animal of any one of embodiments 1 to 174, wherein the non-human animal is a mammal.

In exemplary embodiment 176, provided herein is the genetically modified non-human animal of embodiment 175, wherein the mammal is a rodent.

In exemplary embodiment 177, provided herein is the genetically modified non-human animal of embodiment 176, wherein the rodent is a rat or a mouse.

In exemplary embodiment 178, provided herein is the genetically modified non-human animal of embodiment 176, wherein the rodent is a mouse.

In exemplary embodiment 179, provided herein is the genetically modified non-human animal of embodiment 176, wherein the rodent is a rat.

In exemplary embodiment 180, provided herein is a method inducing expression of an antibody comprising a human variable domain, the method comprising exposing a genetically modified non-human animal of embodiment 97 to an antigen such that the genetically modified non-human animal produces an antibody comprising a human variable domain specific for the antigen.

In exemplary embodiment 181, provided herein is a method of making a B cell expressing an antibody comprising a human variable domain, the method comprising: (a) exposing a genetically modified non-human animal of embodiment 97 to an antigen; and (b) obtaining a B cell expressing an antibody comprising a human variable domain specific for the antigen from the non-human animal.

In exemplary embodiment 182, provided herein is a method of making a hybridoma expressing an antibody comprising a human variable domain, the method comprising: (a) exposing a genetically modified non-human animal of embodiment 97 to an antigen; (b) obtaining a B cell expressing an antibody comprising a human variable domain specific for the antigen from the non-human animal; and (c) making a hybridoma from the B cell of step (b).

In exemplary embodiment 183, provided herein is a method of making a nucleic acid encoding a human immunoglobulin variable domain, the method comprising: (a) exposing a genetically modified non-human animal of embodiment 97 to an antigen; and (b) obtaining a nucleic acid encoding a human immunoglobulin variable domain specific for the antigen from the non-human animal.

In exemplary embodiment 184, provided herein is a method of making a nucleic acid encoding a human immunoglobulin variable domain, the method comprising: (a) exposing a genetically modified non-human animal of embodiment 97 to an antigen; (b) obtaining a B cell expressing an antibody comprising a human variable domain specific for the antigen from the non-human animal; (c) making a hybridoma from the B cell of step (b); and (d) obtaining a nucleic acid encoding a human immunoglobulin variable domain specific for the antigen from the hybridoma.

In exemplary embodiment 185, provided herein is a method of making an antibody comprising a human variable domain and a human constant domain, the method comprising: (a) exposing a genetically modified non-human animal of embodiment 97 to an antigen; (b) obtaining a nucleic acid encoding a human immunoglobulin variable domain specific for the antigen from the non-human animal; (c) operably linking the nucleic acid encoding the immunoglobulin variable domain with a nucleic acid encoding a human immunoglobulin constant domain in a host cell; and (d) culturing the host cell under conditions such that the host cell expresses a human antibody comprising the immunoglobulin variable domain and the immunoglobulin constant domain.

In exemplary embodiment 186, provided herein is a method for making an antibody comprising a human variable domain and a human constant domain specific to an antigen, the method comprising: (a) exposing a non-human animal of embodiment 97 to an antigen; (b) obtaining a B cell expressing an antibody comprising a human variable domain specific for the antigen from the non-human animal; (c) making a hybridoma from the B cell of step (b); (d) obtaining a nucleic acid encoding a human immunoglobulin variable domain specific for the antigen from the hybridoma; (e) operably linking the nucleic acid encoding the immunoglobulin variable domain with a nucleic acid encoding a human immunoglobulin constant domain in a host cell; and (0 culturing the host cell under conditions such that the host cell expresses a human antibody comprising the immunoglobulin variable domain and the immunoglobulin constant domain.

In exemplary embodiment 187, provided herein is a method of making a T cell expressing a T cell receptor (TCR) comprising a human variable domain specific to a peptide presented on a MHC, the method comprising: (a) exposing a genetically modified non-human animal of embodiment 128 to an antigen comprising a peptide or a nucleic acid encoding an antigen comprising a peptide such that the peptide is presented on a MHC in the non-human animal; and (b) obtaining a T cell expressing a TCR specific for the peptide presented on the MHC from the genetically modified non-human animal of (a).

In exemplary embodiment 188, provided herein is a method of making a T cell hybridoma expressing a T cell receptor (TCR) comprising a human variable domain specific to a peptide presented on a MHC, the method comprising: (a) exposing a genetically modified non-human animal of embodiment 128 to an antigen comprising a peptide or a nucleic acid encoding an antigen comprising a peptide such that the peptide is presented on a MHC in the non-human animal; (b) obtaining a T cell expressing a TCR specific for the peptide presented on the MHC from the genetically modified non-human animal of (a); and (c) making a T cell hybridoma from the T cell of step (b).

In exemplary embodiment 189, provided herein is a method for making a nucleic acid encoding a human T cell receptor (TCR) variable domain specific to a peptide presented on a MHC, the method comprising: (a) exposing a non-human animal of embodiment 128 to an antigen comprising a peptide or a nucleic acid encoding an antigen comprising a peptide such that the peptide is presented on a MHC in the non-human animal; (b) obtaining a T cell expressing a TCR specific for the peptide presented on the MHC from the genetically modified non-human animal of (a); and (c) isolating a nucleic acid encoding a human TCR variable domain of the TCR from the T cell.

In exemplary embodiment 190, provided herein is a method for making a T cell receptor (TCR) having a human variable domain and a human constant domain specific to a peptide presented on a MHC, the method comprising: (a) exposing a non-human animal of embodiment 128 to an antigen comprising a peptide or a nucleic acid encoding an antigen comprising a peptide such that the peptide is presented on a MHC in the non-human animal; (b) obtaining a T cell expressing a TCR specific for the peptide presented on the MHC from the genetically modified non-human animal of (a); (c) isolating a nucleic acid encoding a TCR variable domain of the TCR from the T cell; and (d) operably linking the nucleic acid encoding the TCR variable domain with a TCR constant domain in a cell such that the cell expresses a TCR comprising the TCR variable domain and the TCR constant domain.

In exemplary embodiment 191, provided herein is a method of making T cell expressing a chimeric antigen receptor (CAR) comprising a human immunoglobulin variable domain and an immunoglobulin constant specific to a peptide presented on a MHC, the method comprising: (a) exposing a genetically modified non-human animal of embodiment 174 to an antigen comprising a peptide or a nucleic acid encoding an antigen comprising a peptide such that the peptide is presented on a MHC in the non-human animal; and (b) obtaining a T cell expressing a CAR specific for the peptide presented on the MHC from the genetically modified non-human animal of (a).

In exemplary embodiment 192, provided herein is a method of making T cell hybridoma expressing a chimeric antigen receptor (CAR) comprising a human TCR variable domain and a immunoglobulin constant domain specific to a peptide presented on a MHC, the method comprising: (a) exposing a genetically modified non-human animal of embodiment 174 to an antigen comprising a peptide or a nucleic acid encoding an antigen comprising a peptide such that the peptide is presented on a MHC in the non-human animal; (b) obtaining a T cell expressing a CAR specific for the peptide presented on the MHC from the genetically modified non-human animal of (a); and (c) making a T cell hybridoma from the T cell of step (b).

In exemplary embodiment 193, provided herein is a method for making a nucleic acid encoding a human immunoglobulin variable domain specific to a peptide presented on a MHC, the method comprising: (a) exposing a non-human animal of embodiment 174 to an antigen comprising a peptide or a nucleic acid encoding an antigen comprising a peptide such that the peptide is presented on a MHC in the non-human animal; (b) obtaining a T cell expressing a chimeric antigen receptor (CAR) specific for the peptide presented on the MHC from the genetically modified non-human animal of (a); and (c) isolating a nucleic acid encoding a human TCR variable domain of the CAR from the T cell.

In exemplary embodiment 194, provided herein is a method for making an antibody having a human variable domain and a human constant domain specific to a peptide presented on a MHC, the method comprising: (a) exposing a non-human animal of embodiment 174 to an antigen comprising a peptide or a nucleic acid encoding an antigen comprising a peptide such that the peptide is presented on a MHC in the non-human animal; (b) obtaining a T cell expressing a chimeric antigen receptor (CAR) specific for the peptide presented on the MHC from the genetically modified non-human animal of (a); (c) isolating a nucleic acid encoding a human immunoglobulin variable domain of the CAR from the T cell; and (d) operably linking the nucleic acid encoding the human immunoglobulin variable domain with a human immunoglobulin constant domain in a cell such that the cell expresses an antibody comprising the human immunoglobulin variable domain and the human immunoglobulin constant domain.

In exemplary embodiment 195, provided herein is the method of any one of embodiments 180 to 194, wherein the non-human animal is a mammal.

In exemplary embodiment 196, provided herein is the method of embodiment 195, wherein the mammal is a rodent.

In exemplary embodiment 197, provided herein is the method of embodiment 196, wherein the rodent is a rat or a mouse.

In exemplary embodiment 198, provided herein is an antibody generated according to the method of embodiment 180, 185, 186 or 194.

In exemplary embodiment 199, provided herein is a cell generated according to the method of embodiment 181, 187 or 191.

In exemplary embodiment 200, provided herein is a hybridoma generated according to the method of embodiment 182, 188 or 192.

In exemplary embodiment 201, provided herein is a nucleic acid generated according to the method of embodiment 183, 184, 189 or 193.

In exemplary embodiment 202, provided herein is a genetically modified non-human animal ES cell comprising in its genome a nucleic acid sequence encoding human Terminal Deoxynucleotidyltransferase (hTdT).

In exemplary embodiment 203, provided herein is the genetically modified non-human animal ES cell of embodiment 202, wherein the nucleic acid sequence encoding hTdT is operably linked to a transcriptional control element.

In exemplary embodiment 204, provided herein is the genetically modified non-human animal ES cell of embodiment 203, wherein the transcriptional control element drives expression of the nucleic acid sequence encoding hTdT in pro-B cells and/or pre-B cells.

In exemplary embodiment 205, provided herein is the genetically modified non-human animal ES cell of embodiment 203, wherein the transcriptional control element is selected from the group consisting of a RAG1 transcriptional control element, a RAG2 transcriptional control element, an immunoglobulin heavy chain transcriptional control element, an immunoglobulin κ light chain transcriptional control element and/or an immunoglobulin λ light chain transcriptional control element.

In exemplary embodiment 206, provided herein is the genetically modified non-human animal ES cell of any one of embodiments 202 to 204, wherein the non-human animal expresses hTdT in pro-B cells and/or pre-B cells.

In exemplary embodiment 207, provided herein is the genetically modified non-human animal ES cell of embodiment 203, wherein the transcriptional control element drives expression of the nucleic acid sequence encoding hTdT in CD4/CD8 double-negative (DN) thymocytes and/or CD4/CD8 double-positive (DP) thymocytes.

In exemplary embodiment 208, provided herein is the genetically modified non-human animal ES cell of embodiment 203, wherein the transcriptional control element is a RAG1 transcriptional control element, a RAG2 transcriptional control element, a TCRα transcriptional control element, a TCRβ transcriptional control element, a TCRγ transcriptional control element and/or a TCRδ transcriptional control element.

In exemplary embodiment 209, provided herein is the genetically modified non-human animal ES cell of any one of embodiments 202 to 207, wherein a non-human animal derived from the ES cell expresses hTdT in DN thymocytes and/or DP thymocytes.

In exemplary embodiment 210, provided herein is the genetically modified non-human animal ES cell of any one of embodiments 202 to 209, wherein the nucleic acid sequence encoding hTdT is located at an immunoglobulin κ light chain locus, an immunoglobulin λ light chain locus, an immunoglobulin heavy chain locus, a RAG1 locus, a RAG2 locus, a TCRα chain locus, a TCRβ chain locus, a TCRγ chain locus and/or a TCRδ chain locus.

In exemplary embodiment 211, provided herein is the genetically modified non-human animal ES cell of any one of embodiments 202 to 210, wherein the nucleic acid sequence encoding hTdT is not operably linked to a constitutive transcriptional control element.

In exemplary embodiment 212, provided herein is the genetically modified non-human animal ES cell of any one of embodiments 202 to 211, wherein the hTdT is not constitutively expressed in a non-human animal derived from the non-human animal ES cell.

In exemplary embodiment 213, provided herein is the genetically modified non-human animal ES cell of any one of embodiments 202 to 212, wherein at least 10% of the V-J immunoglobulin light chain junctions in a non-human animal derived from the ES cell comprise non-template additions.

In exemplary embodiment 214, provided herein is the genetically modified non-human animal ES cell of embodiment 213, wherein at least 20% of the V-J immunoglobulin light chain junctions in the animal derived from the ES cell comprise non-template additions.

In exemplary embodiment 215, provided herein is the genetically modified non-human animal ES cell of embodiment 213, wherein at least 40% of the V-J immunoglobulin light chain junctions in the animal derived from the ES cell comprise non-template additions.

In exemplary embodiment 216, provided herein is a genetically modified non-human animal ES cell comprising in its genome: a nucleic acid sequence encoding an exogenous Terminal Deoxynucleotidyltransferase (TdT); and an immunoglobulin variable region comprising unrearranged human immunoglobulin variable region gene segments operably linked to an immunoglobulin constant region gene.

In exemplary embodiment 217, provided herein is the genetically modified non-human animal ES cell of embodiment 216, wherein the exogenous TdT is human TdT.

In exemplary embodiment 218, provided herein is the genetically modified non-human animal ES cell of embodiment 216 or 217, wherein the nucleic acid sequence encoding the exogenous TdT is operably linked to a transcriptional control element.

In exemplary embodiment 219, provided herein is the genetically modified non-human animal ES cell of embodiment 218, wherein the transcriptional control element drives expression of the nucleic acid sequence encoding the exogenous TdT in pro-B cells and/or pre-B cells.

In exemplary embodiment 220, provided herein is the genetically modified non-human animal ES cell of embodiment 218, wherein the transcriptional control element is selected from the group consisting of a RAG1 transcriptional control element, a RAG2 transcriptional control element, an immunoglobulin heavy chain transcriptional control element, an immunoglobulin κ light chain transcriptional control element and/or an immunoglobulin λ light chain transcriptional control element.

In exemplary embodiment 221, provided herein is the genetically modified non-human animal ES cell of any one of embodiments 216 to 220, wherein a non-human animal derived from the ES cell expresses the exogenous TdT in pro-B cells and/or pre-B cells.

In exemplary embodiment 222, provided herein is the genetically modified non-human animal ES cell of embodiment 218, wherein the transcriptional control element drives expression of the nucleic acid sequence encoding the exogenous TdT in CD4/CD8 double-negative (DN) thymocytes and/or CD4/CD8 double-positive (DP) thymocytes.

In exemplary embodiment 223, provided herein is the genetically modified non-human animal ES cell of embodiment 218, wherein the transcriptional control element is a RAG1 transcriptional control element or a RAG2 transcriptional control element.

In exemplary embodiment 224, provided herein is the genetically modified non-human animal ES cell of any one of embodiments 216 to 223, wherein a non-human animal derived from the ES cell expresses the exogenous TdT in DN thymocytes and/or DP thymocytes.

In exemplary embodiment 225, provided herein is the genetically modified non-human animal ES cell of any one of embodiments 216 to 224, wherein the nucleic acid sequence encoding the exogenous TdT is located at an immunoglobulin κ light chain locus, an immunoglobulin λ light chain locus, an immunoglobulin heavy chain locus, a RAG1 locus, a RAG2 locus, a TCRα chain locus, a TCRβ chain locus, a TCRγ chain locus and/or a TCRδ chain locus.

In exemplary embodiment 226, provided herein is the genetically modified non-human animal ES cell of any one of embodiments 216 to 225, wherein the nucleic acid sequence encoding the exogenous TdT is not operably linked to a constitutive transcriptional control element.

In exemplary embodiment 227, provided herein is the genetically modified non-human animal ES cell of any one of embodiments 216 to 226, wherein the exogenous TdT is not constitutively expressed in a non-human animal derived from the ES cell.

In exemplary embodiment 228, provided herein is the genetically modified non-human animal ES cell of any one of embodiments 216 to 227, wherein at least 10% of the V-J immunoglobulin light chain junctions in a non-human animal derived from the ES cell comprise non-template additions.

In exemplary embodiment 229, provided herein is the genetically modified non-human animal ES cell of embodiment 228, wherein at least 20% of the V-J immunoglobulin light chain junctions in the animal comprise non-template additions.

In exemplary embodiment 230, provided herein is the genetically modified non-human animal ES cell of embodiment 228, wherein at least 40% of the V-J immunoglobulin light chain junctions in the animal comprise non-template additions.

In exemplary embodiment 231, provided herein is the genetically modified non-human animal ES cell of any one of embodiments 216 to 227, wherein the human immunoglobulin variable region gene segments are human heavy chain variable region gene segments.

In exemplary embodiment 232, provided herein is the genetically modified non-human animal ES cell of embodiment 231, wherein the constant region gene is a heavy chain constant region gene.

In exemplary embodiment 233, provided herein is the genetically modified non-human animal ES cell of embodiment 232, wherein the heavy chain constant region gene is a Cμ gene, a Cδ gene, a Cγ gene, a Cε gene or a Cα gene.

In exemplary embodiment 234, provided herein is the genetically modified non-human animal ES cell of embodiment 232 or 233, wherein the heavy chain constant region gene is of endogenous species origin.

In exemplary embodiment 235, provided herein is the genetically modified non-human animal ES cell of embodiment 232 or 233, wherein the heavy chain constant region gene is a mouse constant region gene.

In exemplary embodiment 236, provided herein is the genetically modified non-human animal ES cell of embodiment 232 or 233, wherein the heavy chain constant region gene is a rat constant region gene.

In exemplary embodiment 237, provided herein is the genetically modified non-human animal ES cell of embodiment 232 or 233, wherein the heavy chain constant region gene is a human constant region gene.

In exemplary embodiment 238, provided herein is the genetically modified non-human animal ES cell of embodiment 232 or 233, wherein the heavy chain constant region gene has a human CH1 domain and non-human CH2 and CH3 domains.

In exemplary embodiment 239, provided herein is the genetically modified non-human animal ES cell of embodiment 238, wherein the non-human CH2 and CH3 domains are of endogenous species origin.

In exemplary embodiment 240, provided herein is the genetically modified non-human animal ES cell of embodiment 238, wherein the non-human CH2 and CH3 domains are mouse CH2 and CH3 domains.

In exemplary embodiment 241, provided herein is the genetically modified non-human animal ES cell of embodiment 238, wherein the non-human CH2 and CH3 domains are rat CH2 and CH3 domains.

In exemplary embodiment 242, provided herein is the genetically modified non-human animal ES cell of embodiments 216-241, wherein the animal lacks a functional CH1 domain in an immunoglobulin heavy chain constant region selected from IgG, IgA, IgE, IgD, or a combination thereof.

In exemplary embodiment 243, provided herein is the genetically modified non-human animal ES cell of any one of embodiments 232 to 242, wherein the immunoglobulin variable region and the immunoglobulin constant region gene are located at an endogenous immunoglobulin heavy chain locus.

In exemplary embodiment 244, provided herein is the genetically modified non-human animal ES cell of any one of embodiments 231 to 243, further comprising in its genome an immunoglobulin variable region comprising unrearranged human light chain variable region gene segments operably linked to a second immunoglobulin constant region gene.

In exemplary embodiment 245, provided herein is the genetically modified non-human animal ES cell of embodiment 244, wherein the human immunoglobulin variable region gene segments operably linked to the second immunoglobulin constant region gene are human κ chain variable region gene segments.

In exemplary embodiment 246, provided herein is the genetically modified non-human animal ES cell of embodiment 244, wherein the human immunoglobulin variable region gene segments operably linked to the second immunoglobulin constant region gene are human λ chain variable region gene segments.

In exemplary embodiment 247, provided herein is the genetically modified non-human animal ES cell of any one of embodiments 244 to 246, wherein the second constant region gene is a light chain constant region gene.

In exemplary embodiment 248, provided herein is the genetically modified non-human animal ES cell of embodiment 247, wherein the second constant region gene is a κ constant region gene.

In exemplary embodiment 249, provided herein is the genetically modified non-human animal ES cell of embodiment 247, wherein the second constant region gene is a λ constant region gene.

In exemplary embodiment 250, provided herein is the genetically modified non-human animal ES cell of any one of embodiments 244 to 249, wherein the second constant region gene is of endogenous species origin.

In exemplary embodiment 251, provided herein is the genetically modified non-human animal ES cell of any one of embodiments 244 to 249, wherein the second constant region gene is a mouse constant region gene.

In exemplary embodiment 252, provided herein is the genetically modified non-human animal ES cell of any one of embodiments 244 to 249, wherein the second constant region gene is a rat constant region gene.

In exemplary embodiment 253, provided herein is the genetically modified non-human animal ES cell of any one of embodiments 244 to 249, wherein the second constant region gene is a human constant region gene.

In exemplary embodiment 254, provided herein is the genetically modified non-human animal ES cell of any one of embodiments 244 to 253, wherein the immunoglobulin variable region operably linked to the second immunoglobulin constant region gene and the second immunoglobulin constant region gene are located at an endogenous immunoglobulin light chain locus.

In exemplary embodiment 255, provided herein is the genetically modified non-human animal ES cell of embodiment 254, wherein the second constant region gene is a κ constant region gene and the endogenous immunoglobulin light chain locus is an immunoglobulin κ locus.

In exemplary embodiment 256, provided herein is the genetically modified non-human animal ES cell of embodiment 254, wherein the second constant region gene is a λ constant region gene and endogenous immunoglobulin light chain locus is an immunoglobulin λ locus.

In exemplary embodiment 257, provided herein is the genetically modified non-human animal ES cell of any one of embodiments 231 to 243, further comprising in its genome an immunoglobulin variable region comprising rearranged human light chain variable region (V/J) gene segments operably linked to a second immunoglobulin constant region gene.

In exemplary embodiment 258, provided herein is the genetically modified non-human animal ES cell of embodiment 257, wherein the rearranged human light chain variable region (V/J) gene segments operably linked to a second immunoglobulin constant region gene comprise a Vκ gene segments selected from Vκ1-39 and Vκ3-20, rearranged to a Jκ gene segment.

In exemplary embodiment 259, provided herein is the genetically modified non-human animal ES cell of embodiment 258, wherein the animal comprises in its genome an immunoglobulin light chain variable region comprising a Vκ1-39/Jκ5 or a Vκ3-20/Jκ1 sequence.

In exemplary embodiment 260, provided herein is the genetically modified non-human animal ES cell of any one of embodiments 231 to 243, further comprising in its genome an immunoglobulin variable region comprising a limited repertoire of human light chain variable region (V and J) gene segments operably linked to a second immunoglobulin constant region gene.

In exemplary embodiment 261, provided herein is the genetically modified non-human animal ES cell of embodiment 260, wherein the limited repertoire of human light chain variable region (V and J) gene segments operably linked to a second immunoglobulin constant region gene comprises two V gene segments and at least two, preferably five, J gene segments.

In exemplary embodiment 262, provided herein is the genetically modified non-human animal ES cell of embodiment 261, wherein the two V gene segments are Vk1-39 and Vk3-20 gene segments.

In exemplary embodiment 263, provided herein is the genetically modified non-human animal ES cell of any one of embodiments 216 to 230, wherein the human immunoglobulin variable region gene segments are human light chain variable region gene segments.

In exemplary embodiment 264, provided herein is the genetically modified non-human animal ES cell of embodiment 263, wherein the human immunoglobulin variable region gene segments are human κ chain variable region gene segments.

In exemplary embodiment 265, provided herein is the genetically modified non-human animal ES cell of embodiment 263, wherein the human immunoglobulin variable region gene segments are human λ chain variable region gene segments.

In exemplary embodiment 266, provided herein is the genetically modified non-human animal ES cell of any one of embodiments 263 to 265, wherein the constant region gene is a light chain constant region gene.

In exemplary embodiment 267, provided herein is the genetically modified non-human animal ES cell of embodiment 266, wherein the constant region gene is a κ constant region gene.

In exemplary embodiment 268, provided herein is the genetically modified non-human animal ES cell of embodiment 266, wherein the constant region gene is a λ constant region gene.

In exemplary embodiment 269, provided herein is the genetically modified non-human animal ES cell of any one of embodiments 263 to 265, wherein the constant region gene is a heavy chain constant region gene.

In exemplary embodiment 270, provided herein is the genetically modified non-human animal ES cell of any one of embodiments 263 to 269, wherein the constant region gene is of endogenous species origin.

In exemplary embodiment 271, provided herein is the genetically modified non-human animal ES cell of any one of embodiments 263 to 269, wherein the constant region gene is a mouse constant region gene.

In exemplary embodiment 272, provided herein is the genetically modified non-human animal ES cell of any one of embodiments 263 to 269, wherein the constant region gene is a rat constant region gene.

In exemplary embodiment 273, provided herein is the genetically modified non-human animal ES cell of any one of embodiments 263 to 269, wherein the constant region gene is a human constant region gene.

In exemplary embodiment 274, provided herein is the genetically modified non-human animal ES cell of any one of embodiments 263 to 273, wherein the immunoglobulin variable region and the immunoglobulin constant region gene are located at an endogenous immunoglobulin light chain locus.

In exemplary embodiment 275, provided herein is the genetically modified non-human animal ES cell of embodiment 274, wherein the constant region gene is a κ constant region gene and the endogenous immunoglobulin light chain locus is an immunoglobulin κ locus.

In exemplary embodiment 276, provided herein is the genetically modified non-human animal ES cell of embodiment 274, wherein the constant region gene is a λ constant region gene and the endogenous immunoglobulin light chain locus is an immunoglobulin λ locus.

In exemplary embodiment 277, provided herein is the genetically modified non-human animal ES cell of any one of embodiments 216 to 276, wherein the immunoglobulin variable region comprises immunoglobulin variable region intergenic sequences of human origin.

In exemplary embodiment 278, provided herein is the genetically modified non-human animal ES cell of any one of embodiments 216 to 276, wherein the immunoglobulin variable region comprises immunoglobulin variable region intergenic sequences of endogenous species origin.

In exemplary embodiment 279, provided herein is the genetically modified non-human animal ES cell of any one of embodiments 216 to 276, wherein the immunoglobulin variable region comprises immunoglobulin variable region intergenic sequences of mouse origin.

In exemplary embodiment 280, provided herein is the genetically modified non-human animal ES cell of any one of embodiments 216 to 276, wherein the immunoglobulin variable region comprises immunoglobulin variable region intergenic sequences of rat origin.

In exemplary embodiment 281, provided herein is the genetically modified non-human animal ES cell of any one of embodiments 216 to 280, further comprising in its genome an inactivated endogenous immunoglobulin locus.

In exemplary embodiment 282, provided herein is the genetically modified non-human animal ES cell of embodiment 281, wherein the inactivated endogenous immunoglobulin locus is an endogenous immunoglobulin heavy chain locus.

In exemplary embodiment 283, provided herein is the genetically modified non-human animal ES cell of embodiment 282, wherein the endogenous immunoglobulin heavy chain locus is inactivated by deletion of at least part of the variable region of the endogenous heavy chain locus.

In exemplary embodiment 284, provided herein is the genetically modified non-human animal ES cell of embodiment 283, wherein the deletion of the at least part of the variable region comprises deletion of the J gene segments of the variable region.

In exemplary embodiment 285, provided herein is the genetically modified non-human animal ES cell of embodiment 282, wherein the endogenous immunoglobulin heavy chain locus is inactivated by deletion of at least part of the constant region of the endogenous heavy chain locus.

In exemplary embodiment 286, provided herein is the genetically modified non-human animal ES cell of embodiment 285, wherein the deletion of the at least part of the constant region comprises deletion of the Cμ gene of the constant region.

In exemplary embodiment 287, provided herein is the genetically modified non-human animal ES cell of embodiment 281, wherein the inactivated endogenous immunoglobulin locus is an endogenous immunoglobulin κ chain locus.

In exemplary embodiment 288, provided herein is the genetically modified non-human animal ES cell of embodiment 287, wherein the endogenous immunoglobulin κ chain locus is inactivated by deletion of at least part of the variable region of the endogenous κ chain locus.

In exemplary embodiment 289, provided herein is the genetically modified non-human animal ES cell of embodiment 288, wherein the deletion of the at least part of the variable region comprises deletion of the J gene segments of the variable region.

In exemplary embodiment 290, provided herein is the genetically modified non-human animal ES cell of embodiment 287, wherein the endogenous immunoglobulin κ locus is inactivated by deletion of at least part of the constant region of the endogenous κ chain locus.

In exemplary embodiment 291, provided herein is the genetically modified non-human animal ES cell of embodiment 290, wherein the deletion of the at least part of the constant region comprises deletion of the Cκ gene of the constant region.

In exemplary embodiment 292, provided herein is the genetically modified non-human animal ES cell of embodiment 281, wherein the inactivated endogenous immunoglobulin locus is an endogenous immunoglobulin λ chain locus.

In exemplary embodiment 293, provided herein is the genetically modified non-human animal ES cell of embodiment 292, wherein the endogenous immunoglobulin λ chain locus is inactivated by deletion of at least part of a V-J-C cluster of the endogenous λ chain locus.

In exemplary embodiment 294, provided herein is the genetically modified non-human animal ES cell of any one of embodiments 216 to 293, wherein the unrearranged human immunoglobulin variable region gene segments undergo rearrangement during B cell development to generate rearranged variable region genes in the B cells of a non-human animal derived from the ES cell.

In exemplary embodiment 295, provided herein is the genetically modified non-human animal ES cell of embodiment 294, wherein at least 10% of the rearranged variable region genes comprise non-template additions in the non-human animal.

In exemplary embodiment 296, provided herein is the genetically modified non-human animal ES cell of embodiment 294, wherein at least 20% of the rearranged variable region genes comprise non-template additions in the non-human animal.

In exemplary embodiment 297, provided herein is the genetically modified non-human animal ES cell of embodiment 294, wherein at least 40% of the rearranged variable region genes comprise non-template additions in the non-human animal.

In exemplary embodiment 298, provided herein is the genetically modified non-human animal ES cell of any one of embodiments 294 to 297, wherein the animal derived from the ES cell expresses antibodies comprising a variable domain encoded by the rearranged variable region gene and a constant domain encoded by the constant region gene.

In exemplary embodiment 299, provided herein is a genetically modified non-human animal ES cell comprising in its genome: a nucleic acid sequence encoding an exogenous Terminal Deoxynucleotidyltransferase (TdT); and an T cell receptor (TCR) variable region comprising unrearranged human TCR variable region gene segments operably linked to a TCR constant region gene.

In exemplary embodiment 300, provided herein is the genetically modified non-human animal ES cell of embodiment 299, wherein the exogenous TdT is human TdT.

In exemplary embodiment 301, provided herein is the genetically modified non-human animal ES cell of embodiment 299 or 300, wherein the nucleic acid sequence encoding the exogenous TdT is operably linked to a transcriptional control element.

In exemplary embodiment 302, provided herein is the genetically modified non-human animal ES cell of embodiment 301, wherein the transcriptional control element drives expression of the nucleic acid sequence encoding the exogenous TdT in CD4/CD8 double-negative (DN) thymocytes and/or CD4/CD8 double-positive (DP) thymocytes.

In exemplary embodiment 303, provided herein is the genetically modified non-human animal ES cell of embodiment 301, wherein the transcriptional control element is a RAG1 transcriptional control element, a RAG2 transcriptional control element, a TCRα transcriptional control element, a TCRβ transcriptional control element, a TCRγ transcriptional control element and/or a TCRδ transcriptional control element.

In exemplary embodiment 304, provided herein is the genetically modified non-human animal ES cell of any one of embodiments 299 to 303, wherein a non-human animal derived from the ES cell expresses the exogenous TdT in DN thymocytes and/or DP thymocytes.

In exemplary embodiment 305, provided herein is the genetically modified non-human animal ES cell of any one of embodiments 299 to 304, wherein the nucleic acid sequence encoding the exogenous TdT is located at a RAG1 locus, a RAG2 locus, a TCRα chain locus, a TCRβ chain locus, a TCRγ chain locus and/or a TCRδ chain locus.

In exemplary embodiment 306, provided herein is the genetically modified non-human animal ES cell of any one of embodiments 299 to 305, wherein the nucleic acid sequence encoding the exogenous TdT is not operably linked to a constitutive transcriptional control element.

In exemplary embodiment 307, provided herein is the genetically modified non-human animal ES cell of any one of embodiments 299 to 306, wherein the exogenous TdT is not constitutively expressed by a non-human animal derived from the ES cell.

In exemplary embodiment 308, provided herein is the genetically modified non-human animal ES cell of any one of embodiments 299 to 307, wherein the human TCR variable region gene segments are human TCRα variable region gene segments.

In exemplary embodiment 309, provided herein is the genetically modified non-human animal ES cell of any one of embodiments 299 to 307, wherein the human TCR variable region gene segments are human TCRβ variable region gene segments.

In exemplary embodiment 310, provided herein is the genetically modified non-human animal ES cell of any one of embodiments 299 to 308, wherein the TCR constant region gene is a TCRα constant region gene.

In exemplary embodiment 311, provided herein is the genetically modified non-human animal ES cell of any one of embodiments 299 to 307 and 309, wherein the TCR constant region gene is a TCRβ constant region gene.

In exemplary embodiment 312, provided herein is the genetically modified non-human animal ES cell of any one of embodiments 299 to 311, wherein the TCR constant region gene is of endogenous species origin.

In exemplary embodiment 313, provided herein is the genetically modified non-human animal ES cell of any one of embodiments 299 to 311, wherein the TCR constant region gene is a mouse constant region gene.

In exemplary embodiment 314, provided herein is the genetically modified non-human animal ES cell of any one of embodiments 299 to 311, wherein the TCR constant region gene is a rat constant region gene.

In exemplary embodiment 315, provided herein is the genetically modified non-human animal ES cell of any one of embodiments 299 to 311, wherein the TCR constant region gene is a human constant region gene.

In exemplary embodiment 316, provided herein is the genetically modified non-human animal ES cell of any one of embodiments 299 to 315, wherein the TCR variable region and the TCR constant region gene are located at an endogenous TCR locus.

In exemplary embodiment 317, provided herein is the genetically modified non-human animal ES cell of any one of embodiments 299 to 308, 310, 313-315, wherein the endogenous TCR locus is an endogenous TCRα locus.

In exemplary embodiment 318, provided herein is the genetically modified non-human animal ES cell of any one of embodiments 299-307, 309, 311-315, wherein the endogenous TCR locus is an endogenous TCRβ locus.

In exemplary embodiment 319, provided herein is the genetically modified non-human animal ES cell of any one of embodiments 299 to 318, wherein the TCR variable region comprises TCR variable region intergenic sequences of human origin.

In exemplary embodiment 320, provided herein is the genetically modified non-human animal ES cell of any one of embodiments 299 to 318, wherein the TCR variable region comprises TCR variable region intergenic sequences of endogenous species origin.

In exemplary embodiment 321, provided herein is the genetically modified non-human animal ES cell of any one of embodiments 299 to 320, further comprising in its genome an inactivated endogenous TCR locus.

In exemplary embodiment 322, provided herein is the genetically modified non-human animal ES cell of embodiment 321, wherein the inactivated endogenous TCR locus is a TCRα locus.

In exemplary embodiment 323, provided herein is the genetically modified non-human animal ES cell of embodiment 321, wherein the inactivated endogenous TCR locus is a TCRβ locus.

In exemplary embodiment 324, provided herein is the genetically modified non-human animal ES cell of any one of embodiments 299 to 323, wherein the unrearranged human TCR variable region gene segments undergo rearrangement during T cell development to generate rearranged TCR variable region genes in the T cells of a non-human animal derived from the ES cell.

In exemplary embodiment 325, provided herein is the genetically modified non-human animal ES cell of embodiment 324, wherein at least 10% of the rearranged variable region genes comprise non-template additions in a non-human animal derived from the ES cell.

In exemplary embodiment 326, provided herein is the genetically modified non-human animal ES cell of embodiment 324, wherein at least 20% of the rearranged variable region genes comprise non-template additions in a non-human animal derived from the ES cell.

In exemplary embodiment 327, provided herein is the genetically modified non-human animal ES cell of embodiment 324, wherein at least 40% of the rearranged variable region genes comprise non-template additions in a non-human animal derived from the ES cell.

In exemplary embodiment 328, provided herein is the genetically modified non-human animal ES cell of any one of embodiments 324 to 327, wherein the animal derived from the ES cell expresses TCRs comprising a variable domain encoded by the rearranged TCR variable region gene and a constant domain encoded by the TCR constant region gene.

In exemplary embodiment 329, provided herein is a genetically modified non-human animal comprising in its genome: a nucleic acid sequence encoding an exogenous Terminal Deoxynucleotidyltransferase (TdT); and an immunoglobulin variable region comprising unrearranged human immunoglobulin variable region gene segments operably linked to a TCR constant region gene.

In exemplary embodiment 330, provided herein is the genetically modified non-human animal ES cell of embodiment 329, wherein the exogenous TdT is human TdT.

In exemplary embodiment 331, provided herein is the genetically modified non-human animal ES cell of embodiment 329 or 330, wherein the nucleic acid sequence encoding the exogenous TdT is operably linked to a transcriptional control element.

In exemplary embodiment 332, provided herein is the genetically modified non-human animal ES cell of embodiment 331, wherein the transcriptional control element drives expression of the nucleic acid sequence encoding the exogenous TdT in CD4/CD8 double-negative (DN) thymocytes and/or CD4/CD8 double-positive (DP) thymocytes.

In exemplary embodiment 333, provided herein is the genetically modified non-human animal ES cell of embodiment 331, wherein the transcriptional control element is a RAG1 transcriptional control element, a RAG2 transcriptional control element, a TCRα transcriptional control element, a TCRβ transcriptional control element, a TCRγ transcriptional control element and/or a TCRδ transcriptional control element.

In exemplary embodiment 334, provided herein is the genetically modified non-human animal ES cell of any one of embodiments 331 to 333, wherein a non-human animal derived from the ES cell expresses the exogenous TdT in DN thymocytes and/or DP thymocytes.

In exemplary embodiment 335, provided herein is the genetically modified non-human animal ES cell of any one of embodiments 331 to 334, wherein the nucleic acid sequence encoding the exogenous TdT is located at a RAG1 locus, a RAG2 locus, a TCRα chain locus, a TCRβ chain locus, a TCRγ chain locus and/or a TCRδ chain locus.

In exemplary embodiment 336, provided herein is the genetically modified non-human animal ES cell of any one of embodiments 331 to 335, wherein the nucleic acid sequence encoding the exogenous TdT is not operably linked to a constitutive transcriptional control element.

In exemplary embodiment 337, provided herein is the genetically modified non-human animal ES cell of any one of embodiments 331 to 336, wherein the exogenous TdT is not constitutively expressed in non-human animals derived from the ES cell.

In exemplary embodiment 338, provided herein is the genetically modified non-human animal ES cell of any one of embodiments 331 to 337, wherein the human immunoglobulin variable region gene segments are human light chain variable region gene segments.

In exemplary embodiment 339, provided herein is the genetically modified non-human animal ES cell of embodiment 338, wherein at least 10% of the V-J immunoglobulin light chain junctions in a non-human animal derived from the ES cell comprise non-template additions.

In exemplary embodiment 340, provided herein is the genetically modified non-human animal ES cell of embodiment 339, wherein at least 20% of the V-J immunoglobulin light chain junctions in the animal comprise non-template additions.

In exemplary embodiment 341, provided herein is the genetically modified non-human animal ES cell of embodiment 339, wherein at least 40% of the V-J immunoglobulin light chain junctions in the animal comprise non-template additions.

In exemplary embodiment 342, provided herein is the genetically modified non-human animal ES cell of any one of embodiments 338 to 341, wherein the human light chain variable region gene segments are κ gene segments.

In exemplary embodiment 343, provided herein is the genetically modified non-human animal ES cell of any one of embodiments 338 to 341, wherein the human light chain variable region gene segments are λ gene segments.

In exemplary embodiment 344, provided herein is the genetically modified non-human animal ES cell of any one of embodiments 331 to 337, wherein the human immunoglobulin variable region gene segments are human heavy chain variable region gene segments.

In exemplary embodiment 345, provided herein is the genetically modified non-human animal ES cell of any one of embodiments 331 to 343, wherein the TCR constant region gene is a TCRα constant region gene.

In exemplary embodiment 346, provided herein is the genetically modified non-human animal ES cell of embodiment 345, wherein the immunoglobulin variable region and the TCRα constant region gene are located at an endogenous TCRα locus.

In exemplary embodiment 347, provided herein is the genetically modified non-human animal ES cell of embodiment 344, wherein the TCR constant region gene is a TCRβ constant region gene.

In exemplary embodiment 348, provided herein is the genetically modified non-human animal ES cell of embodiment 347, wherein the immunoglobulin variable region and the TCRβ constant region gene are located at an endogenous TCRβ locus.

In exemplary embodiment 349, provided herein is the genetically modified non-human animal ES cell of any one of embodiments 331 to 344, wherein the TCR constant region gene is of endogenous species origin.

In exemplary embodiment 350, provided herein is the genetically modified non-human animal ES cell of any one of embodiments 331 to 348, wherein the TCR constant region gene is a mouse constant region gene.

In exemplary embodiment 351, provided herein is the genetically modified non-human animal ES cell of any one of embodiments 331 to 348, wherein the TCR constant region gene is a rat constant region gene.

In exemplary embodiment 352, provided herein is the genetically modified non-human animal ES cell of any one of embodiments 331 to 348, wherein the TCR constant region gene is a human constant region gene.

In exemplary embodiment 353, provided herein is the genetically modified non-human animal ES cell of any one of embodiments 331 to 352, wherein the immunoglobulin variable region comprises immunoglobulin variable region intergenic sequences of human origin.

In exemplary embodiment 354, provided herein is the genetically modified non-human animal ES cell of any one of embodiments 340 to 352, wherein the immunoglobulin variable region comprises immunoglobulin variable region intergenic sequences of endogenous species origin.

In exemplary embodiment 355, provided herein is the genetically modified non-human animal ES cell of any one of embodiments 341 to 352, wherein the immunoglobulin variable region comprises immunoglobulin variable region intergenic sequences of mouse origin.

In exemplary embodiment 356, provided herein is the genetically modified non-human animal ES cell of any one of embodiments 341 to 352, wherein the immunoglobulin variable region comprises immunoglobulin variable region intergenic sequences of rat origin.

In exemplary embodiment 357, provided herein is the genetically modified non-human animal ES cell of any one of embodiments 341 to 356, further comprising in its genome an inactivated endogenous immunoglobulin locus.

In exemplary embodiment 358, provided herein is the genetically modified non-human animal ES cell of embodiment 357, wherein the inactivated endogenous immunoglobulin locus is an endogenous immunoglobulin heavy chain locus.

In exemplary embodiment 359, provided herein is the genetically modified non-human animal ES cell of embodiment 358, wherein the endogenous immunoglobulin heavy chain locus is inactivated by deletion of at least part of the variable region of the endogenous heavy chain locus.

In exemplary embodiment 360, provided herein is the genetically modified non-human animal ES cell of embodiment 359, wherein the deletion of the at least part of the variable region comprises deletion of the J gene segments of the variable region.

In exemplary embodiment 361, provided herein is the genetically modified non-human animal ES cell of embodiment 358, wherein the endogenous immunoglobulin heavy chain locus is inactivated by deletion of at least part of the constant region of the endogenous heavy chain locus.

In exemplary embodiment 362, provided herein is the genetically modified non-human animal ES cell of embodiment 361, wherein the deletion of the at least part of the constant region comprises deletion of the Cμ gene of the constant region.

In exemplary embodiment 363, provided herein is the genetically modified non-human animal ES cell of embodiment 357, wherein the inactivated endogenous immunoglobulin locus is an endogenous immunoglobulin κ chain locus.

In exemplary embodiment 364, provided herein is the genetically modified non-human animal ES cell of embodiment 363, wherein the endogenous immunoglobulin κ chain locus is inactivated by deletion of at least part of the variable region of the endogenous κ chain locus.

In exemplary embodiment 365, provided herein is the genetically modified non-human animal ES cell of embodiment 364, wherein the deletion of the at least part of the variable region comprises deletion of the J gene segments of the variable region.

In exemplary embodiment 366, provided herein is the genetically modified non-human animal ES cell of embodiment 365, wherein the endogenous immunoglobulin κ locus is inactivated by deletion of at least part of the constant region of the endogenous κ chain locus.

In exemplary embodiment 367, provided herein is the genetically modified non-human animal ES cell of embodiment 366, wherein the deletion of the at least part of the constant region comprises deletion of the Cκ gene of the constant region.

In exemplary embodiment 368, provided herein is the genetically modified non-human animal ES cell of embodiment 357, wherein the inactivated endogenous immunoglobulin locus is an endogenous immunoglobulin λ chain locus.

In exemplary embodiment 369, provided herein is the genetically modified non-human animal ES cell of embodiment 368, wherein the endogenous immunoglobulin λ chain locus is inactivated by deletion of at least part of a V-J-C cluster of the endogenous λ chain locus.

In exemplary embodiment 370, provided herein is the genetically modified non-human animal ES cell of any one of embodiments 331 to 369, wherein the unrearranged human immunoglobulin variable region gene segments undergo rearrangement during T cell development to generate rearranged immunoglobulin variable region genes in the T cells of a non-human animal derived from the ES cell.

In exemplary embodiment 371, provided herein is the genetically modified non-human animal ES cell of embodiment 370, wherein at least 10% of the rearranged variable region genes in the non-human animal derived from the ES cell comprise non-template additions.

In exemplary embodiment 372, provided herein is the genetically modified non-human animal ES cell of embodiment 370, wherein at least 20% of the rearranged variable region genes in the non-human animal derived from the ES cell comprise non-template additions.

In exemplary embodiment 373, provided herein is the genetically modified non-human animal ES cell of embodiment 370, wherein at least 40% of the rearranged variable region genes in the non-human animal derived from the ES cell comprise non-template additions.

In exemplary embodiment 374, provided herein is the genetically modified non-human animal ES cell of any one of embodiments 370 to 372, wherein the non-human animal derived from the ES cell expresses chimeric antigen receptors comprising a variable domain encoded by the rearranged variable region gene and a constant domain encoded by the TCR constant region gene.

In exemplary embodiment 375, provided herein is the genetically modified ES cell of any one of embodiments 202 to 374, further comprising a functional ectopic mouse Adam6 gene.

In exemplary embodiment 376, provided herein is the genetically modified non-human animal ES cell of any one of embodiments 202 to 375, wherein the non-human animal is a mammal.

In exemplary embodiment 377, provided herein is the genetically modified non-human animal ES cell of embodiment 376, wherein the mammal is a rodent.

In exemplary embodiment 378, provided herein is the genetically modified non-human animal ES cell of embodiment 377, wherein the rodent is a rat or a mouse.

In exemplary embodiment 379, provided herein is the genetically modified non-human animal ES cell of embodiment 377, wherein the rodent is a mouse.

In exemplary embodiment 380, provided herein is the genetically modified non-human animal ES cell of embodiment 377, wherein the rodent is a rat.

In exemplary embodiment 381, provided herein is a method of making a genetically modified non-human animal comprising using the genetically modified non-human animal ES cell of any one of embodiments 202 to 380.

In exemplary embodiment 382, provided herein is a method of making a non-human animal comprising a genetic modification comprising engineering the non-human animal to comprise in its germline a nucleic acid sequence encoding human Terminal Deoxynucleotidyltransferase (hTdT).

In exemplary embodiment 383, provided herein is a method of making a non-human animal comprising a genetic modification comprising engineering the non-human animal to comprise in its germline: a nucleic acid sequence encoding an exogenous Terminal Deoxynucleotidyltransferase (TdT); and an immunoglobulin variable region comprising unrearranged human immunoglobulin variable region gene segments operably linked to an immunoglobulin constant region gene.

In exemplary embodiment 385, provided herein is a method of making a non-human animal comprising a genetic modification comprising engineering the non-human animal to comprise in its germline: a nucleic acid sequence encoding an exogenous Terminal Deoxynucleotidyltransferase (TdT); and a T cell receptor (TCR) variable region comprising unrearranged human TCR variable region gene segments operably linked to a TCR constant region gene.

In exemplary embodiment 386, provided herein is a method of making a non-human animal comprising a genetic modification comprising engineering the non-human animal to comprise in its germline: a nucleic acid sequence encoding an exogenous Terminal Deoxynucleotidyltransferase (TdT); and an immunoglobulin variable region comprising unrearranged human immunoglobulin variable region gene segments operably linked to a TCR constant region gene.

In exemplary embodiment 387, provided herein is the method of any one of embodiments 382 to 385, wherein the non-human animal is a mammal.

In exemplary embodiment 388, provided herein is the method of embodiment 386, wherein the mammal is a rodent.

In exemplary embodiment 389, provided herein is the method of embodiment 387, wherein the rodent is a rat or a mouse.

In exemplary embodiment 390, provided herein is the method of embodiment 387, wherein the rodent is a mouse.

EXAMPLES

The invention will be further illustrated by the following nonlimiting examples. These Examples are set forth to aid in the understanding of the invention but are not intended to, and should not be construed to, limit its scope in any way. The Examples do not include detailed descriptions of conventional methods that would be well known to those of ordinary skill in the art (molecular cloning techniques, etc.). Unless indicated otherwise, parts are parts by weight, molecular weight is average molecular weight, temperature is indicated in Celsius, and pressure is at or near atmospheric.

Example 1: Generation of Mice Expressing Human TdT

Mice comprising a human TdT gene, either as random transgene or targeted to the immunoglobulin kappa locus, are made using VELOCIGENE® genetic engineering technology (see, e.g., U.S. Pat. No. 6,586,251 and Valenzuela, D. M., et al. (2003) High-throughput engineering of the mouse genome coupled with high-resolution expression analysis. Nat. Biotech. 21(6): 652-659), wherein human sequences derived from BAC libraries using bacterial homologous recombination are used to make large targeting vectors (LTVECs) comprising genomic fragments of human TdT locus and, in the case of TdT targeted to the IgK locus, flanked by targeting arms to target the LTVECs to the IgK locus in mouse ES cells. LTVECs are linearized and electroporated into a mouse ES cell line according to Valenzuela et al. ES cells are screened by TAQMAN® to determine either gene copy number (for randomly integrated transgenes) or correct targeting to the IgK locus.

Alternatively, a short isoform human TdT (TdTS) cDNA is synthesized de novo (Blue Heron Bio) and incorporated into a targeting for introduction into ES cells as described above.

Targeted ES cell clones are introduced into 8-cell stage (or earlier) mouse embryos by the VELOCIMOUSE® method (Poueymirou, W. T. et al. (2007). F0 generation mice fully derived from gene-targeted embryonic stem cells allowing immediate phenotypic analyses. Nat. Biotech. 25: 91-99). VELOCIMMUNE® (F0 mice fully derived from the donor ES cell) bearing human TdT locus are identified by screening by TAQMAN® in a gain of human allele assay (Valenzuela et al.). F0 pups are genotyped and bred to homozygosity. Mice homozygous for human TdT locus are made and phenotyped. As specifically described in Example 1 below, mice comprising human TdTS and unrearranged human variable light and heavy chain loci are generated by introducing human TdTS random transgene or targeting human TdTS to IgK locus in VELOCIMMUNE® mice comprising a functional ectopic mouse Adam6 gene. However, at least for the randomly introduced human TdTS transgene, such animals can also be generated by first generating ES cells comprising a human TdTS as described below, generating mice therefrom, and breeding mice comprising randomly integrated human TdTS locus with VELOCIMMUNE® mice comprising a functional ectopic mouse Adam6 gene.

Example 1.1. Generation of Trans Gene Expressing Short Isoform of Human TdT (TdTS) Under Control of Mouse Rag Regulatory Elements (Rag-TdT Tg)

Briefly, a large targeting vector (LTVEC), shown in detail in FIG. 1, was constructed from mouse and human BAC clones in which the mouse Rag2 gene (from the ATG start codon in exon 3 to the TGA stop codon in exon 3 was replaced with the human Terminal deoxynucleotidyl Transferase (TdT or DNTT) gene encoding only the short isoform, TdTS (from the ATG start codon in exon 1 to ~0.5 kb 3' of the polyA signal in exon 13). The RNA splice sites of TdT exons 7 and 12 were mutated to prevent expression of the long isoforms (TdTL1 and L2). In the same LTVEC, the mouse Rag1 gene from the ATG start codon in exon 2 to the TAA stop codon in exon 2 was replaced with the coding sequence of the enhanced green fluorescent protein (EGFP) and the LacZ 3'UTR-polyA signal. The LTVEC contains 130 kb of upstream regulatory sequences 5' of the mouse Rag2 gene and 8.8 kb of upstream regulatory sequences 3' of the mouse Rag1 gene, as well as the 5.6 kb Rag2-Rag1 intergenic region.

The LTVEC was constructed from mouse BAC clone RP23-374f10 (Invitrogen/Life Technologies) containing the Rag2 and Rag1 genes, and human BAC clone RP11-1070o2 (Invitrogen/Life Technologies) containing the TdT gene using standard molecular biology and recombineering techniques such as PCR, restriction digestion/ligation, Gibson Isothermal Assembly, CRISPR/Cas9, bacterial homologous recombination, etc. The final LTVEC contains, from 5' to 3': (1) a Loxp-pgkp-em7-neo-loxp cassette for selection in ES cells or bacteria, (2) 134,069 bp of mouse genomic sequence beginning 129,440 bp upstream of Rag2 exon 1 and ending 25 bp from the start of Rag2 exon 3 (mouse genome coordinates 2:101,495,278-101,629,347 based on GRCm38 assembly), (3) 34,573 bp of human TdT genomic sequence beginning at the ATG start codon in exon 1 and ending 514 bp 3' of the polyA signal (human genome coordinates 10:96,304,498-96,339,063 based on GRCh38 assembly); within the human TdT gene, the splice donor site of exon 7 is deleted and replaced by a NotI site to prevent expression of the TdTL2 isoform, and the splice acceptor site of exon 12 is deleted to prevent expression of the TdTL1 isoform (detailed description below), (4) AsiSI site; (5) 10,742 bp of mouse genomic sequence (GRCm38 genome coordinates 2:101,630,931-101,641,672) containing the 3'UTR of Rag2 exon 3 (1599 bp), the 5753 bp Rag2/Rag1 intergenic region, and the 3'UTR of Rag1 exon 2 (3390 bp), (6) FseI site, (7) 1,068 bp on the minus strand containing the 249 bp polyA signal of LacZ and the 793 bp CDS of EGFP, (8) 13,459 bp of mouse genomic sequence (GRCm38 coordinates 2:101, 644,793-101,658,251) with Rag1 on the minus strand, beginning at the ATG start codon in Rag1 exon 2 and ending 8,750 bp 3' of the transcription start site of Rag1, and (9) Em7-CM cassette for selection in bacteria (see FIG. 1).

In detail, the cloning steps to create two modifications of the TdT gene to prevent alternative splicing using TdT exons 7 and 12 (which are used to make the long isoforms TdTL2 and TdTL1, respectively) while still allowing splicing of the transcript encoding the short isoform TdTS were constructed from BAC clone RP11-1070o2 using BHR and ligation:

(1) 13 bp including the splice donor site of exon 7 (GTCGGGTCGTGGT (SEQ ID NO:1), splice donor underlined) were deleted and replaced by a NotI site (GCGGCCGC (SEQ ID NO:2)). This created an overlapping SacII site (CCGCGG (SEQ ID NO:3)), and (2) The 2 bp splice acceptor site of exon 12 was deleted.

The final LTVEC is depicted in FIG. 1, with the approximate positions of various sequence junctions indicated in the figure. The junctions are also summarized in Table 1 below.

TABLE 1

Sequence Junctions of Rag-TdT Tg LTVEC

| Junction | SEQ ID NO | Sequence |
|---|---|---|
| 1 (mouse Rag2/ human TdT) | 4 | TATTGCGTTTTTTTAATCCTTTCAGATAAAAGACCTA TTCACAATCAAAA/ATGGATCCACCACGAGCGTCCC ACTTGAGCCCTCGGAAGAAGAGACCCC |
| 2 (human TdT/ AsiSI/ mouse Rag2) | 5 | GCCCTGGCTGAGGGAAATTTTGGAACTCCCAGGC TCCAGACCCATTCTTT/GCGATCGC/TTTAGCAAA AGCCCCTCAGACTCAGGTATATTGCTCTCT GAATCTACTTT |
| 3 (mouse Rag1/Fse I/EGFP) | 6 | CCAAAGGAAAACACATTGGCAAATACCAACTTCTATG TGGAGATCCTAT/GGCCGGCC/ GGGGATCCAGACATGA TAAGATACATTGATGAGTTTGGACAAACCACAAC |
| 4 (EGFP/ mouse Rag1) | 7 | TCGACCAGGATGGGCACCACCCCGGTGAACAGCTC CTCGCCCTTGCTCAC/CATGTTGGCTAAGC TACCTGGGAACAATGGGGGGGGGGGGGGA GTCAAG |

The final LTVEC was linearized and electroporated into VELOCIMMUNE® ES cells that comprise a functional ectopic mouse Adam6 gene (see, e.g., U.S. Pat. No. 8,642, 835, incorporated herein by reference). After selection with Neo, ES cells were screened by TAQMAN® to determine copy number of the transgene. ES cells comprising a single copy, two copies, or multiple copies of the human Rag-TdT transgene were obtained.

The integration site of the Rag-TdT transgene is determined via methods known in the art. In one embodiment, the integration site is determined using low coverage paired-end sequencing of the whole mouse genome (Sequencing library—Nextera DNA Library Preparation, Illumina; Sequence—Miseq, Illumina). For example, in one instance it was determined that Rag-TdT transgene integrated as two tandem head to tail copies between coordinates 41130492 and 41130502 on chromosome 1 (coordinates in GRCm38/mm10 Assembly), without disrupting any coding regions.

Example 1.2. Generation of Targeted Immunoglobulin Kappa Locus Insertion of Short Isoform of Human TdT (TdTS) Under Control of Mouse Rag Regulatory Elements (Rag-TdT IgK)

In order to generate a mouse comprising human TdT under control of the Rag regulatory elements on the mouse immunoglobulin kappa locus, mouse IgK homology arms for recombination in ES cells were added to the 5' and 3' ends of the construct that is generated as described in Example 1.1 and FIG. 1. In general, the mouse IgK arms are added by: (1) modifying the mouse IgK BAC to by bacterial homologous recombination to insert a selection cassette (e.g., Hyg, Neo, etc.) flanked by I-CeuI and PI-SceI restriction enzyme sites, and (2) inserting the TdT construct into the mouse IgK BAC by I-CeuI and PI-SceI ligation. The final LTVEC depicted in FIG. 2.

This final LTVEC contains, from 5' to 3': (1) a Spec cassette for selection in bacteria, (2) a 28591 bp 5' mouse homology arm (GRCm38 genome coordinates 6:70,725,823-70,754,415) containing the IgKc gene, the IgK 3' enhancer, and the 3' IgK recombining sequence (RS); the mouse arm ends ~2.6 kb 3' of the RS, (3) PI-SceI site, (4) a loxp-UbCp-em7-hyg-loxp cassette for selection in ES cells or bacteria, (5) the construct described above in Example 1.1 and FIG. 1 containing the Rag2 promoter-human TdTS and Rag1-EGFP genes, (6) I-CeuI site, (7) a 44,900 bp 3' mouse IgK homology arm (GRCm38 genome coordinates 6:70,754,508-70,799,678), and (8) CM cassette for selection in bacteria.

Figure 2:
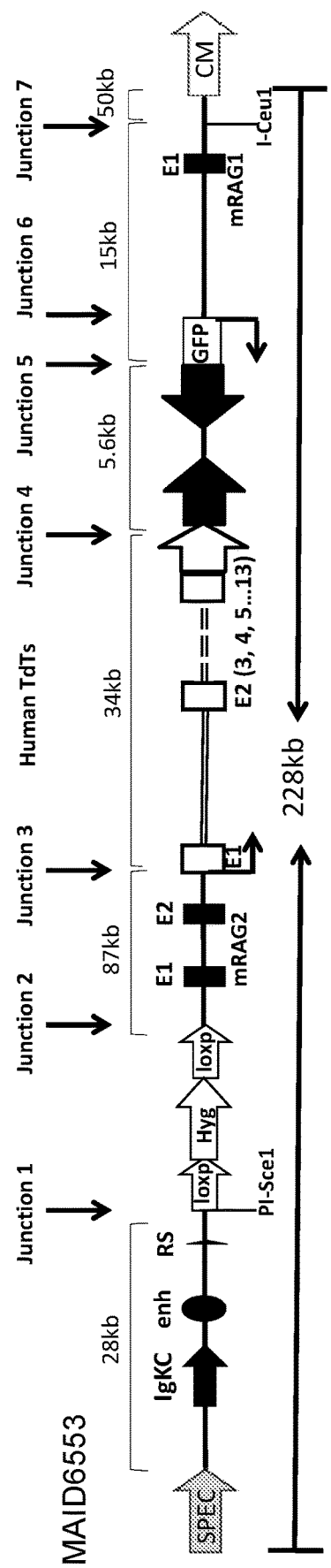
FIG. 2 depicts a diagram of an exemplary targeting vector (not to scale) where a part of the mouse Rag2 gene is replaced with a DNA sequence encoding short isoform human TdT (hTdTs). In the depicted embodiment, the vector is used to insert hTdT, driven by the mouse RAG2 promoter, into the Ig kappa locus. Unless labeling in the diagram suggests otherwise (e.g., as for selection cassettes, loxP sites, etc.), filled shapes and single lines represent mouse sequences, and empty shapes and double lines represent human sequences. E1, E2, etc. represent exons of particular illustrated genes, GFP is green fluorescent protein, CM is chloramphenicol resistant gene, hyg is hygromycin resistant gene. Junctions 1-7 correspond to junctions in Table 2.

The final LTVEC is depicted in FIG. 2, with the approximate positions of various sequence junctions indicated in the figure. The junctions are also summarized in Table 2 below.

TABLE 2

Sequence Junctions of Rag-TdT IgK LTVEC

| Junction | SEQ ID NO | Sequence |
|---|---|---|
| 1. (mouse IgK/PI-SceI/ loxp-Ub-Hyg cassette) | 8 | CATCCTTACATCTTTGTCATCCCCTGTATCAACA TGGAAAGGCATTAATG/ATCTATGTCGGGTGCGG AGAAAGAGGTAATGAAATGGCA/ACCGGTATAA CTTCGTATAATGTATGCTATACGAAGTTATATG CATGGCC |
| 2. (loxp-Ub-Hyg cassette/ mouse Rag2) | 9 | TTCGTATAATGTATGCTATACGAAGTTATGTC GACCTCGAGGGGGGGCCC/ACCTCCAGC TGCCTTACAGAAAAGCAAATGCTTGCTTGCA ACAATCACCT |
| 3. (mouse Rag2/human TdTS) | 10 | TATTGCGTTTTTTTAATCCTTTCAGATAAAA GACCTATTCACAATCAAAA/ATGGATCCACC ACGAGCGTCCCACTTGAGCCCTCGGAAGAA GAGACCCC |

TABLE 2-continued

Sequence Junctions of Rag-TdT IgK LTVEC

| Junction | SEQ ID NO | Sequence |
|---|---|---|
| 4. (human TdTS/AsiSI/ mouse Rag2) | 11 | GCCCTGGCTGAGGGAAATTTTGGAACTCCCAG GCTCCAGACCCATTCTTT/GCGATCGC/TTTAG CAAAAGCCCCTCAGACTCAGGTATATTGCTCT CTGAATCTACTTT |
| 5. (mouse Rag1/FseI/ EGFP) | 12 | CCCAAAGGAAAACACATTGGCAAATACCAA CTTCTATGTGGAGATCCTAT/GGCCGGCC/GG GGATCCAGACATGATAAGATACATTGATGAG TTTGGACAAACCACAAC |
| 6. (EGFP/ mouse Rag1) | 13 | TCGACCAGGATGGGCACCACCCCGGTGAACA GCTCCTCGCCCTTGCTCAC/CATGTTGGCTAA GCTACCTGGGAACAATGGGGGGGGGGGGGG AGTCAAG |
| 7. (mouse Rag1/I-CeuI/ mouse IgK) | 14 | ACCTCTGCTGTGTCTGCAAGTTTGGCTTGTTC CTGCTTCTGATTTTTGGG/TCTAGACCCCCGGG CTCGATAACTATAACGGTCCTAAGGTAGCGA CTCGAG/CATAACCACTTTCCTGCTATGGATCT GTTAAATATCCGCCAAAGGCCAAG |

The resulting LTVEC was linearized and electroporated into VELOCIMMUNE® ES cells that comprise a functional ectopic mouse Adam6 gene (see, e.g., U.S. Pat. No. 8,642,835, incorporated herein by reference). After selection for Hyg-resistance, ES cells were screened by TAQMAN® modification of allele assay (Valenzuela et al, supra) to identify correctly targeted clones.

Example 1.3. Generation of Random Transgenic and Targeted Immunoglobulin Kappa Locus Insertion of Short Isoform of Human TdT (TdTS), Both Under Control of Mouse Immunoglobulin Heavy Chain Intronic Enhancer (Eµ) and Mouse IgV$_H$1-72 Promoter (mIgH-Eµ-V$_H$1-72-TdT tg and mIgH-Eµ-V$_H$1-72-TdT IgK, Respectively)

The same human TdTS gene as used to make the Rag-TdT in Examples 1.1 and 1.2 (i.e., from ATG start codon to about 514 bp 3' of the polyA signal), was placed under the control of the 689 bp mouse Eµ enhancer and 303 bp mouse IgV$_H$1-72 promoter. This construct was either randomly integrated into the mouse genome or targeted to the immunoglobulin K (IgK) locus. For targeted integration, the gene was inserted between the same 5' and 3' mouse IgK homology arms as were used to make the LTVEC in Example 1.2.

Specifically, the final LTVEC contains, from 5' to 3' (FIG. 3): (1) a Spec cassette for selection in bacteria, (2) a 28591 bp 5' mouse homology arm (GRCm38 genome coordinates 6:70,725,823-70,754,415) containing the IgK constant (IgKC) gene, the IgK 3' enhancer, and the 3' IgK recombining sequence (RS); the mouse arm ends ~2.6 kb 3' of the RS, (3) I-CeuI site, (4) loxp-UbCp-em7-hyg-loxp cassette in reverse orientation for selection in ES cells or bacteria, (5) the same 34,573 bp human TdTS gene used in Examples above in reverse orientation, (6) the 303 bp mouse IgHV1-72 promoter in reverse orientation (GRCm38 genome coordinates 12:115,758,417-115,758,719), (7) The 689 bp mouse Eµ enhancer (EcoRI-XbaI fragment, GRCm38 genome coordinates 12:113,427,284-113,427,972) in reverse orientation, (8) PI-SceI site, (9) a 44,900 bp 3' mouse IgK homology arm (GRCm38 genome coordinates 6:70,754,508-70,799,678), and (10) CM cassette for selection in bacteria.

Figure 3:
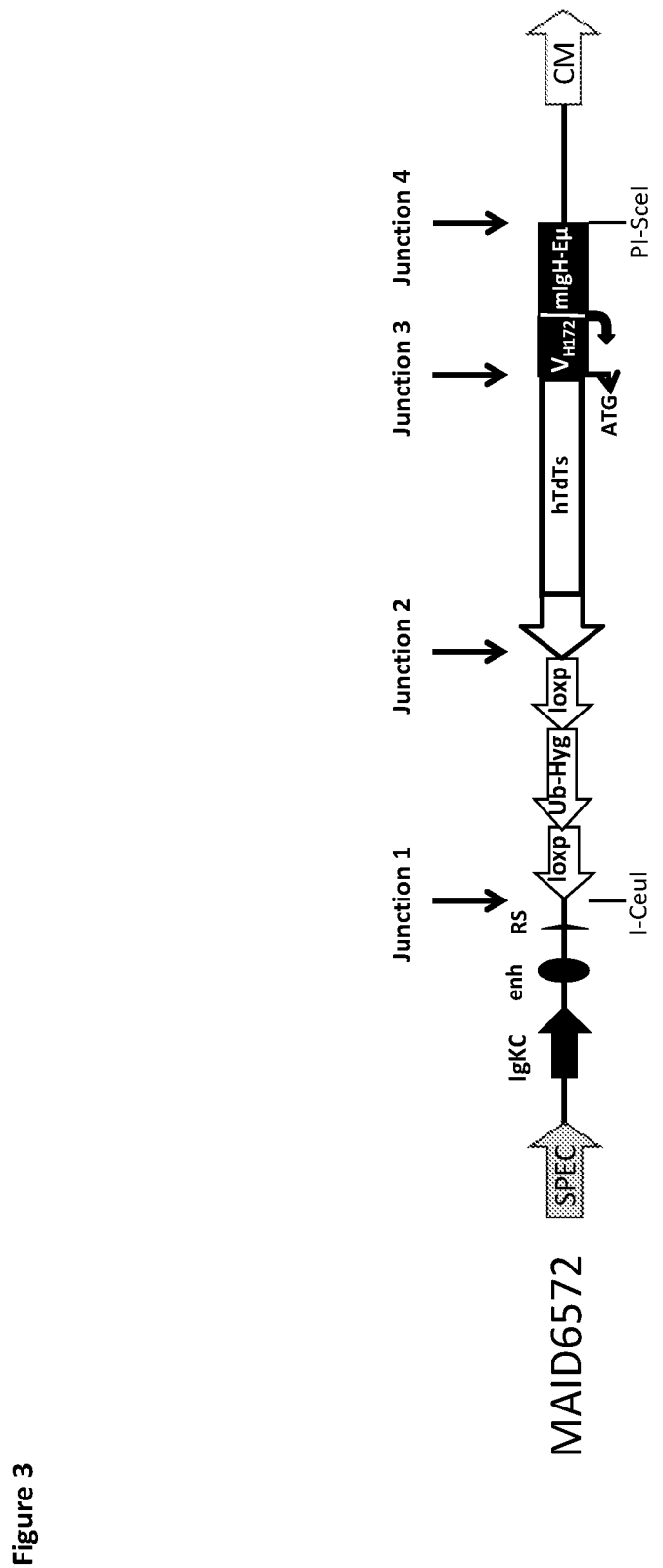
FIG. 3 depicts a diagram of an exemplary targeting vector (not to scale) used to insert a DNA sequence encoding human TdT (hTdTs), driven by $V_H1-72$ promoter and Eμ enhancer, into the immunoglobulin κ locus. Unless labeling in the diagram suggests otherwise (e.g., as for selection cassettes, loxP sites, etc.), filled shapes and single lines represent mouse sequences, and empty shapes and double lines represent human sequences. E1, E2, etc. represent exons of particular illustrated genes, GFP is green fluorescent protein, CM is chloramphenicol resistant gene, hyg is hygromycin resistant gene. Junctions 1-4 correspond to junctions in Table 3.

The approximate positions of the specific sequence junctions in the final vector are depicted in FIG. 3, and their sequences indicated in Table 3 below.

TABLE 3

Sequence Junctions of mIgH-Eµ-V$_H$1-72-TdT IgK LTVEC

| Junction | SEQ ID NO | Sequence |
|---|---|---|
| 1. (mouse/ICeuI/loxp-Ub-Hyg cassette) | 15 | CATCCTTACATCTTTGTCATCCCCTGTAT CAACATGGAAAGGCATTAATG/TCGCTA CCTTAGGACCGTTATAGTTA/GGCCCCCCCTCGA GGTCGACATAACTTCGTATAGCATACATTATACGAAG |
| 2. (loxp-Ub-Hyg cassette/human TdT) | 16 | GGCCATGCATATAACTTCGTATAGCAT ACATTATACGAAGTTATACCGGT/AAA GAATGGGTCTGGAGCCTGGGAGTTCCA AAATTTCCCTCAGCCAGGGC |
| 3. (human TdT/mouse IgHV1-72) | 17 | CGGGGTCTCTTCTTCCGAGGGCTCAAGT GGGACGCTCGTGGTGGATCCAT/GGTGAG GTCCTGTGTGCTCAGTAACTGTAAAGAGA ACAGTGATCTCATGT |
| 4. (mouse Eµ/PI-SceI/mouse IgK) | 18 | TAGTTTCCCCAAACTTAAGTTTATCGACTTCTA AAATGTATTTAGAATTC/TGCCATTTCATTACC TCTTTCTCCGCACCCGACATAGATAAAGCTT/CA TAACCACTTTCCTGCTATGGATCTGTTAAATAT CCGCCAAAGGCCAAG |

The resulting LTVEC was linearized and electroporated into VELOCIMMUNE® ES cells that comprise a functional ectopic mouse Adam6 gene (see, e.g., U.S. Pat. No. 8,642, 835, incorporated herein by reference). After selection for Hyg-resistance, ES cell clones were screened by TAQMAN® for correct targeting to the mouse IgK locus (for mIgH-Eµ-V$_H$1-72-TdT IgK) or for transgene copy number (for tg).

Example 1.4. Generation of Targeted Immunoglobulin Kappa Locus Insertion as Well as Transgenic Human TdTS from TdTS cDNA Alternatively, a TdTS cDNA is synthesized de novo (Blue Heron Bio) as a 3682 bp DNA fragment and incorporated into a targeting vector for introduction into ES cells. The targeting vector contains, from 5' to 3', a PI-SceI site, the 689 bp mouse IgH intronic enhancer (EcoRI-XbaI fragment), the 303 bp mouse VH1-72 promoter, the 1530 bp CDS of human TdTS (NCBI RefSeq NM_004088) with the 735 bp intron 2 retained between exons 2 and 3 for intron-mediated enhancement of expression, the 340 bp human TdT 3' UTR/polyA signal, NotI and SalI restriction enzyme sites for ligating in a loxp-neo-loxp cassette, and an I-CeuI site. The vector was inserted between the same 5' and 3' mouse IgK homology arms as were used to make the LTVEC in Example 1.2 and either targeted to the IgK locus or randomly integrated into the mouse genome.

The resulting LTVEC is linearized and electroporated into VELOCIMMUNE® ES cells that comprise a functional ectopic mouse Adam6 gene (see, e.g., U.S. Pat. No. 8,642, 835, incorporated herein by reference). After selection for Hyg-resistance, ES cell clones are screened by TAQMAN® for correct targeting to the mouse IgK locus (for IgK targeted version) or for transgene copy number (for transgenic version).

Example 1.5. Mice Expressing Human TdTS

As described above, once correctly targeted ES cells are produced, they are introduced into 8-cell stage (or earlier) mouse embryos by the VELOCIMOUSE® method, screened in a gain of allele assay, and subsequently bred to homozygosity. Heterozygous or homozygous animals express human TdTS as well as antibodies comprising human variable light and heavy chain domains and mouse constant regions (as these mice comprise human immunoglobulin variable light and heavy gene segments at the endogenous IgK and IgH loci, respectively: VELOCIMMUNE® mice).

Several versions of human TdTS mice were generated and tested, and those included random transgenic and IgK targeted TdTS both under the control of Rag promoter and Eµ-V$_H$1-72 regulatory elements. Also included were versions with one, two, or several copies of the TdTS transgene; as well as versions generated from genomic TdT and cDNA TdT sequences. The remaining examples demonstrate data obtained with mice comprising a transgene of Rag-genomic TdT (tandem insertion of two copies on chromosome 1, as described in Example 1.1 above) and Eµ-V$_H$1-72-genomic TdT targeted to the IgK locus (Example 1.3).

Figure 4:
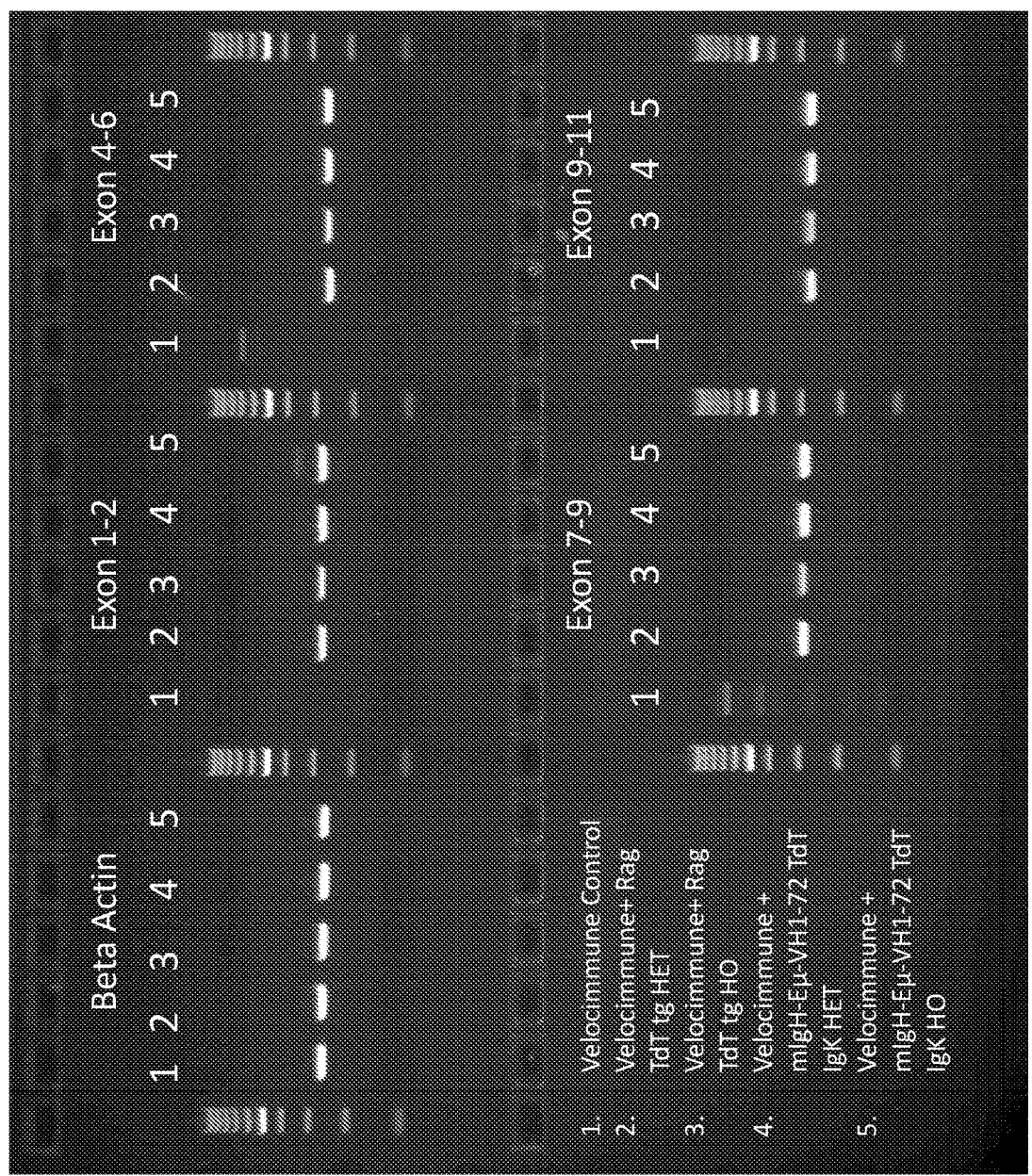
FIG. 4 depicts expression of hTdT mRNA in lymphocytes of VELOCIMMUNE® TdT mice compared to VELOCIMMUNE® control mice. VELOCIMMUNE® mice herein are mice that comprise a diverse repertoire of unrearranged human heavy chain and kappa light chain variable (V(D)J) gene segments. Het indicates a heterozygous mouse, HO indicates a homozygous mouse.

First, mice are tested for expression of TdT. PT-PCR was used for amplify TdT transcripts from bone marrow of either VELOCIMMUNE® control, VELOCIMMUNE®+Rag-genomic TdTS transgene, or VELOCIMMUNE®+Eµ-V$_H$1-72-genomic TdTS targeted to the IgK locus mice. Total RNA was used for reverse transcription by SUPESCRIPT® III Reverse Transcriptase (Life Technologies) using Oligo-dT primer. PCR was conducted using SsoAdvanced™ Universal SYBR® Green Supermix, with primers for either Beta Actin (control), primers designed to amplify exons 1-2, primers designed to amplify exons 4-6, primers designed to amplify exons 7-9, and primers designed to amplify exons 9-11. As shown in FIG. 4, presence of human TdT exons was detected in both versions of the mice, while absent from VELOCIMMUNE® control mice.

Example 2. Human Immunoglobulin Kappa Junctional Diversity in Mice Comprising Human TdTS To assess immunoglobulin repertoire sequence diversity in various VELOCIMMUNE® human TdTS mouse models described above in Example 1, IgK sequences were amplified by 5' RACE from spleens of various mice with mIgK constant primer and sequenced using Illumina MiSeq.

Specifically, splenic B cells were positively enriched from total splenocytes by magnetic cell sorting using anti-CD19 (mouse) magnetic beads and MACS® columns (Miltenyi Biotech). Total RNA was isolated from the purified splenic B cells using an RNeasy Plus RNA isolation kit (Qiagen) according to manufacturer's instructions. Reverse transcription was performed to generate cDNA containing Igκ constant region sequence, using a SMARTer™ RACE cDNA Amplification Kit (Clontech) and an Igκ specific primer (Table 4). During this process, a DNA sequence, which is reverse compliment to 3' of primer PE2-PIIA, was attached to the 3' end of the newly synthesized cDNAs. Purified Igκ specific cDNAs were then amplified by the 1st round PCR using the PE2-PIIA primer and an Igκ constant specific primer listed in Table 4. PCR products between 450-700 bp were isolated using Pippin Prep (SAGE Science). These products were further amplified by a 2nd round PCR using primers listed in Table 4 ("XXXXXX" represents a 6 bp index sequences to enable multiplexing samples for sequencing). PCR products between 400 bp-700 bp were isolated, purified, and quantified by qPCR using a KAPA Library Quantification Kit (KAPA Biosystems) before loading onto a Miseq sequencer (Illumina) for sequencing using Miseq Reagent Kits v3 (600 cycles).

TABLE 4

Primers used in library preparation for Igk repertoire sequencing

| RT primers | IgK (SEQ ID NO: 19) | 5'-AAGAAGCACACGACTGAGGCAC-3' |
|---|---|---|
| 1st round PCR primers | IgK Constant (SEQ ID NO: 20) | 5'-ACACTCTTTCCCTACACGACGCTCTTCCGATCT GGAAGATGGATACAGTTGGTGC-3' |
| | PE2-PIIA (SEQ ID NO: 21) | 5'-GTGACTGGAGTTCAGACGTGTGCTCTTCCGATCT AAGCAGTGGTATCAACGCAGAGT-3' |
| 2nd round PCR Primers | Forward (SEQ ID NO: 22) | 5'-AATGATACGGCGACCACCGAGATCTACACXXXX XX ACACTCTTTCCCTACACGACGCTCTTCCGATCT-3' |
| | Reverse (SEQ ID NO: 23) | 5'-CAAGCAGAAGACGGCATACGAGATXXXXXX GTGACTGGAGTTCAGACGTGTGCTCTTCCGATCT-3' |

For bioinformatics analysis, raw Illumina sequences were de-muliplexed and filtered based on quality, length and perfect match to kappa constant region primer. Overlapping paired-end reads were merged and analyzed using custom in-house pipeline. The pipeline used local installation of IgBLAST (NCBI, v2.2.25+) to align rearranged light chain sequences to human germline V and J gene database. Rearrangements were considered productive if no stop codons were detected and VJ junction was in-frame with J segment. Otherwise rearrangements were considered nonproductive and excluded from analysis.

CDR3 sequences were extracted using International Immunogenetics Information System (IMGT) boundaries. Junctional region between annotated V and J segments was classified as P and N nucleotides. Region with N/P additions was extracted from each sequence and its length calculated. Diversity of antibody repertoire was calculated by analyzing unique clonotypes. Sequence diversity was defined as a number of unique CDR3 sequences in randomly chosen 10,000 reads.

Figure 5:
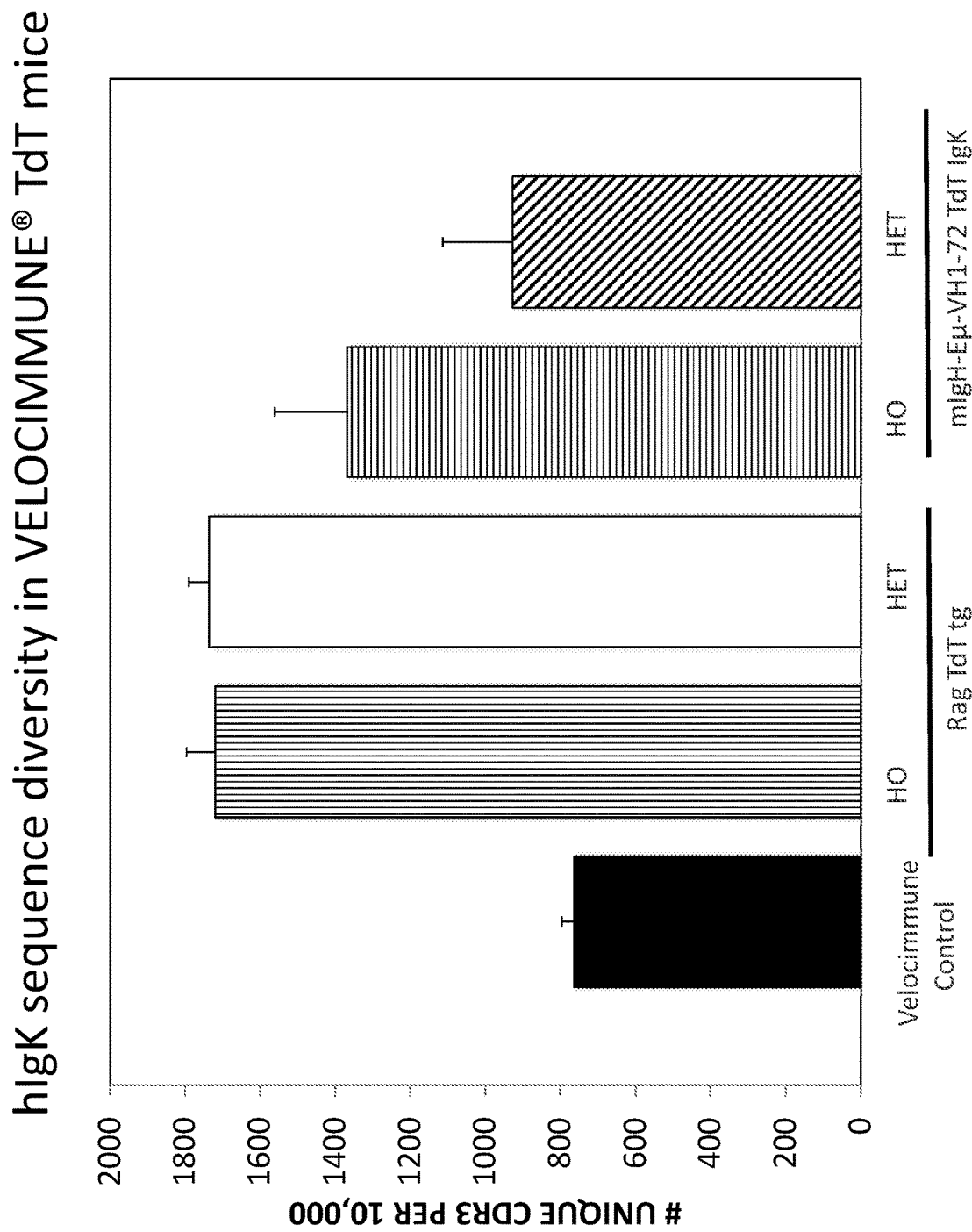
FIG. 5 depicts a graph showing hIgκ sequence diversity (# of unique light chain CDR3 sequences per 10,000 hIgκ sequencing reads) in VELOCIMMUNE® mice expressing hTdT compared to VELOCIMMUNE® control mice. Het indicates a heterozygous mouse, HO indicates a homozygous mouse.

FIG. 5 shows that up to 2-fold increase in the number of unique CDR3 amino acid sequences was detected in human TdTS mouse models compared with VELOCIMMUNE® mice that did not comprise human TdTS. Increased CDR3 diversity was also observed on the nucleotide level (data not shown). FIG. 5 only shows data obtained with mice comprising two copies of transgene of Rag-genomic TdTS (Rag TdT Tg) and Eμ-$V_{H}$1-72-genomic TdTS targeted to the IgK locus (mIgH-Eμ-$V_{H}$1-72 TdT IgK) (both homozygous and heterozygous versions), while similar data was obtained from other versions of the mice (not shown).

Example 3. Increase in Non-Germline Additions in Mice Comprising Human TdTS

Percentage of non-germline nucleotide additions in CDR3 (which consists of parts of both Vκ and Jκ gene segments) was also determined from Next Generation Sequencing described in Example 2 above.

Figure 6:
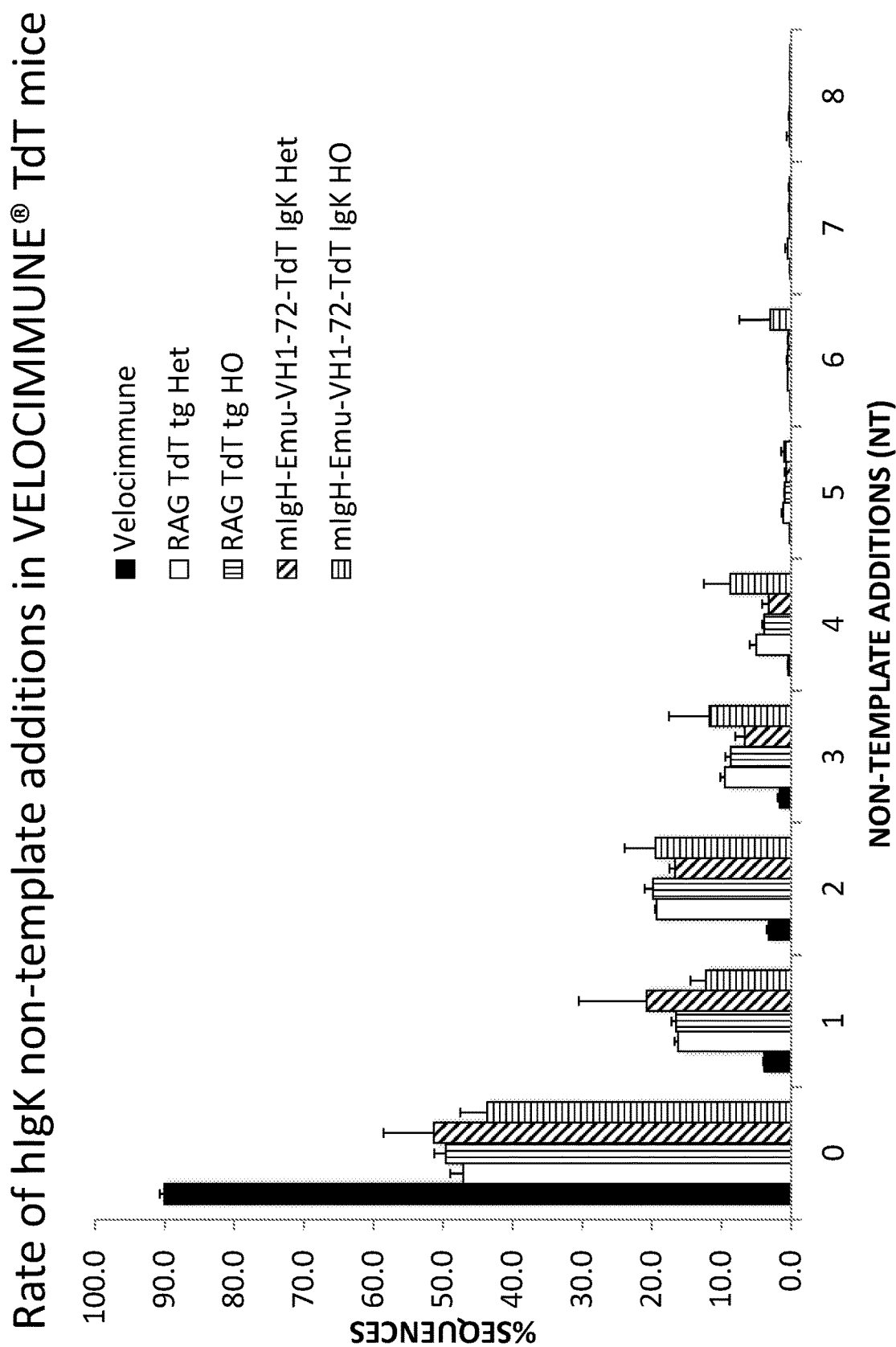
FIG. 6 depicts a graph showing the distribution of hIgκ non-template additions in VELOCIMMUNE® mice expressing hTdT compared to VELOCIMMUNE® control mice. Het indicates a heterozygous mouse, HO indicates a homozygous mouse. "NT" stands for nucleotides.

As depicted in FIG. 6, about 45% of humanized kappa light chain in B cells were shown to have non-germline additions in both versions of humanized TdTS mice as compared to about 10% in VELOCIMMUNE® mice that comprise a functional ectopic mouse Adam6 gene. Sequence analysis of immunoglobulin light chains from spleen showed 0 to 8 non-template additions in light chains of human TdTS mice (8 in the figure includes sequences with 8 or more non-template additions).

Example 4. Human Light Chain CDR3 Lengths in Immunoglobulins Obtained from Human TdTS Mice CDR3 sequences were extracted using International Immunogenetics Information System (IMGT) boundaries. Non-template nucleotides were determined based on known light chain V and J sequences.

Figure 7:
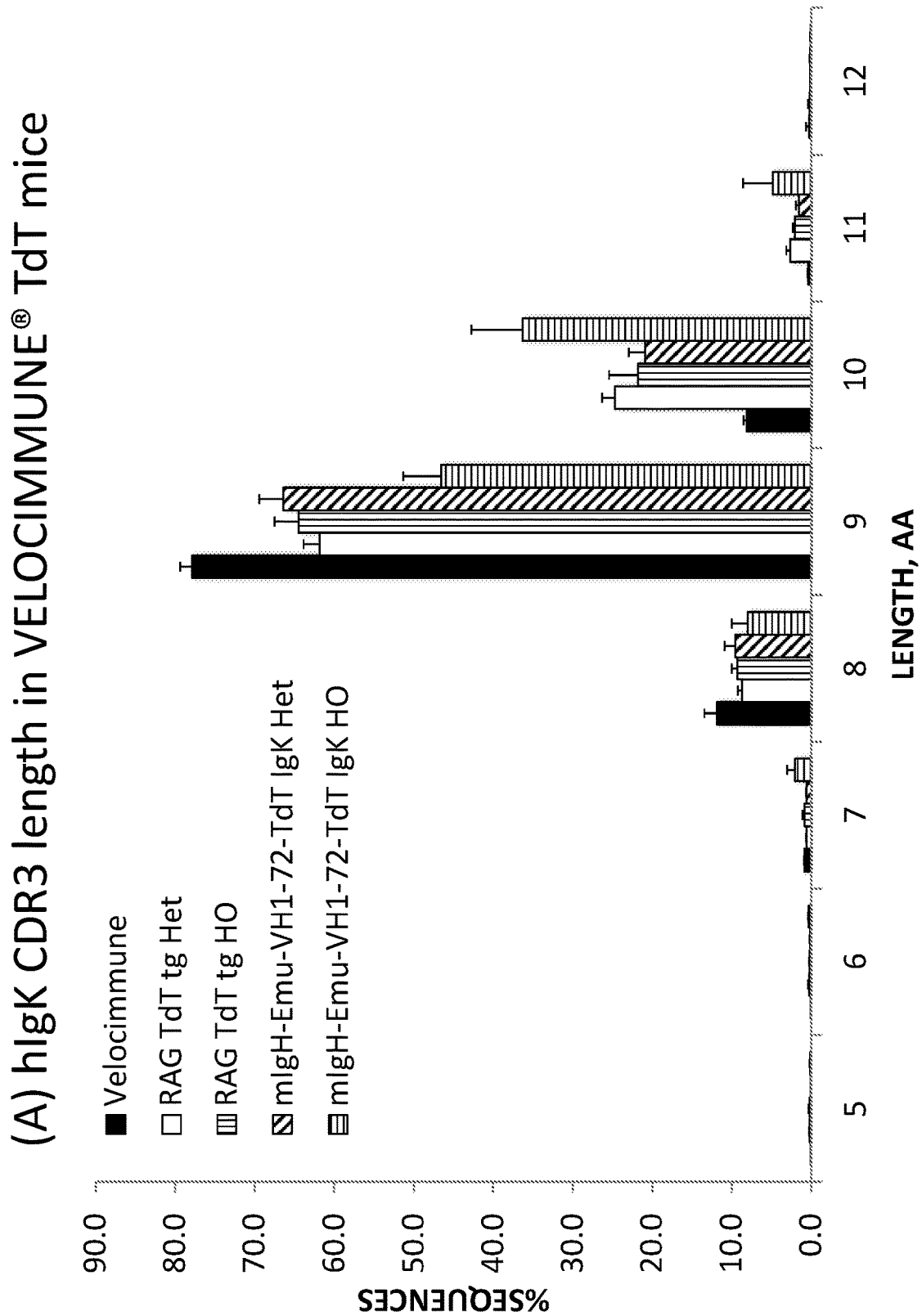
FIG. 7 has two panels. Panel (A) depicts a graph showing the distribution of hIgκ CDR3 lengths in VELOCIMMUNE® mice expressing hTdT compared to VELOCIMMUNE® control mice. "AA" stands for amino acid. Panel (B) depicts a graph showing exonuclease deletion length frequencies at 5' region of JK segments in VELOCIMMUNE® mice expressing hTdT compared to VELOCIMMUNE® control mice. Het indicates a heterozygous mouse, HO indicates a homozygous mouse.
Figure 7:
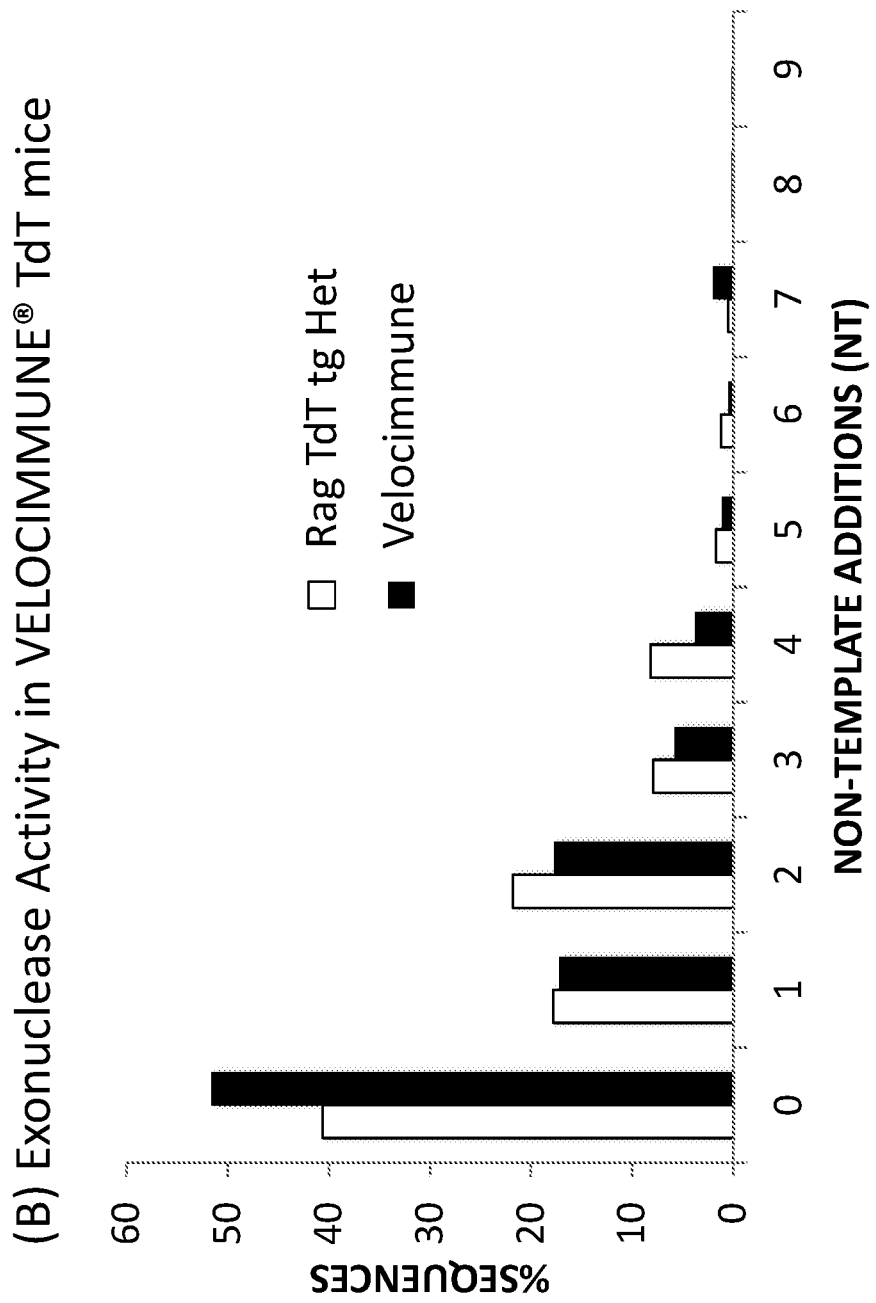

As depicted in FIG. 7A, increased non-template additions observed in the two versions of the human TdTS mice described in Examples 2 and 3 above led to increase in kappa light chain CDR3 length compared to control (VELOCIMMUNE® mice that comprise a functional ectopic mouse Adam6 gene). As depicted in FIG. 7B, sequence analysis revealed no extensive exonuclease activity affecting 5' J trimming rates in Rag-TdTS mice (only data for heterozygous mice is depicted here) as compared to control (VELOCIMMUNE® mice that comprise a functional ectopic mouse Adam6 gene).

Example 5. Human Light Chain Vκ and Jκ Gene Segment Usage in Human TdTS Mice

Figure 8:
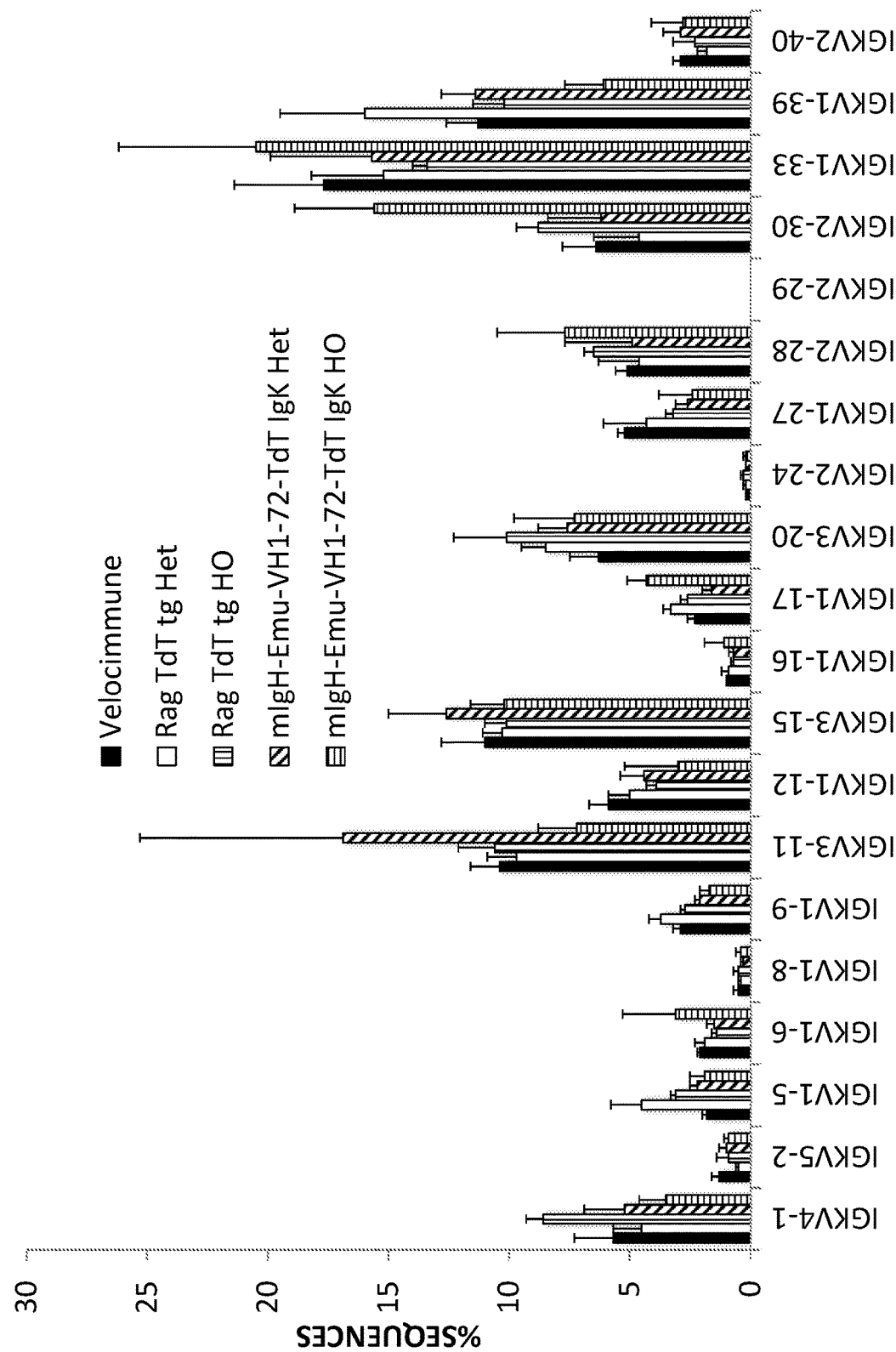
FIG. 8 has two panels. Panel (A) depicts a graph showing Vκ usage in VELOCIMMUNE® mice expressing hTdT compared to VELOCIMMUNE® control mice. Panel (B) depicts a graph showing Jκ usage in VELOCIMMUNE® mice expressing hTdT compared to VELOCIMMUNE® control mice. Het indicates a heterozygous mouse, HO indicates a homozygous mouse.
Figure 8:
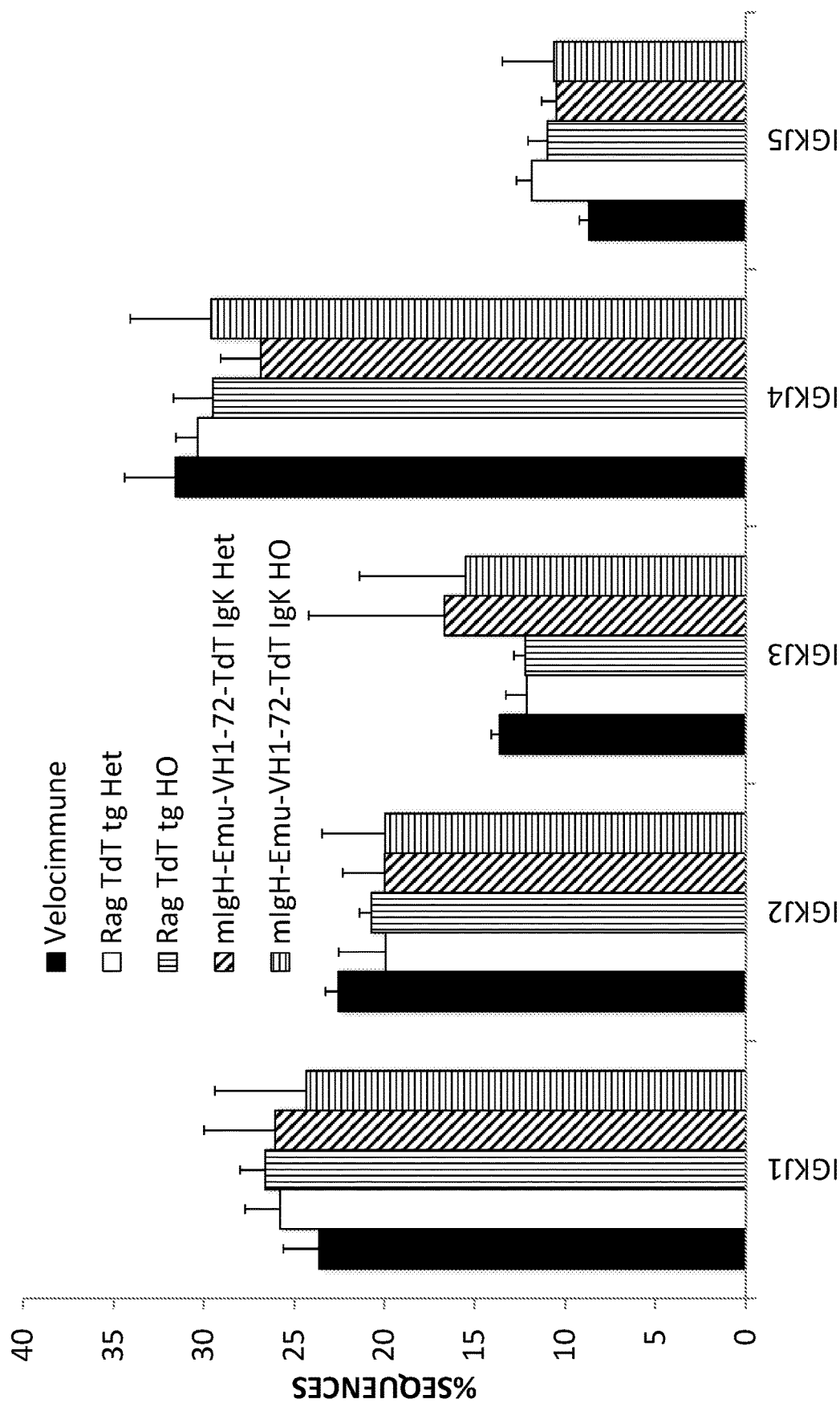

As depicted in FIGS. 8A and 8B, introduction of human TdTS in the two versions of the mice described un Examples 2 and 3 above did not significantly alter the usage of either Vκ gene segments or Jκ gene segments compared to VELOCIMMUNE® mice that comprise a functional ectopic mouse Adam6 gene.

Example 6. Junctional Diversity at Light Chain Lambda Immunoglobulin Locus and Other Rearranging Loci in Mice Comprising Human TdTS In addition to human immunoglobulin kappa locus, antigen-receptor diversity in other loci from B (λ light chain, heavy chain) and T (α/β) lymphocytes can be investigated.

Figure 9:
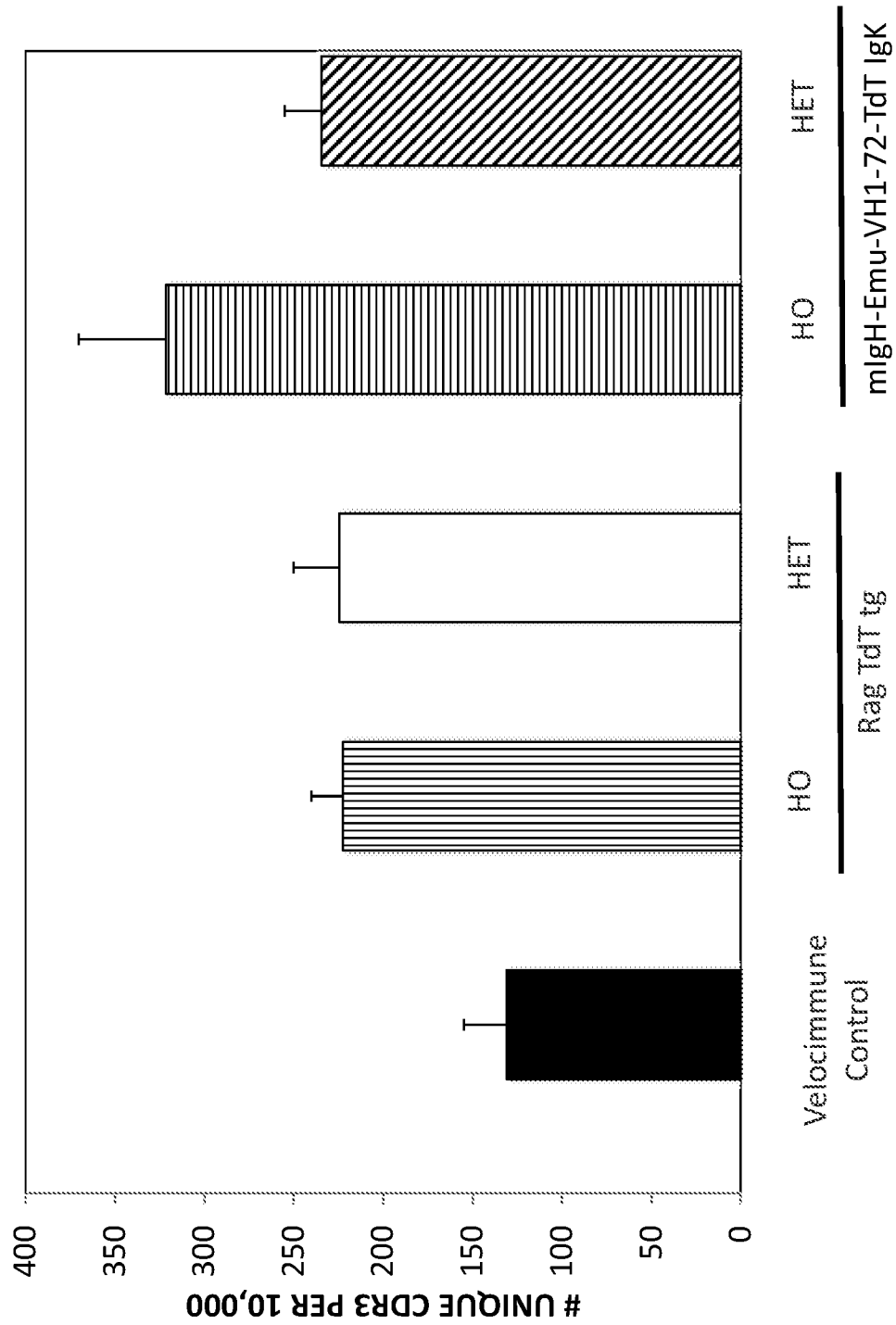
FIG. 9 depicts a graph showing mIgλ sequence diversity (# of unique light chain CDR3 sequences per 10,000 Igλ sequencing reads) in VELOCIMMUNE® mice expressing hTdT compared to VELOCIMMUNE® control mice. Het indicates a heterozygous mouse, HO indicates a homozygous mouse.
Figure 10:
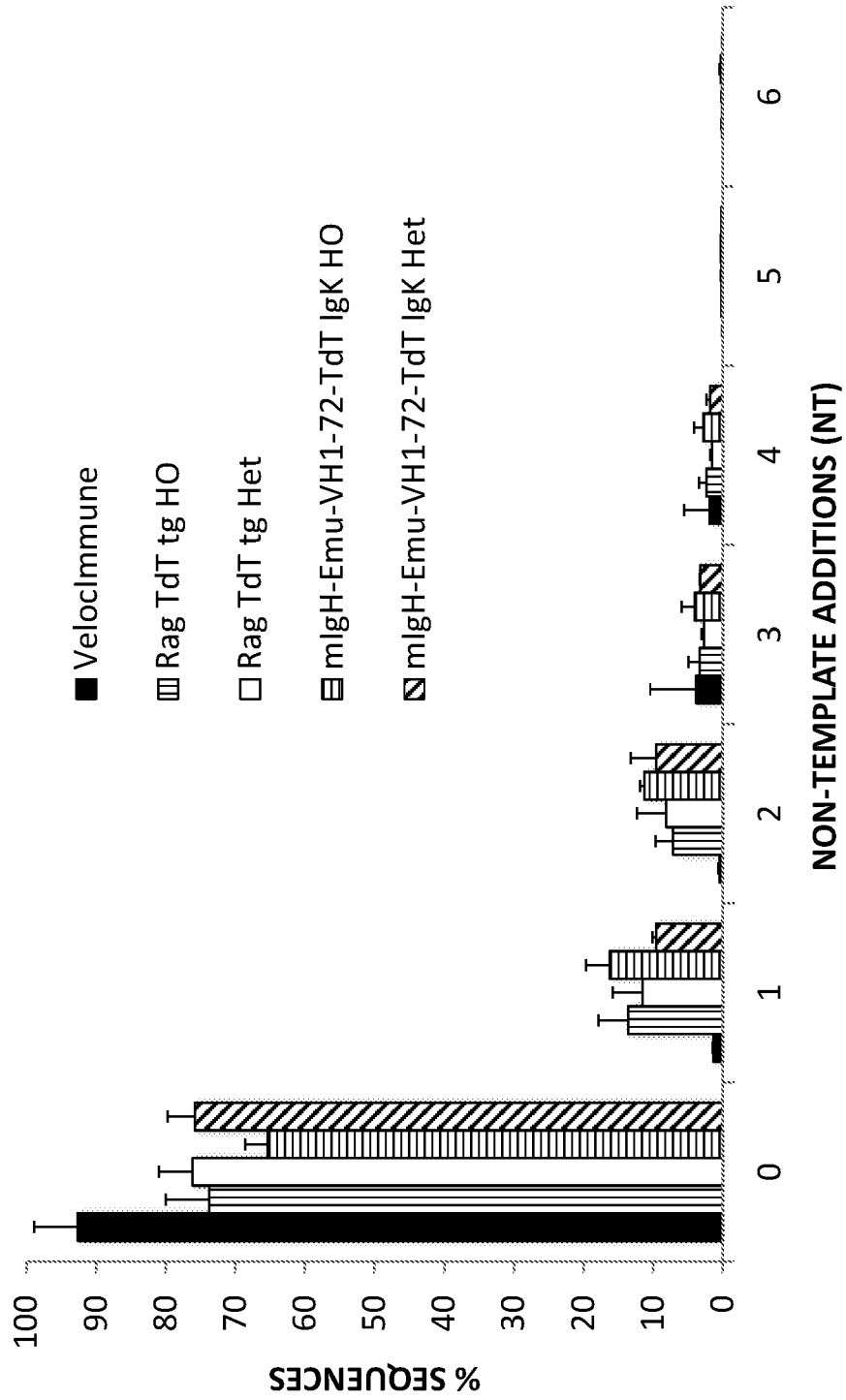
FIG. 10 depicts a graph showing the distribution of mIgλ non-template additions in VELOCIMMUNE® mice expressing hTdT compared to VELOCIMMUNE® control mice. Het indicates a heterozygous mouse, HO indicates a homozygous mouse. "NT" stands for nucleotides.
Figure 11:
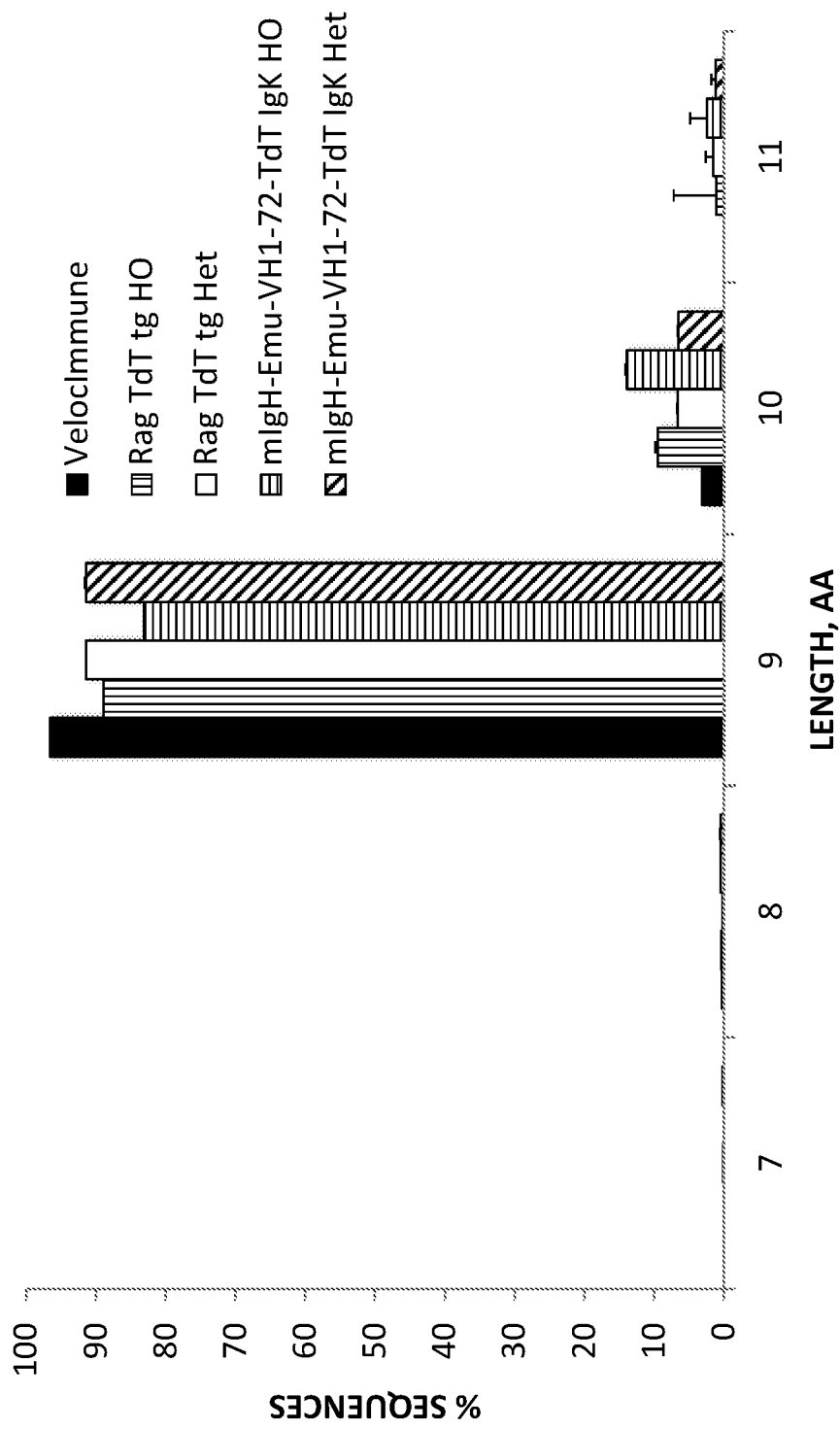
FIG. 11 depicts a graph showing the distribution of mIgλ CDR3 lengths in VELOCIMMUNE® mice expressing hTdT compared to VELOCIMMUNE® control mice. Het indicates a heterozygous mouse, HO indicates a homozygous mouse. "AA" stands for amino acid.
Figure 12:
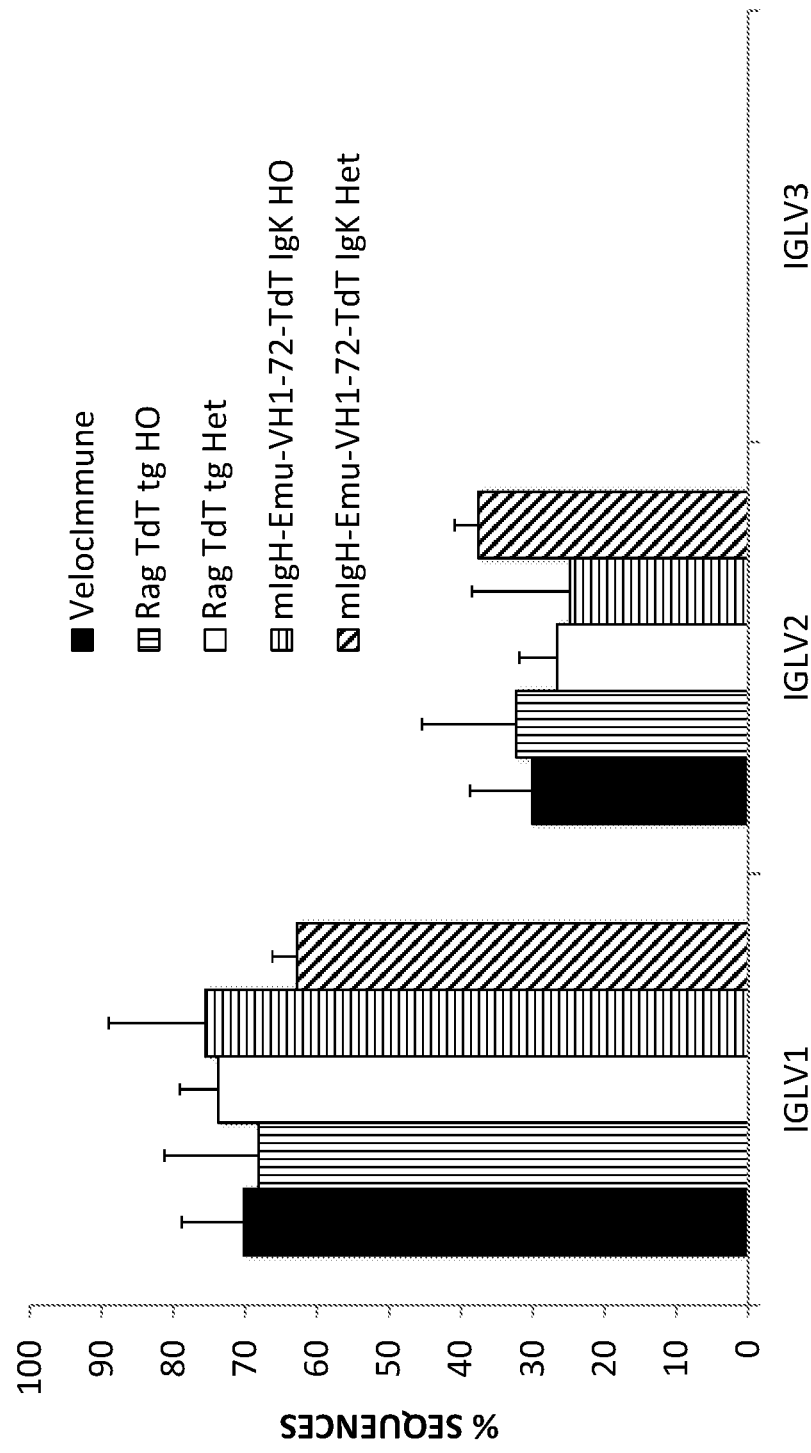
FIG. 12 depicts a graph showing Vλ usage in VELOCIMMUNE® mice expressing hTdT compared to VELOCIMMUNE® control mice. Het indicates a heterozygous mouse, HO indicates a homozygous mouse.

For example, when C λ1-containing lambda light junctional diversity in VELOCIMMUNE® mice that comprise a functional ectopic mouse Adam6 gene was compared to the same VELOCIMMUNE® mice also comprising human TdT transgenes described in Example 1 above using the same sequencing method as described in Example 2 and the primers listed in Table 5, increased sequence diversity (about 2 fold) was observed at the mouse lambda locus of transgenic mice (FIG. 9). In addition, we observed increased rate of mouse immunoglobulin lambda non-template additions (FIG. 10). CDR3 lengths of the lambda chains in the TdT transgenic mice are depicted in FIG. 11. Finally, no difference in the mouse V lambda usage was observed between the various tested animals (FIG. 12).

TABLE 5

Primers used in library preparation for IgL-C1 repertoire sequencing

| | | |
|---|---|---|
| RT primers | IgL (SEQ ID NO: 24) | 5'-CACCAGTGTGGCCTTGTTAGTCTC-3' |
| 1st round PCR primers | IgL Constant (SEQ ID NO: 25) | 5'-ACACTCTTTCCCTACACGACGCTCTTCCGATCT AAGGTGGAAACAGGGTGACTGATG-3' |
| | PE2-PIIA (SEQ ID NO: 21) | 5'-GTGACTGGAGTTCAGACGTGTGCTCTTCCGATC TAAGCAGTGGTATCAACGCAGAGT-3' |
| 2nd round PCR Primers | Forward (SEQ ID NO: 22) | 5'-AATGATACGGCGACCACCGAGATCTACACXXXX XXACACTCTTTCCCTACACGACGCTCTTCCGAT CT-3' |
| | Reverse (SEQ ID NO: 23) | 5'-CAAGCAGAAGACGGCATACGAGATXXXXXX GTGACTGGAGTTCAGACGTGTGCTCTTCCGATC T-3' |

Additionally, to the VELOCIMMUNE® mice that comprise unrearranged human heavy and light chain variable gene segments, including those comprising functional ectopic mouse Adam6 gene as described above (e.g., U.S. Pat. Nos. 8,878,001; 9,078,418; 9,125,386, incorporated herein by reference), or mice comprising only unrearranged human heavy chain variable gene segments or unrearranged human light chain variable gene segments, other animals can be generated that contain a human TdTS. Some such animals include those comprising a human lambda variable region either on endogenous mouse lambda or kappa locus (U.S. Pat. Nos. 9,035,128; 9,066,502; 9,163,092; 9,120,662; 9,029,628; 9,006,511; 9,012,717), a human kappa variable region at the endogenous heavy chain locus (e.g., U.S. Patent Application Publication No. 2012/0096572), a humanized TCR alpha and beta loci (e.g., U.S. Pat. No. 9,113,616) and various permutations thereof, dual light chain mice and permutations thereof (US Patent Application Publication No. 2013/0198880), universal light chain mice and permutations thereof (e.g., US Patent Application Publication Nos. 2011/0195454; 2013/018582), universal heavy chain mice and permutations thereof (e.g., U.S. Pat. No. 9,204,624), mice comprising histidine substitutions in their germline genome (e.g., U.S. Pat. Nos. 9,334,334 and 9,301,510, US Patent Application Publication Nos. 2013/0247236, 2014/0013456), chimeric antigen receptor mice (e.g., US Patent Application Publication No. 2016/0081314), mice lacking a CH1 domain (e.g., U.S. Pat. No. 8,754,287 and US Patent Application Publication No. 2015/0289489), all incorporated herein by reference. Any such animals where one desires to increase junctional diversity either at the light and/or heavy chain (e.g., human light and/or heavy chain) may be generated by introducing into ES cells comprising such modifications either a transgene or a targeted insertion of human TdTS described herein. In case of mice generated from ES cells comprising randomly integrated TdTS transgene (and in cases where IgK locus has not been modified, e.g., humanized TCR loci mice), they can be also generated by breeding with mice comprising various above-mentioned modifications. Successful incorporation of TdTS allele into such animals is determined as described herein above, and effect of human TdTS expression on generation of junctional diversity at various loci is determined as described herein above. The effect on non-modified rearranging loci, e.g., endogenous mouse immunoglobulin and T cell loci, is also studied.

One such example, where the effect of TdTs introduction on junctional diversity of Dual Light Chain mice was studied, is presented in Examples 7-10 below.

Example 7. Human Immunoglobulin Kappa Junctional Diversity in Dual Light Chain (DLC) Mice Comprising Human TdTS Mice comprising a dual light chain locus and human TdTS were generated by breeding VELOCIMMUNE® mice comprising a functional mouse Adam6 gene (see U.S. Pat. Nos. 8,642,835 and 8,697,940) and exogenous human TdTS with mice comprising the dual light chain locus (see U.S. Patent Application Publication Number US 2013/0198880, incorporated herein by reference).

To assess immunoglobulin repertoire sequence diversity in DLC human TdTS mouse models that have a limited IgK loci containing only two unrearranged $V_\kappa$ gene segments: IGVK3-20 and IGVK1-39, and five unrearranged IGJK gene segments (see U.S. Patent Application Publication Number US2013/0198880, incorporated herein by reference), IgK sequences were amplified by 5' RACE from spleens of various mice with mIgK constant primer and sequenced using Illumina MiSeq. In most experiments, several mice heterozygous for Rag TdT Tg and homozygous for the DLC locus (Rag TdT tg (HET) DLC) and two mice homozygous for Rag TdT Tg and homozygous for the DLC locus (Rag TdT tg (HO) DLC) were used; data for Rag TdT tg (HET) DLC is depicted as mean of all mice tested, while the two Rag TdT tg (HO) DLC mice are shown individually.

Specifically, splenic B cells were positively enriched from total splenocytes by magnetic cell sorting using anti-CD19 (mouse) magnetic beads and MACS® columns (Miltenyi Biotech). Total RNA was isolated from the purified splenic B cells using an RNeasy Plus RNA isolation kit (Qiagen) according to manufacturer's instructions. Reverse transcription was performed to generate cDNA containing Igκ constant region sequence, using a SMARTer™ RACE cDNA Amplification Kit (Clontech) and an Igκ specific primer (Table 4). During this process, a DNA sequence, which is reverse compliment to 3' of primer PE2-PIIA, was attached to the 3' end of the newly synthesized cDNAs. Purified Igκ specific cDNAs were then amplified by the 1st round PCR using the PE2-PIIA primer and an Igκ constant specific primer listed in Table 4. PCR products between 450-700 bp were isolated using Pippin Prep (SAGE Science). These products were further amplified by a 2nd round PCR using primers listed in Table 4 ("XXXXXX" represents a 6 bp index sequences to enable multiplexing samples for sequencing). PCR products between 400 bp-700 bp were isolated, purified, and quantified by qPCR using a KAPA Library Quantification Kit (KAPA Biosystems) before loading onto a Miseq sequencer (Illumina) for sequencing using Miseq Reagent Kits v3 (600 cycles).

For bioinformatics analysis, raw Illumina sequences were de-muliplexed and filtered based on quality, length and perfect match to kappa constant region primer. Overlapping paired-end reads were merged and analyzed using custom in-house pipeline. The pipeline used local installation of IgBLAST (NCBI, v2.2.25+) to align rearranged light chain sequences to human germline V and J gene database. Rearrangements were considered productive if no stop codons were detected and VJ junction was in-frame with J segment. Otherwise rearrangements were considered nonproductive and excluded from analysis.

CDR3 sequences were extracted using International Immunogenetics Information System (IMGT) boundaries. Junctional region between annotated V and J segments was classified as P and N nucleotides (non-template additions). Region with N/P additions was extracted from each sequence and its length calculated. Diversity of antibody repertoire was calculated by analyzing unique clonotypes. Sequence diversity was defined as a number of unique CDR3 sequences in randomly chosen 10,000 reads.

Figure 13:
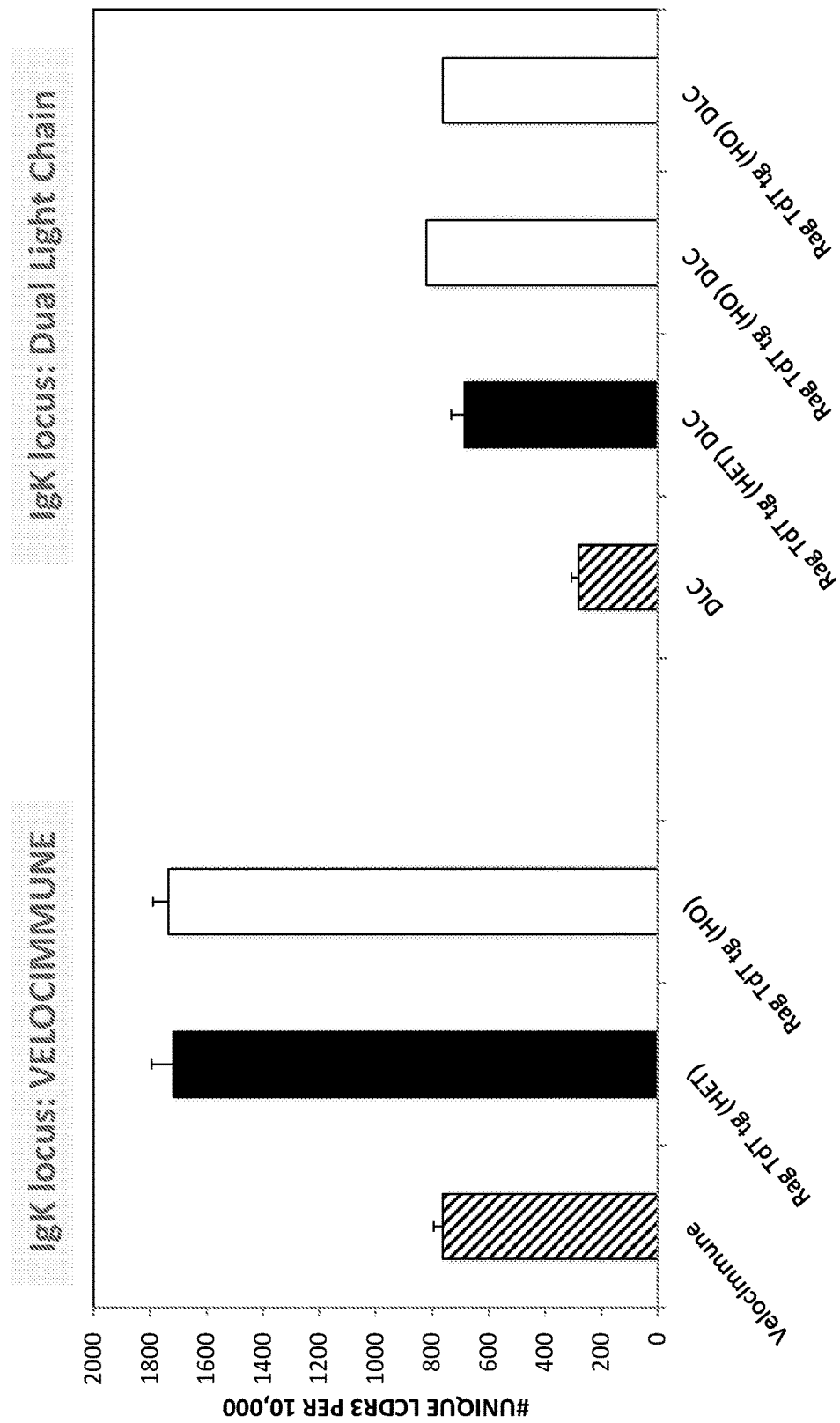
FIG. 13 depicts a graph showing hIgκ sequence diversity (# of unique light chain CDR3 sequences per 10,000 Igκ sequencing reads) in dual light chain mice (DLC; mice comprising two unrearranged human Vk gene segments and five unrearranged human Jk gene segments, as well as a diverse repertoire of unrearranged human heavy chain V, D, and J gene segments) expressing hTdT (right panel; hTdT genes present as indicated) compared to VELOCIMMUNE® mice expressing hTdT (left panel; hTdT genes present as indicated) and DLC and VELOCIMMUNE® control mice that do not express hTdT. Het indicates a heterozygous mouse for hTdT, HO indicates a homozygous mouse for hTdT.

FIG. 13 shows that over a 2-fold increase in the number of unique CDR3 amino acid sequences was detected in DLC human TdTS mouse models compared with DLC mice that did not comprise introduced human TdTS.

Example 8. Increase in Non-Germline Additions in DLC Mice Comprising Human TdTS Percentage of non-germline nucleotide additions in CDR3 (which consists of parts of both Vκ and Jκ gene segments) in immunoglobulin sequences of DLC TdT mice was also determined from Next Generation Sequencing described in Example 7 above.

Figure 14:
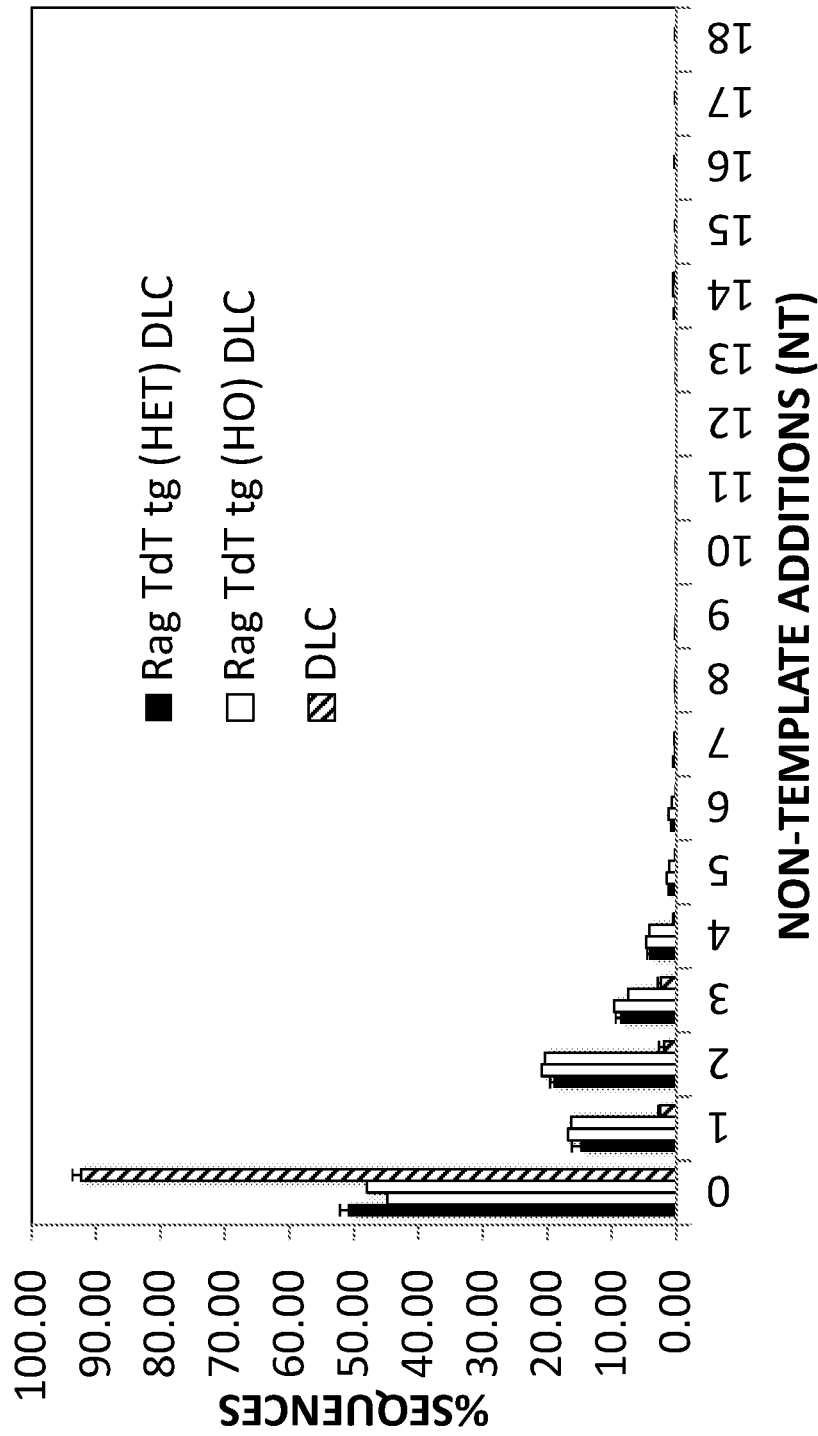
FIG. 14 depicts a graph showing the distribution of hIgκ non-template additions in mice expressing hTdT compared to DLC control mice not expressing hTdT (DLC). Het indicates a heterozygous mouse for hTdT, HO indicates a homozygous mouse for hTdT. "NT" stands for nucleotides.

As depicted in FIG. 14, about half of humanized kappa light chains in B cells were shown to have non-germline additions in DLC humanized TdTS mice (both HET and HO for TdT) as compared to about 10% in DLC control mice (DLC mice with no introduced human TdT).

Example 9. Human Light Chain CDR3 Lengths in Immunoglobulins Obtained from DLC Mice Comprising Human TdTS CDR3 sequences were extracted using International Immunogenetics Information System (IMGT) boundaries. Non-template nucleotides were determined from known light chain V and J sequences.

Figure 15:
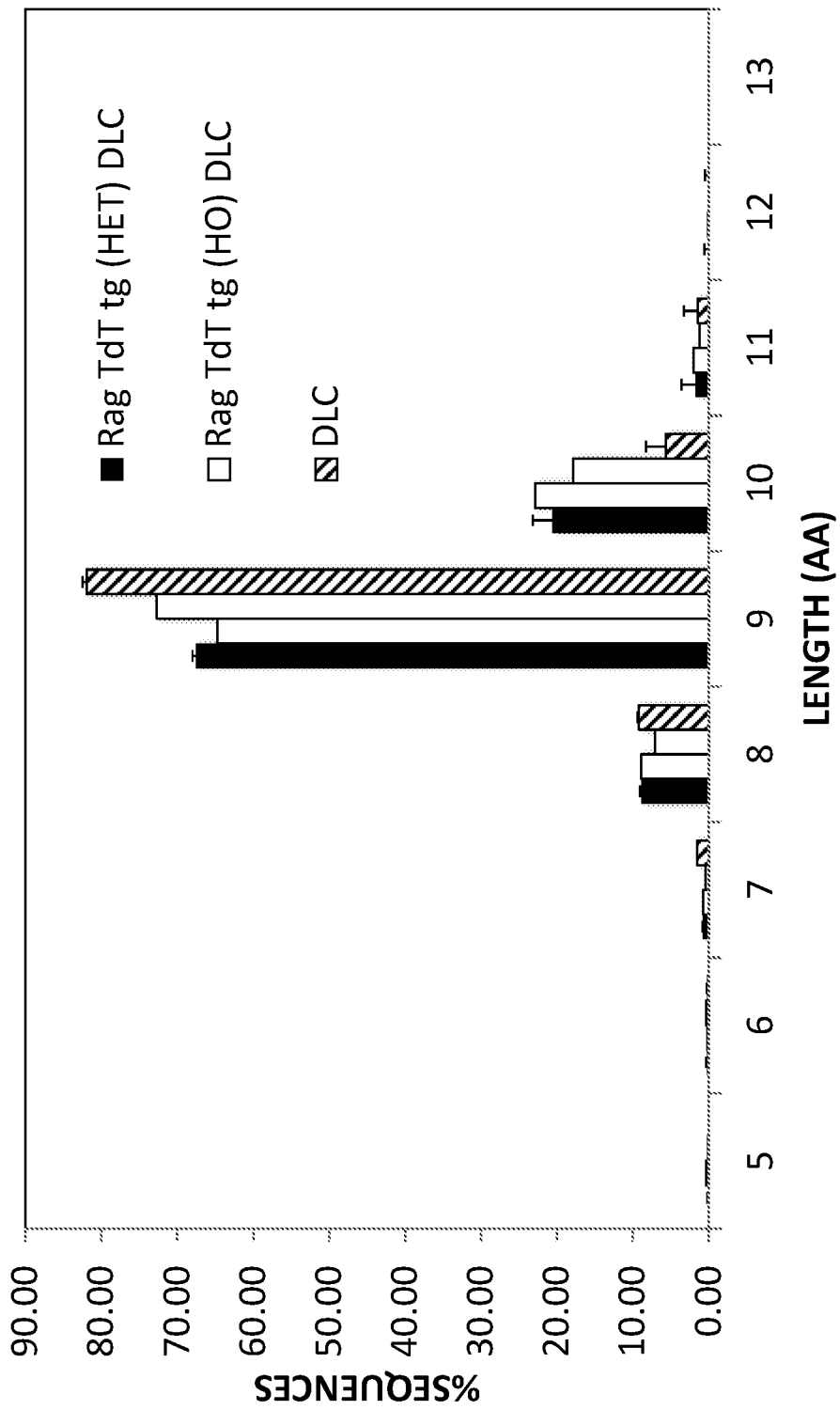
FIG. 15 depicts a graph showing the distribution of hIgκ CDR3 lengths in DLC mice expressing hTdT compared to DLC control mice not expressing hTdT. Het indicates a heterozygous mouse for hTdT, HO indicates a homozygous mouse for hTdT.

As depicted in FIG. 15, increased non-template additions observed in the DLC humanized TdTS mice (both HET and HO) described led to increase in kappa light chain CDR3 length compared to control (DLC mice with no introduced human TdT).

Figure 16:
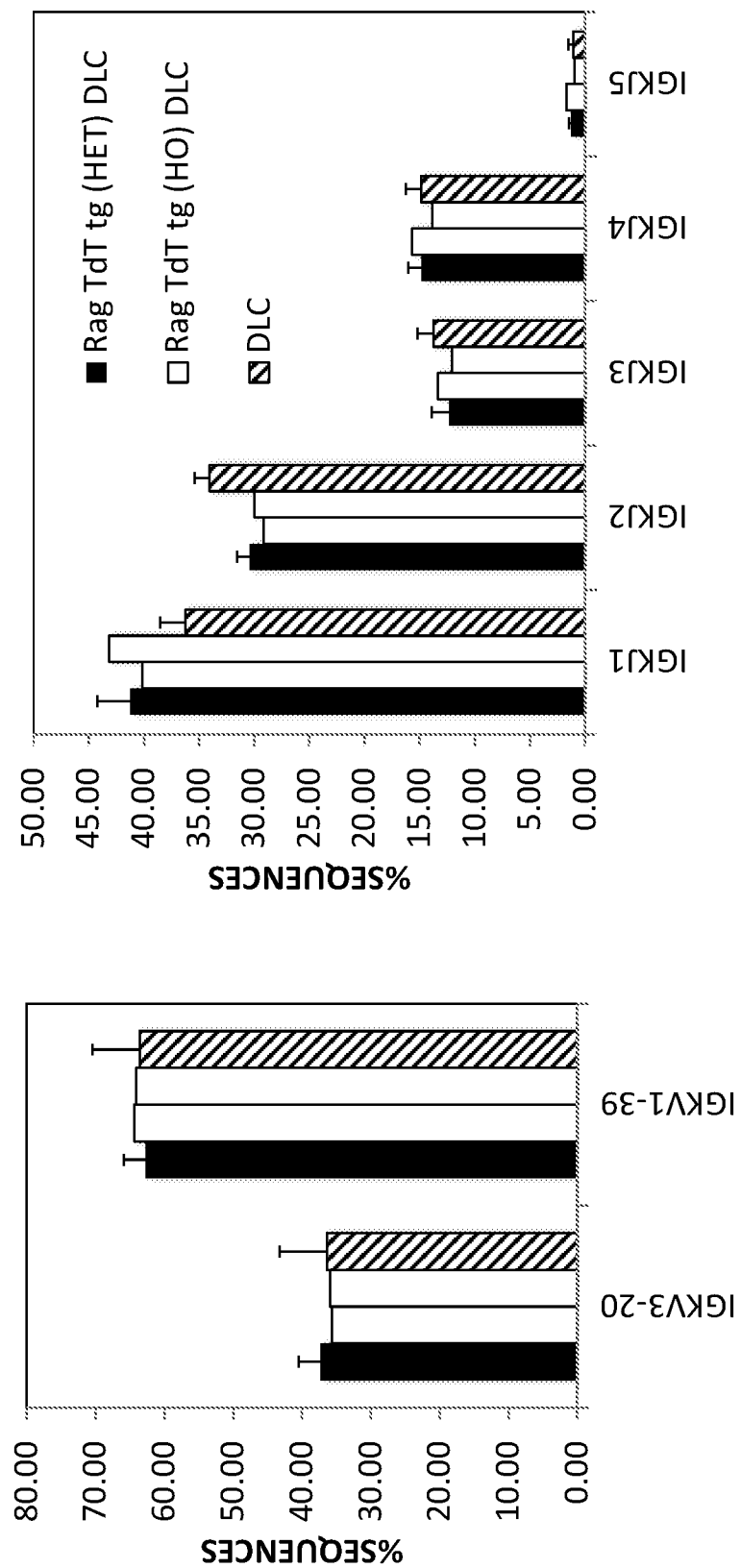
FIG. 16 depicts graphs showing Vκ usage and Jκ usage in DLC mice expressing hTdT compared to DLC control mice not expressing hTdT. Het indicates a heterozygous mouse for hTdT, HO indicates a homozygous mouse for hTdT. Only two different Rag TdT tg (HO) DLC mice where used, which are depicted separately.

Example 10. Human Light Chain Vκ and Jκ Gene Segment Usage in DLC Mice Comprising Human TdTS As depicted in FIG. 16, introduction of human TdTS in DLC mice did not significantly alter the usage of either Vκ gene segments or Jκ gene segments compared to DLC control mice (DLC mice with no introduced human TdT).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for making an antibody comprising:
(a) expressing in a host cell (i) a nucleic acid encoding an immunoglobulin heavy chain comprising a human immunoglobulin heavy chain variable region sequence operably linked to an immunoglobulin heavy chain constant region sequence and (ii) a nucleic acid encoding an immunoglobulin light chain comprising a human immunoglobulin light chain variable region sequence operably linked to an immunoglobulin light chain constant region sequence, wherein the human immunoglobulin heavy chain variable region sequence and/or the human immunoglobulin light chain variable region sequence were obtained from a B cell of a genetically modified mouse comprising in its germline genome:
  (i) a nucleic acid sequence encoding a human Terminal Deoxynucleotidyltransferase (TdT) operably linked to a human or mouse transcriptional control element, wherein the transcriptional control element is active in pre-B cells,
  (ii) a human immunoglobulin heavy chain variable region comprising unrearranged human immunoglobulin heavy chain V, D, and J gene segments operably linked to a human or mouse immunoglobulin heavy chain constant region, and
  (iii) a human immunoglobulin light chain variable region comprising unrearranged human immunoglobulin light chain V and J gene segments operably linked to a human or mouse immunoglobulin light chain constant region,
(b) culturing the host cell under conditions such that the host cell expresses an antibody comprising the immunoglobulin heavy chain and the immunoglobulin light chain.

2. The method of claim 1, wherein the transcriptional control element further drives expression of the nucleic acid sequence encoding the exogenous TdT in pro-B cells of the genetically modified rodent.

3. The method of claim 1, wherein the transcriptional control element comprises a RAG1 transcriptional control element, a RAG2 transcriptional control element, an immunoglobulin heavy chain transcriptional control element, an immunoglobulin κ light chain transcriptional control element, and/or an immunoglobulin λ light chain transcriptional control element.

4. The method of claim 1, wherein the nucleic acid sequence encoding the exogenous TdT is located at an immunoglobulin κ light chain locus, an immunoglobulin λ light chain locus, an immunoglobulin heavy chain locus, a RAG1 locus, or a RAG2 locus.

5. The method of claim 1, wherein at least 10% of the V-J immunoglobulin light chain junctions in the genetically modified rodent comprise non-template additions.

6. The method of claim 1, wherein the human light chain variable region operably linked to the human or mouse light chain constant region is located at an endogenous immunoglobulin light chain locus.

7. The method of claim 6, wherein the endogenous immunoglobulin light chain locus is a κ light chain locus.

8. The method of claim 6, wherein the endogenous immunoglobulin light chain locus is a λ light chain locus.

9. The method of claim 1, wherein the unrearranged human immunoglobulin light chain V and J gene segments are human Vκ and Jκ gene segments.

10. The method of claim 1, wherein the unrearranged human immunoglobulin light chain V and J gene segments are human Vλ and Jλ gene segments.

11. The method of claim 1, wherein the human or mouse immunoglobulin light chain constant region is a human or mouse κ constant region.

12. The method of claim 1, wherein the human or mouse immunoglobulin light chain constant region is a human or mouse λ constant region.

13. The method of claim 11, wherein the human or mouse κ constant region is a mouse κ constant region.

14. The method of claim 12, wherein the human or mouse λ constant region is a mouse λ constant region.

15. The method of claim 1, wherein the human or mouse immunoglobulin heavy chain constant region is a mouse heavy chain constant region.

16. The method of claim 1, wherein the human immunoglobulin heavy chain variable region operably linked to the human or mouse immunoglobulin heavy chain constant region is located at an endogenous immunoglobulin heavy chain locus.

17. The method of claim 1, wherein the unrearranged human immunoglobulin heavy chain V, D, and J gene segments and the unrearranged human immunoglobulin light chain V and J gene segments of the genetically modified rodent undergo rearrangement during B cell development to generate rearranged variable region genes in the B cells of the rodent.

18. The method of claim 17, wherein at least 10% of the rearranged variable region genes comprise non-template additions.

19. The method of claim 1, wherein the TdT is a short isoform of human TdT (TdTS).

* * * * *

SEQUENCE LISTING

```
<160> NUMBER OF SEQ ID NOS: 25

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtcgggtcgt ggt                                                        13

<210> SEQ ID NO 2
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 gcggccgc                                                               8

<210> SEQ ID NO 3
<211> LENGTH: 6
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 3 ccgcgg                                                                6

<210> SEQ ID NO 4
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tattgcgttt ttttaatcct ttcagataaa agacctattc acaatcaaaa atggatccac    60
cacgagcgtc ccacttgagc cctcggaaga agagacccc                           99

<210> SEQ ID NO 5
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gccctggctg agggaaattt tggaactccc aggctccaga cccattcttt gcgatcgctt    60
tagcaaaagc ccctcagact caggtatatt gctctctgaa tctactttt                108

<210> SEQ ID NO 6
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
ccaaaggaaa acacattggc aaataccaac ttctatgtgg agatcctatg gccggccggg    60
gatccagaca tgataagata cattgatgag tttggacaaa ccacaac                  107

<210> SEQ ID NO 7
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
tcgaccagga tgggcaccac cccggtgaac agctcctcgc ccttgctcac catgttggct    60
aagctacctg ggaacaatgg ggggggggg gggagtcaag                           100

<210> SEQ ID NO 8
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
catccttaca tctttgtcat ccctgtatc aacatggaaa ggcattaatg atctatgtcg     60
ggtgcggaga aagaggtaat gaaatggcaa ccggtataac ttcgtataat gtatgctata    120
cgaagttata tgcatggcc                                                139

<210> SEQ ID NO 9
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
ttcgtataat gtatgctata cgaagttatg tcgacctcga ggggggggccc acctccagct    60 gccttacaga aaagcaaatg cttgcttgca acaatcacct                          100

<210> SEQ ID NO 10
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tattgcgttt ttttaatcct ttcagataaa agacctattc acaatcaaaa atggatccac    60
cacgagcgtc ccacttgagc cctcggaaga agagacccc                           99

<210> SEQ ID NO 11
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gccctggctg agggaaattt tggaactccc aggctccaga cccattcttt gcgatcgctt    60
tagcaaaagc ccctcagact caggtatatt gctctctgaa tctactttt                108

<210> SEQ ID NO 12
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
cccaaaggaa aacacattgg caaataccaa cttctatgtg gagatcctat ggccggccgg    60
ggatccagac atgataagat acattgatga gtttggacaa accacaac                 108

<210> SEQ ID NO 13
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
tcgaccagga tgggcaccac cccggtgaac agctcctcgc ccttgctcac catgttggct    60
aagctacctg ggaacaatgg gggggggggg gggagtcaag                          100

<210> SEQ ID NO 14
<211> LENGTH: 151
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
acctctgctg tgtctgcaag tttggcttgt tcctgcttct gattttgggg tctagacccc      60
cgggctcgat aactataacg gtcctaaggt agcgactcga gcataaccac tttcctgcta     120
tggatctgtt aaatatccgc caaaggccaa g                                    151

<210> SEQ ID NO 15
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
catccttaca tctttgtcat ccctgtatc aacatggaaa ggcattaatg tcgctacctt       60
aggaccgtta tagttaggcc cccctcgag gtcgacataa cttcgtatag catacattat     120
acgaag                                                                126

<210> SEQ ID NO 16
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ggccatgcat ataacttcgt atagcataca ttatacgaag ttataccggt aaagaatggg      60
tctggagcct gggagttcca aaatttccct cagccagggc                           100

<210> SEQ ID NO 17
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
cggggtctct tcttccgagg gctcaagtgg gacgctcgtg gtggatccat ggtgaggtcc      60
tgtgtgctca gtaactgtaa agagaacagt gatctcatgt                           100

<210> SEQ ID NO 18
<211> LENGTH: 146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
tagtttcccc aaacttaagt ttatcgactt ctaaaatgta tttagaattc tgccatttca      60
ttacctcttt ctccgcaccc gacatagata aagcttcata accactttcc tgctatggat    120
ctgttaaata tccgccaaag gccaag    146

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aagaagcaca cgactgaggc ac    22

<210> SEQ ID NO 20
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acactctttc cctacacgac gctcttccga tctggaagat ggatacagtt ggtgc    55

<210> SEQ ID NO 21
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtgactggag ttcagacgtg tgctcttccg atctaagcag tggtatcaac gcagagt    57

<210> SEQ ID NO 22
<211> LENGTH: 68
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)..(35)
<223> OTHER INFORMATION: a, c, t, g, unknown or other

<400> SEQUENCE: 22
aatgatacgg cgaccaccga gatctacacn nnnnacact ctttccctac acgacgctct    60
tccgatct    68

<210> SEQ ID NO 23
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(30)
<223> OTHER INFORMATION: a, c, t, g, unknown or other

<400> SEQUENCE: 23
caagcagaag acggcatacg agatnnnnnn gtgactggag ttcagacgtg tgctcttccg    60
atct    64

```
<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caccagtgtg gccttgttag tctc                                                24

<210> SEQ ID NO 25
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acactctttc cctacacgac gctcttccga tctaaggtgg aaacagggtg actgatg            57
```